(12) United States Patent
Drizin et al.

(10) Patent No.: US 6,538,004 B2
(45) Date of Patent: Mar. 25, 2003

(54) TRICYCLIC DIHYDROPYRAZOLONE AND TRICYCLIC DIHYDROISOXAZOLONE POTASSIUM CHANNEL OPENERS

(75) Inventors: Irene Drizin, Wadsworth, IL (US); Robert J. Altenbach, Chicago, IL (US); William A. Carroll, Evanston, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/778,551

(22) Filed: Feb. 7, 2001

(65) Prior Publication Data

US 2002/0007059 A1 Jan. 17, 2002

Related U.S. Application Data

(60) Provisional application No. 60/187,213, filed on Mar. 3, 2000.

(51) Int. Cl.$^7$ ............... A61K 31/437; A61K 31/4353; C07D 471/04; C07D 498/14; A61P 13/00
(52) U.S. Cl. ............ 514/293; 514/292; 546/83; 546/82
(58) Field of Search ............... 514/292, 293; 546/82, 83

(56) References Cited

U.S. PATENT DOCUMENTS

| | | | |
|---|---|---|---|
| 3,719,667 A | | 3/1973 | Gutowski et al. |
| 3,840,556 A | | 10/1974 | Kukolja et al. |
| 4,532,248 A | | 7/1985 | Franckowiak et al. |
| 4,883,872 A | | 11/1989 | Atwal |
| 5,270,308 A | * | 12/1993 | Shiraishi .................. 514/229.8 |
| 6,191,140 B1 | * | 2/2001 | Carroll ....................... 514/297 |

FOREIGN PATENT DOCUMENTS

| | | |
|---|---|---|
| DE | 87255 | 5/1910 |
| EP | 0 088 276 | 9/1983 |
| EP | 0299727 A1 | 11/1991 |
| EP | 0 705 830 | 4/1996 |
| JP | 2040385 | 2/1990 |
| WO | 99/32495 | 1/1989 |
| WO | 90/12015 | 10/1990 |
| WO | 00 24741 | 5/2000 |

OTHER PUBLICATIONS

Aldred, J. Chem. Soc. Perkin Trans. 1:1823 (1994).
Andersson, Pharmacological Reviews 45:253 (1993).
Andersson, Prostate 30:202–215 (1997).
Andersson, Urology, 50(Suppl 6A): 74–84 (1997).
Angyal, J. Chem. Soc. 2141 (1950).
Asano, Anesth, Analg. 90(5):1146–51 (2000).
Badder, J. Indian Chem. Soc. 53:1053 (1976).
Barbieri, W. et al. Tetrahedon 23: 4395–4406 (1967).
Barnes, J. Chem. soc. 2824 (1950).
Bauer, L., et al., *studies in the Chemistry of 3—and 5*–Isoxazolones, Tetrahedron 20:165–171 (1964).
Berge, S.M. et al., J. Pharmaceutical Sciences 66:1 et seq (1977).
Bergmann, J. Am. Chem. Soc. 81:5641 (1959).
Bosch, BJU International 83(suppl 2): 7–9 (1999).
Buchheit, Pulmonary Pharmacology & Therapeutics 12:103 (1999).
Clark, J. Fluorine Chem. 50:411 (1990).
Crawford, J. Chem. Soc. 2155 (1956).
D'Angelo, J., Tetrahedron Letters 32:3063 (1991).
Duff, J. Chem. Soc. 1512 (1951).
Eistert, Chem. Ber. 97:1470 (1964).
Ferguson, J. Am. Chem. Soc 72:4324 (1950).
Freedman, et al., The Neuroscientist, 2:145–152 (1996).
Garlid, Circ. Red. 81(6):1072–82 (1997).
Gasco, A.M. e t al., *Benzofurazanyl– and benzofuroxanyl–1,4–dihydropyridines: synthesis, structure a nd calcium entry blocker* activity, Eur. J. med. Chem. 31:3–10 (1996).
Gehlert, et al., Prog. Neuro –Psychopharmacol & Bio. Psychiat., v18:1093–1102 (1994).
Gilchrist, R., J. Chem. Soc. 2820 (1923).
Ginsburg, J. Am. Chem. Soc. 73:702 (1951).
Goldstein and Berman., *Vasculogenic female sexual dysfunction: vaginal engorgement and clitoral erectile insufficiency* syndromes, Int. J. Impotence Res., 10:S84 –S90 (1998).
Gopalakrishnan et al., Drug Development Research, 28:95 127 (1993).
Grover, J Mol Cell Cardio. 32:677 (2000).
Hampel, Urology 50(Suppl 6A):4– 14 (1997).
Hodgson, J. Chem. soc. 1635 (1929).
Hodgson, J. Chem. Soc. 1641 (1929).
Hodgson, J. Chem. Soc. 2425 (1927).
Hodgson, J. Chem. Soc. 469 (1929).
Howe et al., J. Pharmacol. Exp. Ther., 274:884–890 (1995).
Husband, S. et al., Tetrahedron, 51(3):865 (1995).

(List continued on next page.)

Primary Examiner—Evelyn Mei Huang
(74) *Attorney, Agent, or Firm*—Portia Chen; Michael J. Ward

(57) ABSTRACT

Compounds of formula I

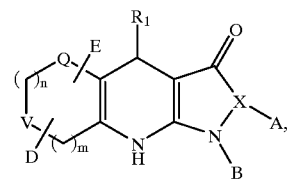

are useful in treating diseases prevented by or ameliorated with potassium channel openers. Also disclosed are potassium channel opening compositions and a method of opening potassium channels in a mammal.

19 Claims, No Drawings

OTHER PUBLICATIONS

IUPAC 1974 Recommendations for Section E, Fundamental Stereochemistry, Pure Appl. Chem. 45:13 –30 (1976).
J. Chem. Soc. Perkin Trans. 1:2677 (1981).
J. Chem. Soc. Perkin Trans. 1:315 (1990).
J. Med. Chem. 29:1982 (1986).
Justus Liebigs Ann. Chem. 294:381 (1897).
Kalme, ZA et al., Khim. Geterotsikl. Soedin. 9:1218 –22 (1992).
Khanna, J. Med. Chem. 40:1634 (1997).
Klockner, U. et al., Pfugers Arch. 405:329 –339 (1985).
Komiyama, J. Am. Chem. Soc. 105:2018 (1983).
Kostrzewska, Acta Obstet. Gynecol. Scand. 75(10), 886 –91 (1996).
Lawson, Pharmacol. Ther., v70:39– 63 (1996).
Lee, Int. J. Impot. Res. 11(4):179–188 (1999).
Manley, J. Med. Chem. 35:2327–2340 (1992).
Midland, M. Tetrahedron 40:1371– 1380 (1984).
Monatsh. Chem. 94:1262 (1963).
Morrison, Am. J. obstet. Gynecol, 169(5):1277– 85 (1993).
Nagao, Tetrahedron Lett. 21:4931 (1980).
Nakagawa, S., Heterocycles 13:477 (1979).
Nurse et al., Br. J. Urol., 68:27– 31 (1991).
Nwaukwa, Tetrahedron Lett. 23:3131 (1982).
Pandita, The J. of Urology 162:943 (1999).
Park, K.K. et al., *Sodium Dithionite Reduction of Nitroarenes Using Violgen as an Electron Phase– Transfer* Catalyst, Tetrahedron Lett. 34:7445– 7446 (1993).
Pearson D.E. et al., *The Swaming Catalyst Effect, II. Nuclear Halogenation of Aromatic Aldehydes and* Ketones, J. Org. Chem. 23:1412–1415 (1958).
Pearson, Org. Synth. Coll. V:117 (1973).
Prescott, Ed., Methods in Cell Biology, Academic Press, New York, NY v14:33 et seq (1976).
Quast et al. Mol. Pharmacol. 43:474– 481 (1993).
Resnick, The Lancet 346:94– 99 (1995).
Rinkes, Recl. Trav. Chim. Pays–Bas 64:205 (1945).
Roche, E.B., Bioreversible Carriers inDrug Design: Theory and Application, Pergamon Press, New York, p14–21 (1987).
Rodrigues, Br. J. Pharmacol 129(1):110 –4 (2000).
Sanborn, Semin. Perinatol. 19:31– 40 (1995).
Schroeder, K. S. et al., J. Biomed. Screen 1:75 –81 (1996).
Sekikawa, Bull. Chem. Jpn. 31:551 (1959).
Smith, R., J. Med. Chem. 31:1558– 1566 (1988).
Spanswick et al., Nature 390:521– 25 (Dec. 4, 1997).
Sugihara, Y. et al., *Upper Excited State Reactivity and Fluroescence of Fused 8– Cyanoheptafulvenes*. J. Am. Chem. Soc. 107:5894–5897 (1985).
Tanouchi, J. Med. Chem. 24:1149 (1981).
Taylor, C. et al., *Synthesis of 2– Aminonicotinamides by Raney Nickel Cleavage of Pyra zolo [3,4–b]–pyridines*, J. Am. Chem. Soc. 81:2448–2452 (1959).
Terasawa, *Novel Heterocyclic Synthones, Snthesis and Properties of Thia –and Oxacyclohexane–3, 5diones*, J. Org. Chem. 42(7):1163–1169 (1977).
Tetrahedron Lett. 5495 (1990).
Ver der Lee, Recl. Trav. Chim. Pays–Bas 45:687 (1926).
Vergoni, Life Sci. 50(16):PL135– 8 (1992).
Lampel, J. Urol. 163:202 (2000).
Villagomez–Ibarra, Tetrahedron 51:9285 (1995) .
Weisberger, A. et al., *Investigation of Pyrazole Compound. VI. The Condensation of Some Heterocyclic Hydrazines with Ethyl Cyanoacetate*, J. Amer. Chem. Soc. 66:1849 –1851 (1944).
Widman, Chem. Ber. 15:167 (1882).
Ziegler, J. Amer. Chem. Soc. 95:7458 –7464 (1973).

* cited by examiner

TRICYCLIC DIHYDROPYRAZOLONE AND TRICYCLIC DIHYDROISOXAZOLONE POTASSIUM CHANNEL OPENERS

CROSS REFERENCE TO RELATED APPLICATION

This application is a continuation-in-part of provisional U.S. Patent Application Serial No. 60/187,213, filed on Mar. 3, 2000.

TECHNICAL FIELD

Novel tricyclic dihydropyrazolone and novel tricyclic dihydroisoxazolone compounds and their derivatives can open potassium channels and are useful for treating a variety of medical conditions.

BACKGROUND OF INVENTION

Potassium channels play an important role in regulating cell membrane excitability. When the potassium channels open, changes in the electrical potential across the cell membrane occur and result in a more polarized state. A number of diseases or conditions may be treated with therapeutic agents that open potassium channels; see for example (K. Lawson, Pharmacol. Ther., v. 70, pp. 39–63 (1996)); (D. R. Gehlert et al., Prog. Neuro-Psychopharmacol & Biol. Psychiat., v. 18, pp. 1093–1102 (1994)); (M. Gopalakrishnan et al., Drug Development Research, v. 28, pp. 95–127 (1993)); (J. E. Freedman et al., The Neuroscientist, v. 2, pp. 145–152 (1996)); (D. E. Nurse et al., Br. J. Urol., v. 68 pp27–31 (1991)); (B. B. Howe et al., J. Pharmacol. Exp. Ther., v. 274 pp. 884–890 (1995)); (D. Spanswick et al., Nature, v. 390 pp. 521–25 (Dec. 4, 1997)); (Dompeling Vasa. Supplementum (1992) 3434); (WO9932495); (Grover, J Mol Cell Cardiol. (2000) 32, 677); and (Buchheit, Pulmonary Pharmacology & Therapeutics (1999) 12, 103). Such diseases or conditions include asthma, epilepsy, male sexual dysfunction, female sexual dysfunction, pain, bladder overactivity, stroke, diseases associated with decreased skeletal blood flow such as Raynaud's phenomenon and intermittent claudication, eating disorders, functional bowel disorders, neurodegeneration, benign prostatic hyperplasia (BPH), dysmenorrhea, premature labor, alopecia, cardioprotection, coronary artery disease, angina and ischemia.

Bladder overactivity is a condition associated with the spontaneous, uncontrolled contractions of the bladder smooth muscle. Bladder overactivity thus is associated with sensations of urgency, urinary incontinence, pollakiuria, bladder instability, nocturia, bladder hyerreflexia, and enuresis (Resnick, The Lancet (1995) 346, 94–99;Hampel, Urology (1997) 50 (Suppl 6A), 4–14; Bosch, BJU International (1999) 83 (Suppl 2), 7–9). Potassium channel openers (KCOs) act as smooth muscle relaxants. Because bladder overactivity and urinary incontinence can result from the spontaneous, uncontrolled contractions of the smooth muscle of the bladder, the ability of potassium channel openers to hyperpolarize bladder cells and relax bladder smooth muscle may provide a method to ameliorate or prevent bladder overactivity, pollakiuria, bladder instability, nocturia, bladder hyperreflexia, urinary incontinence, and enuresis (Andersson, Urology (1997) 50 (Suppl 6A), 74–84; Lawson, Pharmacol. Ther., (1996) 70, 39–63; Nurse., Br. J. Urol., (1991) 68, 27–31;Howe, J. Pharmacol. Exp. Ther., (1995) 274, 884–890; Gopalakrishnan, Drug Development Research, (1993) 28, 95–127).

The irritative symptoms of BPH (urgency, frequency, nocturia and urge incontinence) have been shown to be correlated to bladder instability (Pandita, The J. of Urology (1999) 162, 943). Therefore the ability of potassium channel openers to hyperpolarize bladder cells and relax bladder smooth muscle may provide a method to ameliorate or prevent the symptoms associated with BPH. (Andersson; Prostate (1997) 30: 202–215).

The excitability of corpus cavernosum smooth muscle cells is important in the male erectile process. The relaxation of corporal smooth muscle cells allows arterial blood to build up under pressure in the erectile tissue of the penis leading to erection (Andersson, Pharmacological Reviews (1993) 45, 253). Potassium channels play a significant role in modulating human corporal smooth muscle tone, and thus, erectile capacity. By patch clamp technique, potassium channels have been characterized in human corporal smooth muscle cells (Lee, Int. J. Impot. Res. (1999) 11(4),179–188). Potassium channel openers are smooth muscle relaxants and have been shown to relax corpus cavemosal smooth muscle and induce erections (Andersson, Pharmacological Reviews (1993) 45, 253; Lawson, Pharmacol. Ther., (1996) 70, 39–63, Vick, J. Urol. (2000) 163: 202). Potassium channel openers therefore may have utility in the treatment of male sexual dysfunctions such as male erectile dysfunction, impotence and premature ejaculation.

The sexual response in women is classified into four stages: excitement, plateau, orgasm and resolution. Sexual arousal and excitement increase blood flow to the genital area, and lubrication of the vagina as a result of plasma transudation. Topical application of KCOs like minoxidil and nicorandil have been shown to increase clitoral blood flow (J. J. Kim, J. W. Yu, J. G. Lee, D. G. Moon, "Effects of topical K-ATPchannel opener solution on clitoral blood flow", J. Urol. (2000) 163 (4): 240). KCOs may be effective for the treatment of female sexual dysfunction including clitoral erectile insufficiency, vaginismus and vaginal engorgement (I. Goldstein and J. R. Berman., "Vasculogenic female sexual dysfunction: vaginal engorgement and clitoral erectile insufficiency syndromes"., Int. J. Impotence Res. (1998) 10:S84–S90), as KCOs can increase blood flow to female sexual organs.

Potassium channel openers may have utility as tocolytic agents to inhibit uterine contractions to delay or prevent premature parturition in individuals or to slow or arrest delivery for brief periods to undertake other therapeutic measures (Sanborn, Semin. Perinatol. (1995) 19, 31–40; Morrison Am. J. Obstet. Gynecol. (1993) 169(5), 1277–85). Potassium channel openers also inhibit contractile responses of human uterus and intrauterine vasculature. This combined effect would suggest the potential use of KCOs for dysmenhorrea (Kostrzewska, Acta Obstet. Gynecol. Scand.(1996) 75(10), 886–91). Potassium channel openers relax uterine smooth muscle and intrauterine vasculature and therefore may have utility in the treatment of premature labor and dysmenorrhoea (Lawson, Pharmacol. Ther., (1996) 70, 39–63).

Potassium channel openers relax gastrointestinal smooth tissues and therefore may be useful in the treatment of functional bowel disorders such as irritable bowel syndrome (Lawson, Pharmacol. Ther., (1996) 70, 39–63).

Potassium channel openers relax airway smooth muscle and induce bronchodilation. Therefore potassium channel openers may be useful in the treatment of asthma and airways hyperreactivity (Lawson, Pharmacol. Ther., (1996) 70, 39–63; Buchheit, Pulmonary Pharmacology & Therapeutics (1999) 12, 103; Gopalakrishnan, Drug Development Research, (1993) 28, 95–127).

Neuronal hyperpolarization can produce analgesic effects. The opening of potassium channels by potassium channel openers and resultant hyperpolarization in the membrane of target neurons is a key mechanism in the effect of opioids. The peripheral antinociceptive effect of morphine results from activation of ATP-sensitive potassium channels, which causes hyperpolarization of peripheral terminals of primary afferents, leading to a decrease in action potential generation (Rodrigues, Br J Pharmacol (2000) 129(1), 110–4). Opening of $K_{ATP}$ channels by potassium channel openers plays an important role in the antinociception mediated by alpha-2 adrenoceptors and mu opioid receptors. KCOs can potentiate the analgesic action of both morphine and dexmedetomidine via an activation of $K_{ATP}$ channels at the spinal cord level (Vergoni, Life Sci.(1992) 50(16), PL135-8; Asano, Anesth. Analg. (2000) 90(5), 1146-51). Thus, potassium channelopeners can hyperpolarize neuronal cells and have shown analgesic effects. Potassium channel openers therefore may be useful as analgesics in the treatment of various pain states including but not limited to migraine and dyspareunia (Lawson, Pharmacol. Ther., (1996) 70, 39–63; Gopalakrishnan, Drug Development Research, (1993) 28, 95–127; Gehlert, Prog. Neuro-Psychopharmacol. & Biol. Psychiat., (1994) 18, 1093–1102).

Epilepsy results from the propagation of nonphysiologic electrical impulses. Potassium channel openers hyperpolarize neuronal cells and lead to a decrease in cellular excitability and have demonstrated antiepileptic effects. Therefore potassium channel openers may be useful in the treatment of epilepsy (Lawson, Pharmacol. Ther., (1996) 70, 39–63; Gopalakrishnan, Drug Development Research, (1993) 28, 95–127; Gehlert, Prog. Neuro-Psychopharmacol. & Biol. Psychiat., (1994) 18, 1093–1102).

Neuronal cell depolarization can lead to excitotoxicity and neuronal cell death. When this occurs as a result of acute ischemic conditions, it can lead to stroke. Long-term neurodegeneration can bring about conditions such as Alzheimer's and Parkinson's diseases. Potassium channel openers can hyperpolarize neuronal cells and lead to a decrease in cellular excitability. Activation of potassium channels has been shown to enhance neuronal survival. Therefore potassium channel openers may have utility as neuroprotectants in the treatment of neurodegenerative conditions and diseases such as cerebral ischemia, stroke, Alzheimer's disease and Parkinson's disease (Lawson, Pharmacol. Ther., (1996) 70, 39–63; Gopalakrishnan, Drug Development Research, (1993) 28, 95–127; Gehlert, Prog. Neuro-Psychopharmacol & Biol. Psychiat., (1994) 18, 1093–1102; Freedman, The Neuroscientist (1996) 2, 145).

Potassium channel openers may have utility in the treatment of diseases or conditions associated with decreased skeletal muscle blood flow such as Raynaud's syndrome and intermittent claudication (Lawson, Pharmacol. Ther., (1996) 70, 39–63; Gopalakrishnan, Drug Development Research, (1993) 28, 95–127; Dompeling Vasa. Supplementum (1992) 3434; and WO9932495).

Potassium channel openers may be useful in the treatment of eating disorders such as obesity (Spanswick, Nature, (1997) 390, 521-25; Freedman, The Neuroscientist (1996) 2, 145).

Potassium channel openers have been shown to promote hair growth therefore potassium channel openers have utility in the treatment of hair loss and baldness also known as alopecia (Lawson, Pharmacol. Ther., (1996) 70, 39–63; Gopalakrishnan, Drug Development Research, (1993) 28, 95–127).

Potassium channel openers possess cardioprotective effects against myocardial injury during ischemia and reperfusion. (Garlid, Circ. Res. (1997) 81(6), 1072-82). Therefore, potassium channel openers may be useful in the treatment of heart diseases (Lawson, Pharmacol. Ther., (1996) 70, 39–63; Grover, J. Mol. Cell Cardiol. (2000) 32, 677).

Potassium channel openers, by hyperpolarization of smooth muscle membranes, can exert vasodilation of the collateral circulation of the coronary vasculature leading to increase blood flow to ischemic areas and could be useful for the coronary artery disease (Lawson, Pharmacol. Ther., (1996) 70, 39–63, Gopalakrishnan, Drug Development Research, (1993) 28, 95–127).

U.S. Pat. No. 4,883,872 discloses bicyclic triazolopyrimidines. EP 0299727 A1, WO 90/12015, and JP 2040385 disclose bicyclic pyrazolodihydropyridines. Khim. Geterotsikl. Soedin. (1974) 6, 823-7 discloses tricyclic 4-substituted-1,2,6,7-tetrahydrodipyrazolo[3,4-b:4,3-e] pyridine-3,5-diones. Khim. Geterotsikl. Soedin. (1992) 9, 1218-22 discloses 4-phenyl 1 H-furo[3,4-b]pyrazolo[4,3-e] pyridine-3,5(2H,7H)-dione.

The compounds of the present invention are novel, hyperpolarize cell membranes, open potassium channels, relax smooth muscle cells, inhibit bladder contractions, and are useful for treating diseases that can be ameliorated by opening potassium channels.

SUMMARY OF THE INVENTION

In its principle embodiment, the present invention discloses compounds of formula I:

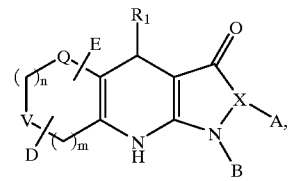

or a pharmaceutically acceptable salt, ester, amide, or prodrug thereof wherein, m is an integer 1–2;

n is an integer 0–1;

provided that when m is 2, n is 0;

$R^1$ is selected from the group consisting of aryl and heterocycle;

Q is selected from the group consisting of C(O), S(O), and $S(O)_2$;

V is selected from the group consisting of $C(R_2)(R_3)$, O, S, and $NR_4$;

$R_2$ and $R_3$ are independently absent or selected from the group consisting of hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, —$NR_5R_6$, and $(NR_5R_6)$alkyl;

$R_4$ is selected from the group consisting of hydrogen, alkenyl, alkoxy, alkoxyalkoxy, alkoxyalkyl, alkyl, alkynyl, aryl, arylalkoxy, arylalkenyl, arylalkyl, cyano, cycloalkyl, cycloalkylalkyl, haloalkoxy, haloalkyl, heterocycle, heterocyclealkyl, hydroxy, hydroxyalkyl, —$NR_5R_6$, and $(NR_5R_6)$alkyl;

$R_5$ and $R_6$ are independently selected from the group consisting of hydrogen and lower alkyl;

X is selected from the group consisting of O and N;

A is absent or selected from the group consisting of hydrogen, alkenyl, alkoxy, alkoxyalkoxy, alkoxyalkyl, alkoxycarbonyl, alkyl, alkylcarbonyl, alkylsulfonyl, alkynyl, aryl, arylalkoxy, arylalkenyl, arylalkyl, cycloalkyl, cycloalkylalkyl, haloalkoxy, haloalkyl, halogen, heterocycle, heterocyclealkyl, hydroxy, hydroxyalkyl, —$NR_5R_6$, and ($NR_5R_6$)alkyl;

B is selected from the group consisting of hydrogen, alkenyl, alkoxy, alkoxyalkoxy, alkoxyalkyl, alkoxycarbonyl, alkyl, alkylcarbonyl, alkynyl, aryl, arylalkoxy, arylalkenyl, arylalkyl, cycloalkyl, cycloalkylalkyl, haloalkoxy, haloalkyl, haloalkylcarbonyl, halogen, heterocycle, heterocyclealkyl, hydroxy, hydroxyalkyl, —$NR_5R_6$, and ($NR_5R_6$)alkyl;

or X is N and A and B together with the nitrogen atoms to which they are attached form a 5 or 6 membered ring; and D and E are independently selected from the group consisting of hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, —$NR_5R_6$, and ($NR_5R_6$)alkyl;

provided that when Q is S(O) or $S(O)_2$ and n is 0, then V is $C(R_2)(R_3)$.

DETAILED DESCRIPTION OF THE INVENTION

All patents, patent applications, and literature references cited in the specification are herein incorporated by reference in their entirety. In the case of inconsistencies, the present disclosure, including definitions, will prevail.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

In its principle embodiment, the present invention discloses compounds of formula I:

I or a pharmaceutically acceptable salt, ester, amide, or prodrug thereof wherein, m is an integer 1–2;

n is an integer 0–1;

provided that when m is 2, n is 0;

$R^1$ is selected from the group consisting of aryl and heterocycle;

Q is selected from the group consisting of C(O), S(O), and $S(O)_2$;

V is selected from the group consisting of $C(R_2)(R_3)$, O, S, and $NR_4$;

$R_2$ and $R_3$ are independently absent or selected from the group consisting of hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, —$NR_5R_6$, and ($NR_5R_6$)alkyl;

$R_4$ is selected from the group consisting of hydrogen, alkenyl, alkoxy, alkoxyalkoxy, alkoxyalkyl, alkyl, alkynyl, aryl, arylalkoxy, arylalkenyl, arylalkyl, cyano, cycloalkyl, cycloalkylalkyl, haloalkoxy, haloalkyl, heterocycle, heterocyclealkyl, hydroxy, hydroxyalkyl, —$NR_5R_6$, and ($NR_5R_6$)alkyl;

$R_5$ and $R_6$ are independently selected from the group consisting of hydrogen and lower alkyl;

X is selected from the group consisting of O and N;

A is absent or selected from the group consisting of hydrogen, alkenyl, alkoxy, alkoxyalkoxy, alkoxyalkyl, alkoxycarbonyl, alkyl, alkylcarbonyl, alkylsulfonyl, alkynyl, aryl, arylalkoxy, arylalkenyl, arylalkyl, cycloalkyl, cycloalkylalkyl, haloalkoxy, haloalkyl, halogen, heterocycle, heterocyclealkyl, hydroxy, hydroxyalkyl, —$NR_5R_6$, and ($NR_5R_6$)alkyl;

B is selected from the group consisting of hydrogen, alkenyl, alkoxy, alkoxyalkoxy, alkoxyalkyl, alkoxycarbonyl, alkyl, alkylcarbonyl, alkynyl, aryl, arylalkoxy, arylalkenyl, arylalkyl, cycloalkyl, cycloalkylalkyl, haloalkoxy, haloalkyl, haloalkylcarbonyl, halogen, heterocycle, heterocyclealkyl, hydroxy, hydroxyalkyl, —$NR_5R_6$, and ($NR_5R_6$)alkyl;

or X is N and A and B together with the nitrogen atoms to which they are attached form a 5 or 6 membered ring; and D and E are independently selected from the group consisting of hydrogen, alkenyl alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, —$NR_5R_6$, and ($NR_5R_6$)alkyl;

provided that when Q is S(O) or $S(O)_2$ and n is 0, then V is $C(R_2)(R_3)$.

In a preferred embodiment, compounds of the present invention have formula II:

II or a pharmaceutically acceptable salt, ester, amide, or prodrug thereof wherein $R_1$, V, X, A, B, D, and E are as defined in formula I.

In another preferred embodiment, compounds of the present invention have formula II wherein V is selected from O and C(R$_2$)(R$_3$); R$_2$ and R$_3$ are independently selected from hydrogen and alkyl; A is absent or selected from hydrogen, alkyl, alkylcarbonyl, alkoxycarbonyl, and aryl; B is selected from hydrogen, alkyl, and heterocycle; D and E are independently selected from hydrogen and alkyl; and R$_1$ and X are as defined in formula I.

In another preferred embodiment, compounds of the present invention have formula II wherein V is C(R)(R$_3$); and R$_1$, R$_2$, R$_3$, A, B, D, E, and X are as defined in formula I.

In another preferred embodiment, compounds of the present invention have formula II wherein X is N; V is C(R$_2$)(R$_3$); A is selected from hydrogen, alkyl, alkylcarbonyl, and alkoxycarbonyl; R$_2$, R$_3$, B, D, and E are hydrogen; and R$_1$ is as defined in formula I.

In another preferred embodiment, compounds of the present invention have formula II wherein X is N; V is C(R$_2$)(R$_3$); A is selected from hydrogen, alkyl, alkylcarbonyl, and alkoxycarbonyl; R$_2$, R$_3$, D, and E are hydrogen; B is alkyl; and R$_1$ is as defined in formula I.

In another preferred embodiment, compounds of the present invention have formula II wherein X is N; V is C(R$_2$)(R$_3$); A is selected from hydrogen, alkyl, alkylcarbonyl, and alkoxycarbonyl; R$_2$, R$_3$, and B are alkyl; D and E are hydrogen; and R$_1$ is as defined in formula I.

In another preferred embodiment, compounds of the present invention have formula II wherein X is O; V is C(R$_2$)(R$_3$); A is absent; B is alkyl; D, E, R$_2$ and R$_3$ are hydrogen; and R$_1$ is as defined in formula I.

In another preferred embodiment, compounds of the present invention have formula II wherein X is O; V is C(R$_2$)(R$_3$); A is absent; R$_2$, R$_3$, and B are alkyl; D and E are hydrogen; and R$_1$ is as defined in formula I.

In another preferred embodiment, compounds of the present invention have formula II wherein V is O; and R$_1$, A, B, D, E, and X are as defined in formula I.

In another preferred embodiment, compounds of the present invention have formula II wherein X is N; V is O; A is selected from hydrogen, alkyl, alkylcarbonyl, and alkoxycarbonyl; B is alkyl; D and E are hydrogen; and R$_1$ is as defined in formula I.

In another preferred embodiment, compounds of the present invention have formula III:

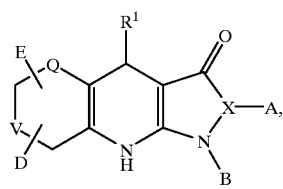

or a pharmaceutically acceptable salt, ester, amide, or prodrug thereof wherein R$_1$, Q, V, X, A, B, D, and E are as defined in formula I.

In another preferred embodiment, compounds of the present invention have formula III wherein Q is C(O); V is O; and R$_1$, A, B, D, E, and X are as defined in formula I.

In another preferred embodiment, compounds of the present invention have formula III wherein X is N; Q is C(O); V is O; A is selected from hydrogen, alkyl, alkylcarbonyl, alkoxycarbonyl, and aryl; B is selected from hydrogen, alkyl, and heterocycle; D and E are hydrogen; and R$_1$ is as defined in formula I.

In another preferred embodiment, compounds of the present invention have formula III wherein X is N; Q is C(O); V is O; A is selected from hydrogen, alkyl, alkylcarbonyl, alkoxycarbonyl, and aryl; B is alkyl; D and E are hydrogen; and R$_1$ is as defined in formula I.

In another preferred embodiment, compounds of the present invention have formula III wherein X is N; Q is C(O); V is O; A is selected from hydrogen, alkyl, alkylcarbonyl, alkoxycarbonyl, and aryl; B and D are alkyl; E is selected from hydrogen and alkyl; and R$_1$ is as defined in formula I.

In another preferred embodiment, compounds of the present invention have formula III wherein X is O; Q is C(O); V is O; A is absent; B is alkyl; D and E are hydrogen; and R$_1$ is as defined in formula I.

In another preferred embodiment, compounds of the present invention have formula IV:

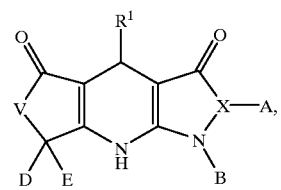

or a pharmaceutically acceptable salt, ester, amide, or prodrug thereof wherein R$_1$, V, X, A, B, D, and E are as defined in formula I.

In another preferred embodiment, compounds of the present invention have formula IV wherein V is selected from O and C(R$_2$)(R$_3$); R$_2$ and R$_3$ are independently selected from hydrogen and alkyl; A is absent or selected from hydrogen, alkyl, alkylcarbonyl, alkoxycarbonyl, and aryl; B is selected from hydrogen, alkyl, and heterocycle; D and E are hydrogen; and R$_1$ is as defined in formula I.

In another preferred embodiment, compounds of the present invention have formula IV wherein V is C(R$_2$)(R$_3$); and R$_1$, R$_2$, R$_3$, X, A, B, D, and E are as defined in formula I.

In another preferred embodiment, compounds of the present invention have formula IV wherein X is N; V is C(R$_2$)(R$_3$); R$_2$ and R$_3$ are hydrogen; A is hydrogen, alkyl, alkylcarbonyl, alkoxycarbonyl, and aryl wherein aryl is phenyl; B, D, and E are hydrogen; and R$_1$ is as defined in formula I.

In another preferred embodiment, compounds of the present invention have formula IV wherein X is N; V is C(R$_2$)(R$_3$); R$_2$ and R$_3$ are hydrogen; A is hydrogen, alkyl, alkylcarbonyl, and alkoxycarbonyl; B is alkyl; D and E are hydrogen; and R$_1$ is as defined in formula I.

In another preferred embodiment, compounds of the present invention have formula IV wherein X is N; V is C(R$_2$)(R$_3$); R$_2$ and R$_3$ are hydrogen; A is hydrogen, alkyl, alkylcarbonyl, and alkoxycarbonyl; B is heterocycle wherein heterocycle is pyridinyl; D and E are hydrogen; and R$_1$ is as defined in formula I.

In another preferred embodiment, compounds of the present invention have formula IV wherein X is O; V is C(R$_2$)(R$_3$); R$_2$ and R$_3$ are hydrogen; A is absent; B is alkyl; D and E are hydrogen; and R$_1$ is as defined in formula I.

In another preferred embodiment, compounds of the present invention have formula IV wherein V is O; and R$_1$, X, A, B, D, and E are as defined in formula I.

In another preferred embodiment, compounds of the present invention have formula IV wherein X is N; V is O; A is hydrogen, alkyl, alkylcarbonyl, and alkoxycarbonyl; B is alkyl; D and E are hydrogen; and R$_1$ is as defined in formula I.

In another preferred embodiment, compounds of the present invention have formula IV wherein X is O; V is O; A is absent; B is alkyl; D and E are hydrogen; and $R_1$ is as defined in formula I.

In another preferred embodiment, compounds of the present invention have formula V:

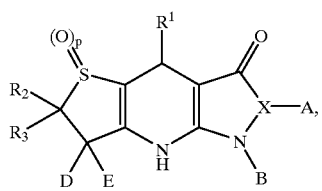

V or a pharmaceutically acceptable salt, ester, amide, or prodrug thereof, wherein p is an integer 1–2; and $R_1$, $R_2$, $R_3$, X, A, B, D, and E are as defined in formula I.

In another preferred embodiment, compounds of the present invention have formula V wherein p is an integer 1–2; $R_2$ and $R_3$ are independently selected from hydrogen and alkyl; A is absent or selected from hydrogen, alkyl, alkylcarbonyl, alkoxycarbonyl, and aryl; B is selected from hydrogen, alkyl, and heterocycle; D and E are hydrogen; and $R_1$ and X are as defined in formula I.

In another preferred embodiment, compounds of the present invention have formula V wherein p is an integer 1–2; X is N; $R_2$ and $R_3$ are hydrogen; A is selected from hydrogen, alkyl, alkylcarbonyl, and alkoxycarbonyl; B is alkyl; D and E are hydrogen; and $R_1$ is as defined in formula I.

Another embodiment of the present invention relates to pharmaceutical compositions comprising a therapeutically effective amount of a compound of formula I–V or a pharmaceutically acceptable salt, ester, amide, or prodrug thereof in combination with a pharmaceutically acceptable carrier.

Another embodiment of the invention relates to a method of treating male sexual dysfunction including, but not limited to, male erectile dysfunction and premature ejaculation, comprising administering a therapeutically effective amount of a compound of formula I–V or a pharmaceutically acceptable salt, ester, amide, or prodrug thereof.

Another embodiment of the invention relates to a method of treating female sexual dysfunction including, but not limited to, female anorgasmia, clitoral erectile insufficiency, vaginal engorgement, dyspareunia, and vaginismus comprising administering a therapeutically effective amount of a compound of formula I–V or a pharmaceutically acceptable salt, ester, amide, or prodrug thereof.

Yet another embodiment of the invention relates to a method of treating asthma, epilepsy, Raynaud's syndrome, intermittent claudication, migraine, pain, bladder overactivity, pollakiuria, bladder instability, nocturia, bladder hyperreflexia, eating disorders, urinary incontinence, enuresis, functional bowel disorders, neurodegeneration, benign prostatic hyperplasia (BPH), dysmenorrhea, premature labor, alopecia, cardioprotection, and ischemia comprising administering a therapeutically effective amount of a compound of formula I–V or a pharmaceutically acceptable salt, ester, amide, or prodrug thereof.

Definition of Terms

As used throughout this specification and the appended claims, the following terms have the following meanings.

The term "alkenyl," as used herein, refers to a straight or branched chain hydrocarbon containing from 2 to 10 carbons and containing at least one carbon—carbon double bond formed by the removal of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like.

The term "alkenyloxy," as used herein, refers to an alkenyl group, as defined herein, appended to the parent molecular moiety through an oxy group, as defined herein. Representative examples of alkenyloxy include, but are not limited to, propen-3-yloxy (allyloxy), buten-4-yloxy, and the like.

The term "alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like.

The term "alkoxyalkoxy," as used herein, refers to an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, methoxymethoxy, and the like.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, methoxymethyl, and the like.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, tert-butoxycarbonyl, and the like.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n—nonyl, n-decyl, and the like.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, 1-oxopentyl, and the like.

The term "alkylcarbonyloxy," as used herein, refers to an alkylcarbonyl group, as defined herein, appended to the parent molecular moiety through an oxy group, as defined herein. Representative examples of alkylcarbonyloxy include, but are not limited to, acetyloxy, ethylcarbonyloxy, tert-butylcarbonyloxy, and the like.

The term "alkylsulfinyl," as used herein, refers to an alkyl group, as defined herein, appended to the parent molecular moiety through a sulfinyl group, as defined herein. Representative examples of alkylsulfinyl include, but are not limited, methylsulfinyl, ethylsulfinyl, and the like.

The term "alkylsulfonyl," as used herein, refers to an alkyl group, as defined herein, appended to the parent molecular moiety through a sulfonyl group, as defined herein. Representative examples of alkylsulfonyl include, but are not limited, methylsulfonyl, ethylsulfonyl, and the like.

The term "alkylthio," as used herein, refers to an alkyl group, as defined herein, appended to the parent molecular moiety through a thio moiety, as defined herein. Representative examples of alkylthio include, but are not limited, methylthio, ethylthio, tert butylthio, hexylthio, and the like.

The term "alkynyl," as used herein, refers to a straight or branched chain hydrocarbon group containing from 2 to 10 carbon atoms and containing at least one carbon—carbon triple bond. Representative examples of alkynyl include, but are not limited, to acetylenyl, 1-propynyl, 2-propynyl, 3-butynyl, 2-pentynyl, 1-butynyl and the like.

The term "aryl," as used herein, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like.

The aryl groups of this invention can be substituted with 1, 2, 3, 4, or 5 substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halogen, haloalkyl, haloalkoxy, heterocycle, hydroxy, hydroxyalkyl, mercapto, nitro, sulfamyl, sulfo, sulfonate, —$NR_{80}R_{81}$, (wherein, $R_{80}$ and $R_{81}$ are independently selected from hydrogen, alkyl, alkylcarbonyl, aryl, arylalkyl and formyl), and —$C(O)NR_{82}R_{83}$ (wherein, $R_{82}$ and $R_{83}$ are independently selected from hydrogen, alkyl, alkylcarbonyl, aryl, arylalkyl, and formyl).

The term "arylalkenyl," as used herein, refers to an aryl group, as defined herein, appended to the parent molecular moiety through an alkenyl group, as defined herein. Representative examples of arylalkenyl include, but are not limited to, 2-phenylethenyl, 3-phenylpropen-2-yl, 2-naphth-2-ylethenyl, and the like.

The term "arylalkoxy," as used herein, refers to an aryl group, as defined herein, appended to the parent molecular moiety through analkoxy group, as defined herein. Representative examples of arylalkoxy include, but are not limited to, 2-phenylethoxy, 3-naphth-2-ylpropoxy, 5-phenylpentyloxy, and the like.

The term "arylalkoxycarbonyl," as used herein, refers to an arylalkoxy group, as defined herein, appended to the parent molecular moiety through a carbonyl group, as defined herein. Representative examples of arylalkoxy include, but are not limited to, benzyloxycarbonyl, naphth-2-ylmethoxycarbonyl, and the like.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

The term "aryloxy," as used herein, refers to an aryl group, as defined herein, appended to the parent molecular moiety through an oxy group, as defined herein. Representative examples of aryloxy include, but are not limited to, phenoxy, naphthyloxy, and the like.

The term "carbonyl," as used herein, refers to a —C(O)— group.

The term "carbony," as used herein, refers to a —$CO_2H$ group.

The term "carboxy protecting group," as used herein, refers to a carboxylic add protecting ester group employed to block or protect the carboxylic acid functionality while the reactions involving other functional sites of the compound are carried out. Carboxy-protecting groups are disclosed in T. W. Greene and P. G. M. Wuts, Protective Groups in Organic Synthesis, 3rd edition, John Wiley & Sons, New York (1999), which is hereby incorporated herein by reference. In addition, a carboxy-protecting group can be used as a prodrug whereby the carboxy-protecting group can be readily cleaved in vivo, for example by enzymatic hydrolysis, to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975), which is hereby incorporated herein by reference. Such carboxy-protecting groups are well known to those skilled in the art, having been extensively used in the protection of carboxyl groups in the penicillin and cephalosporin fields, as described in U.S. Pat. Nos. 3,840,556 and 3,719,667, the disclosures of which are hereby incorporated herein by reference. Examples of esters useful as prodrugs for compounds containing carboxyl groups can be found on pages 14–21 of "Bioreversible Carriers in Drug Design: Theory and Application", edited by E. B. Roche, Pergamon Press, New York (1987), which is hereby incorporated herein by reference. Representative carboxy-protecting groups are loweralkyl (e.g., methyl, ethyl or tertiary butyl and the like); benzyl (phenylmethyl) and substituted benzyl derivatives thereof such substituents are selected from alkoxy, alkyl, halogen, and nitro groups and the like.

The term "cyano," as used herein, refers to a —CN group.

The term "cycloalkyl," as used herein, refers to a saturated cyclic hydrocarbon group containing from 3 to 8 carbons. Representative examples of cycloalkyl include, cyclopropyl, cyclobutyl, cyclopentyl, cyclohexyl, cycloheptyl, and cyclooctyl.

The term "cycloalkylalkyl," as used herein, refers to cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl and 4-cycloheptylbutyl, and the like.

The term "formyl," as used herein, refers to a —C(O)H group.

The term "halo" or "halogen," as used herein, refers to —Cl, —Br, —I or —F.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

The term "haloalkoxy," as used herein, refers to at least one halogen, as defined herein, appended to the parent molecular moiety through an alkoxy group, as defined herein. Representative examples of haloalkoxy include, but are not limited to, 2-chloroethoxy, difluoromethoxy, 1,2-difluoroethoxy, 2,2,2-trifluoroethoxy, trifluoromethoxy, and the like.

The term "heterocycle," as used herein, refers to a monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0–2 double bonds and the 6 membered ring has from 0–3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like.

The heterocycle groups of this invention can be substituted with 1, 2,or 3 substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, arylalkoxy, arylalkoxycarbonyl, arylalkyl, aryloxy, carboxy, cyano, formyl, halogen, haloalkyl, haloalkoxy, hydroxy, hydroxyalkyl, mercapto, nitro, phenyl, sulfamyl, sulfo, sulfonate, —NR$_{80}$R$_{81}$ (wherein, R$_{80}$ and R$_{81}$ are independently selected from hydrogen, alkyl, alkylcarbonyl, aryl, arylalkyl and formyl), and —C(O)NR$_{82}$R$_{83}$ (wherein, R$_{82}$ and R$_{83}$ are independently selected from hydrogen, alkyl, aryl, and arylalkyl).

The term "heterocyclealkyl," as used herein, refers to a heterocycle, as defined herein, appended to the parent molecular moiety through an alkyl group, as defined herein. Representative examples of heterocyclealkyl include, but are not limited to, pyrid-3-ylmethyl, 2-pyrimidin-2-ylpropyl, and the like.

The term "hydroxy," as used herein, refers to an —OH group.

The term "hydroxyalkyl," as used herein, refers to a hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, and the like.

The term "lower alkyl," as used herein, is a subset of alkyl as defined herein and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like.

The term "mercapto," as used herein, refers to a —SH group.

The term "(NR$_5$R$_6$)alkyl," as used herein, refers to a —NR$_5$R$_6$ group, as defined herein, appended to the parent molecular moiety through an alkyl group, as defined herein. Representative examples of (NR$_5$R$_6$)alkyl include, but are not limited to, aminomethyl, dimethylaminomethyl, 2-(amino)ethyl, 2-(dimethylamino)ethyl, and the like.

The term "nitro," as used herein, refers to a —NO$_2$ group.

The term "nitrogen protecting group" or "N-protecting group," as used herein, refers to those groups intended to protect an amino group against undesirable reactions during synthetic procedures. N-protecting groups comprise carbamates, amides, N-benzyl derivatives, and imine derivatives. Preferred N-protecting groups are formyl, acetyl, benzoyl, pivaloyl, phenylsulfonyl, benzyl, triphenylmethyl (trityl), t-butyloxycarbonyl (Boc), benzyloxycarbonyl (Cbz). Commonly used N-protecting groups are disclosed in T. W. Greene and P. G. M. Wuts, Protective Groups in Organic Synthesis, 3rd edition, John Wiley & Sons, New York (1999).

The term "oxo," as used herein, refers to a =O moiety.

The term "oxy," as used herein, refers to a —O— moiety.

The term "sulfamyl," as used herein, refers to a —SO$_2$NR$_{94}$R$_{95}$ group, wherein, R$_{94}$ and R$_{95}$ are independently selected from hydrogen, alkyl, aryl, and aryalkyl, as defined herein.

The term "sulfinyl," as used herein, refers to a —S(O)— group.

The term "sulfo," as used herein, refers to a —SO$_3$H group.

The term "sulfonate," as used herein, refers to a —S(O)$_2$OR$_{96}$group, wherein, R$_{96}$ is selected from alkyl, aryl, and arylalkyl, as defined herein.

The term "sulfonyl," as used herein, refers to a —SO$_2$— group.

The term "thio," as used herein, refers to a —S— moiety.

The following preferred compounds may be prepared by one skilled in the art using using methodology described in the Schemes and Examples contained herein or by using methods known to those of skill in the art.

4-(3-bromo-4-fluorophenyl)-1-ethyl-4,9-dihydro-1H-isoxazolo[3,4-b]pyrano[4,3-e]pyridine-3,5(6H,8H)-dione;

4-(3-bromo-4-fluorophenyl)-1-propyl-4,9-dihydro-1H-isoxazolo[3,4b]pyrano[4,3-e]pyridine-3,5(6H,8H)-dione;

4-(3-bromo-4-fluorophenyl)-1-butyl-4,9-dihydro-1H-isoxazolo[3,4-b]pyrano[4,3-e]pyridine-3,5(6H,8H)-dione;

4-(3-bromo-4-fluorophenyl)-1-isobutyl-4,9-dihydro-1H-isoxazolo[3,4-b]pyrano[4,3-e]pyridine-3,5(6H,8H)-dione;

4-(3-bromo-4-fluorophenyl)-1-isopropyl-4,9-dihydro-1Hisoxazolo[3,4-b]pyrano[4,3-e]pyridine-3,5(6H,8H)-dione;

1-methyl-4-[4-(trifluoromethoxy)phenyl]-4,9-dihydro-1H-isoxazolo[3,4b]pyrano[4,3-e]pyridine-3,5(6H,8H)-dione;

1-methyl-4-[4-(trifluoromethoxy)phenyl]-4,7,8,9-tetrahydroisoxazolo[3,4-b]quinoline-3,5(1H,6H)-dione;

1-methyl-4-[4-(trifluoromethoxy)phenyl]-4,6,7,8-tetrahydro-1H-cyclopenta[b]isoxazolo[4,3-e]pyridine-3,5-dione;

4-[4-fluoro-3-(trifluoromethyl)phenyl]-1-methyl-4,6,7,8-tetrahydro-1H-cyclopenta[b]isoxazolo[4,3-e]pyridine-3,5-dione;

4-[4-fluoro-3-(trifluoromethyl)phenyl]-1-methyl-4,7,8,9-tetrahydroisoxazolo[3,4-b]quinoline-3,5(1H,6H)-dione;

4-(4-chloro-3-nitrophenyl)-1-methyl-4,7,8,9-tetrahydroisoxazolo[3,4-b]quinoline-3,5(1H,6H)-dione;

4-(4-chloro-3-nitrophenyl)-1-methyl-4,6,7,8-tetrahydro-1H-cyclopenta[b]isoxazolo[4,3-e]pyridine-3,5-dione;

4-(3,4-dichlorophenyl)-1-methyl-4,6,7,8-tetrahydro-1H-cyclopenta[b]isoxazolo[4,3-e]pyridine-3,5-dione;

4-(3,4-dichlorophenyl)-1-methyl-4,9-dihydro-1H-isoxazolo[3,4-b]pyrano[4,3 e]pyridine-3,5(6H,8H)-dione;

4-(3,4-dichlorophenyl)-1-methyl-4,7,8,9-tetrahydroisoxazolo[3,4-b]quinoline-3,5(1H,6H)-dione;

4-(4-fluoro-3-iodophenyl)-1-methyl-4,7,8,9-tetrahydroisoxazolo[3,4-b]quinoline-3,5(1H,6H)-dione;

4-(4-fluoro-3-iodophenyl)-1-methyl-4,6,7,8-tetrahydro-1H-cyclopenta[b]isoxazolo[4,3-e]pyridine-3,5-dione;

3-(1-methyl-3,5-dioxo-3,4,5,6,7,8-hexahydro-1H-cyclopenta[b]isoxazolo[4,3-e]pyridin-4-yl)benzonitrile;

3-(1-methyl-3,5-dioxo-1,3,4,5,6,7,8,9-octahydroisoxazolo[3,4-b]quinolin-4-yl)benzonitrile;

4-(3-bromo-4-methylphenyl)-1-methyl-4,7,8,9-tetrahydroisoxazolo[3,4b]quinoline-3,5(1H,6H)-dione;

4-(3-bromo-4-methylphenyl)-1-methyl-4,6,7,8-tetrahydro-1H-cyclopenta[b]isoxazolo[4,3-e]pyridine-3,5-dione;

4-(4-bromo-3-chlorophenyl)-1-methyl-4,6,7,8-tetrahydro-1H-cyclopenta[b]isoxazolo[4,3-e]pyridine-3,5-dione;

4-(4-bromo-3-chlorophenyl)-1-methyl-4,7,8,9-tetrahydroisoxazoto[3,4-b] quinoline-3,5(1H,6H)-dione; and 4-(4-bromo-3-chlorophenyl)-1-methyl-4,9-dihydro-1H-isoxazolo[3,4-b]pyrano[4,3-e]pyridine-3,5(6H,8H)-dione. 4-(3-bromo-4-fluorophenyl)-1,6,6-trimethyl-4,6,7,8-tetrahydro-1H-cyclopenta[b]isoxazolo[4,3-e]pyridine-3,5-dione;

4-(3-bromo-4-fluorophenyl)-1-methyl-4,8-dihydro-1H,3H-furo[3,4-b]isoxazolo[4,3-e]pyridine-3,5(7H)-dione;

4-(3-bromo-4-fluorophenyl)-1-methyl-4,6,7,8-tetrahydro-1H-isoxazolo[3,4-b]pyrrolo[3,4-e]pyridine-3,5-dione;

4-(3-bromo-4-fluorophenyl)-1,6,6-trimethyl-4,7,8,9-tetrahydroisoxazolo[3,4-b]quinoline-3,5(1H,6H)-dione;

4-(3-bromo-4-fluorophenyl)-1-methyl-4,7,8,9-tetrahydro-3H-isoxazolo[3,4 b]pyrano[3,4-e]pyridine-3,5(1H)-dione;

4-(3-bromo-4-fluorophenyl)-1-methyl-4,9-dihydro-1H-isoxazolo[3,4-b]pyrano[4,3-e]pyridine-3,5(6H,8H)-dione;

4-(3-bromo-4-fluorophenyl)-1,6,6-trimethyl-4,9-dihydro-1H-isoxazolo[3,4 b]pyrano[4,3-e]pyridine-3,5(6H,8H)-dione;

4-(3-bromo-4-fluorophenyl)-1-methyl-4,6,7,8-tetrahydroisoxazolo[3,4-b]thieno[2,3-e]pyridin-3(1H)-one 5,5-dioxide;

4-phenyl-1,6,6-trimethyl-1,2,4,9-tetrahydropyrano[3,4-b]pyrazolo[4,3-e]pyridine-3,5(6H,8H)-dione;

4-(3-bromo-4-fluorophenyl)-1,6,6-trimethyl-1,2,4,9-tetrahydropyrano[3,4-b]pyrazolo[4,3-e]pyridine-3,5(6H,8H)-dione;

4-(3-bromo-4-fluorophenyl)-1,2,6,6-tetramethyl-1,2,4,9-tetrahydropyrano[3,4 b]pyrazolo[4,3-e]pyridine-3,5(6H,8H)-dione;

2-acetyl-4-(3-bromo-4-fluorophenyl)-1,6,6-trimethyl-1,2,4,9-tetrahydropyrano[3,4 b]pyrazolo[4,3-e]pyridine-3,5(6H,8H)-dione;

4-(3-bromo-4-fluorophenyl)-2-(methoxycarbonyl)-1,6,6-trimethyl-1,2,4,9-tetrahydropyrano[3,4-b]pyrazolo[4,3-e]pyridine-3,5(6H,8H)-dione;

4-[4-(trifluoromethoxy)phenyl]-1,6,6-trimethyl-1,2,4,9-tetrahydropyrano[3,4 b]pyrazolo[4,3-e]pyridine-3,5(6H,8H)-dione;

4-(3-bromo-4-methylphenyl)-1,6,6-trimethyl-1,2,4,9-tetrahydropyrano[3,4-b]pyrazolo[4,3-e]pyridine-3,5(6H,8H1)-dione;

4-[4-fluoro3-(trifluoromethyl)phenyl]-1,6,6-trimethyl-1,2,4,9-tetrahydropyrano[3,4-b]pyrazolo[4,3-e]pyridine-3,5(6H,8H)-dione;

4-(4-chloro-3-nitrophenyl)-1,6,6-trimethyl-1,2,4,9-tetrahydropyralo[3,4-b]pyrazolo[4,3-e]pyridine-3,5(6H,8H)-dione;

4-(3-iodo-4-methylphenyl)-1,6,6-trimethyl-1,2,4,9-tetrahydropyrano[3,4-b]pyrazolo[4,3-e]pyridine-3,5(6H,8H)-dione;

4-(4-fluoro-3-iodophenyl)-1,6,6-trimethyl-1,2,4,9-tetrahydropyrano[3,4-b]pyrazolo[4,3-e]pyridine-3,5(6H,8H)-dione;

4-(3,4-dichlorophenyl)-1,6,6-trimethyl-1,2,4,9-tetrahydropyrano[3,4b]pyrazolo[4,3-e]pyridine-3,5(6H,8H)-dione;

4-[4-fluoro-3-(2-furyl)phenyl]-1,6,6-trimethyl-1,2,4,9-tetrahydropyrano[3,4 b]pyrazolo[4,3-e]pyridine-3,5(6H,8H)-dione;

4-(5-nitro-3-thienyl)-1,6,6-trimethyl-1,2,4,9-tetrahydropyrano[3,4-b]pyrazolo[4,3-e]pyridine-3,5(6H,8H)-dione;

4-(2,1,3-benzoxadiazol-5-yl)-1,6,6-trimethyl-1,2,4,9-tetrahydropyrano[3,4-b]pyrazolo[4,3-e]pyridine-3,5(6H,8H)-dione;

4-(2,1,3-benzothiadiazol-5-yl)-1,6,6-trimethyl-1,2,4,9-tetrahydropyrano[3,4 b]pyrazolo[4,3-e]pyridine-3,5(6H,8H)-dione;

4-(4-bromo-3-chloro)-1,6,6-trimethyl-1,2,4,9-tetrahydropyrano[3,4-b]pyrazolo[4,3-e]pyridine-3,5(6H,8H)-dione;

1,6,6-trimethyl-4-phenyl-1,2,4,6,7,8-hexahydrocyclopenta[b]pyrazolo[4,3-e]pyridine-3,5-dione;

4-(3-bromo-4-fluorophenyl)-1,6,6-trimethyl-1,2,4,6,7,8-hexahydrocyclopenta[b]pyrazolo[4,3-e]pyridine-3,5-dione;

4-(3-bromo-4-fluorophenyl)-1,2,6,6-tetramethyl-1,2,4,6,7,8-hexahydrocyclopenta[b]pyrazolo[4,3-e]pyridine-3,5-dione;

2-acetyl-4-(3-bromo-4-fluorophenyl)-1,6,6-trimethyl-1,2,4,6,7,8-hexahydrocyclopenta[b]pyrazolo[4,3-e]pyridine-3,5-dione;

4-(3-bromo-4-fluorophenyl)-2-(methoxycarbonyl 1,6,6-trimethyl-1,2,4,6,7,8-hexahydrocyclopenta[b]pyrazolo[4,3-e]pyridine-3,5-dione;

4-[4-(trifluoromethoxy)phenyl]-1,6,6-trimethyl-1,2,4,6,7,8-hexahydrocyclopenta[b]pyrazolo[4,3-e]pyridine-3,5-dione;

4-(3-bromo-4-methylphenyl)-1,6,6-trimethyl-1,2,4,6,7,8-hexahydrocyclopenta[b]pyrazolo[4,3-e]pyridine-3,5-dione;

4-[4-fluoro-3-(trifluoromethyl)phenyl]-1,6,6-trimethyl-1,2,4,6,7,8-hexahydrocyclopenta[b]pyrazolo[4,3-e]pyridine-3,5-dione;

4-(4-chloro-3-nitrophenyl)-1,6,6-trimethyl-1,2,4,6,7,8-hexahydrocyclopenta[b]pyrazolo[4,3-e]pyridine-3,5-dione;

4-(3-iodo-4-methylphenyl)-1,6,6-trimethyl-1,2,4,6,7,8-hexahydrocyclopenta[b]pyrazolo[4,3-e]pyridine-3,5-dione;

4-(4-fluoro-3-iodophenyl)-1,6,6-trimethyl-1,2,4,6,7,8-hexahydrocyclopenta[b]pyrazolo[4,3-e]pyridine-3,5-dione;

4-(3,4-dichlorophenyl)-1,6,6-trimethyl-1,2,4,6,7,8-hexahydrocyclopenta[b]pyrazolo[4,3-e]pyridine-3,5-dione;

4-(4-fluoro-3-(2-furyl)phenyl)-1,6,6-trimethyl-1,2,4,6,7,8-hexahydrocyclopenta[b]pyrazolo[4,3-e]pyridine-3,5-dione;

4-(5-nitro-3-thienyl)-1,6,6-trimethyl-1,2,4,6,7,8-hexahydrocyclopenta[b]pyrazolo[4,3-e]pyridine-3,5-dione;

4-(2,1,3-benzoxadiazol-5-yl)-1,6,6-trimethyl-1,2,4,6,7,8-hexahydrocyclopenta[b]pyrazolo[4,3-e]pyridine-3,5-dione;

4-(2,1,3-benzthiadiazol-5-yl)-1,6,6-trimethyl-1,2,4,6,7,8-hexahydrocyclopenta[b]pyrazolo[4,3-e]pyridine-3,5-dione; and 4-(4-bromo-3-chlorophenyl)-1,6,6-trimethyl-1,2,4,6,7,8-hexahydrocyclopenta[b]pyrazolo[4,3-e]pyridine-3,5-dione.

Most preferred compounds of the present invention include:

4-(3-bromo-4-fluorophenyl)-1-methyl 1,2,4,6,7,8-hexahydrocyclopenta[b]pyrazolo[4,3-e]pyridine-3,5-dione;

4-(3-bromo-4-fluorophenyl)-1,2,4,6,7,8-hexahydrocyclopenta[b]pyrazolo[4,3-e]pyridine-3,5-dione;

4-(3-bromo-4-fluorophenyl)-4,7,8,9-tetrahydro-1H-pyrazolo[3,4-b]quinoline 3,5(2H,6H)-dione;

4-(3-bromo-4-fluorophenyl)-1-ethyl-1,2,4,6,7,8-hexahydrocyclopenta[b]pyrazolo[4,3-e]pyridine-3,5-dione;

4-(3-bromo-4-fluorophenyl)-1-tert-butyl-1,2,4,6,7,8-hexahydrocyclopenta[b]pyrazolo[4,3-e]pyridine-3,5-dione;

4-(3-bromo-4-fluorophenyl)-1-(2-pyridinyl)-1,2,4,6,7,8-hexahydrocyclopenta[b]pyrazolo[4,3-e]pyridine-3,5-dione;

1-methyl-4-[4-(trifluoromethoxy)phenyl]-1,2,4,6,7,8-hexahydrocyclopenta[b]pyrazolo[4,3-e]pyridine-3,5-dione;

4-(3-bromo-4-methylphenyl)-1-methyl-1,2,4,6,7,8-hexahydrocyclopenta[b]pyrazolo[4,3-e]pyridine-3,5-dione;

4-[4-fluoro-3-(trifluoromethyl)phenyl]-1-methyl 1,2,4,6,7,8-hexahydrocyclopenta[b]pyrazolo[4,3-e]pyridine-3,5-dione;

4-(4-chloro-3-nitrophenyl)-1-methyl-1,2,4,6,7,8-hexahydrocyclopenta[b]pyrazolo[4,3-e]pyridine-3,5-dione;

4-(3-iodo-4-methylphenyl)-1-methyl-1,2,4,6,7,8-hexahydrocyclopenta[b]pyrazolo[4,3-e]pyridine-3,5-dione;

4-(4-fluoro-3-iodophenyl)-1-methyl-1,2,4,6,7,8-hexahydrocyclopenta[b]pyrazolo[4,3-e]pyridine-3,5-dione;

4-(3,4-dichlorophenyl)-1-methyl-1,2,4,6,7,8-hexahydrocyclopenta[b]pyrazolo[4,3-e]pyridine-3,5-dione;

4-[4-fluoro-3-(2-furyl)phenyl]-1-methyl-1,2,4,6,7,8-hexahydrocyclopenta[b]pyrazolo[4,3-e]pyridine-3,5-dione;

1-methyl-4-(5-nitro-3-thienyl)-1,2,4,6,7,8-hexahydrocyclopenta[b]pyrazolo[4,3 e]pyridine-3,5-dione;

4-(2,1,3-benzoxadiazol-5-yl)-1-methyl-1,2,4,6,7,8-hexahydrocyclopenta[b]pyrazolo[4,3-e]pyridine-3,5-dione;

4-(2,1,3-benzothiadiazol-5-yl)-1-methyl-1,2,4,6,7,8-hexahydrocyclopenta[b]pyrazolo[4,3-e]pyridine-3,5-dione;

4-(3-bromo-4-fluorophenyl)-1-methyl-4,7,8,9tetrahydro-1H-pyrazolo[3,4-b]quinoline-3,5(2H,6H)-dione;

4-(3-bromo-4-fluorophenyl)-2-methyl-1,2,4,6,7,8-hexahydrocyclopenta[b]pyrazolo[4,3-e]pyridine-3,5-dione;

4-(3-bromo-4-fluorophenyl)-2-phenyl-1,2,4,6,7,8-hexahydrocyclopenta[b]pyrazolo[4,3-e]pyridine-3,5-dione;

4-(3-bromo-4-fluorophenyl)-1-methyl 1,2,4,6,7,8-hexahydro-3H-pyrazolo[3,4-b]thieno[2,3-e]pyridin-3-one 5,5-dioxide;

4-(3-bromo-4-fluorophenyl)-1,6,6-trimethyl-4,7,8,9-tetrahydro-1H-pyrazolo[3,4-b]quinoline-3,5(2H,6H)-dione;

4-(4-fluoro-3-iodophenyl)-1,6,6-trimethyl-4,7,8,9-tetrahydro-1H-pyrazolo[3,4-b]quinoline-3,5(2H,6H)-dione;

4-(3,4-dichlorophenyl)-1,6,6-trimethyl-4,7,8,9-tetrahydro-1H-pyrazolo[3,4 b]quinoline-3,5(2H,6H)-dione;

4-[4-fluoro-3-(2-furyl)phenyl]-1,6,6-trimethyl-4,7,8,9-tetrahydro-1H-pyrazolo[3,4-b]quinoline-3,5(2H,6H)-dione;

4-(3-bromo-4-fluorophenyl)-1-methyl 1,2,4,9-tetrahydropyrano[3,4-b]pyrazolo[4,3-e]pyridine-3,5(6H,8H)-dione;

4-(3-bromo-4-fluorophenyl)-1-ethyl-1,2,4,9-tetrahydropyrano[3,4-b]pyrazolo[4,3-e]pyridine-3,5(6H,8H)-dione;

4-(4-fluoro-3-iodophenyl)-1-methyl-1,2,4,9-tetrahydropyrano[3,4-b]pyrazolo[4,3-e]pyridine-3,5(6H,8H)-dione;

4-(3-iodo-4-methylphenyl)-1-methyl-1,2,4,9-tetrahydropyrano[3,4b]pyrazolo[4,3-e]pyridine-3,5(6H,8H)-dione;

4-(4-bromo-3-chlorophenyl)-1-methyl-1,2,4,9tetrahydropyrano[3,4-b]pyrazolo[4,3-e]pyridine-3,5(6H,8H)-dione;

4-(3-bromo-4-fluorophenyl)-1-methyl 1,2,4,7,8,9-hexahydropyrano[4,3-b]pyrazolo[4,3-e]pyridine-3,5-dione;

4-(3-bromo-4-fluorophenyl)-1-methyl-4,8-dihydro-1H-furo[3,4-b]pyrazolo[4,3-e]pyridine-3,5(2H,7H)-dione;

(+) 4-(3-bromo-4-fluorophenyl)-1-methyl 1,2,4,6,7,8-hexahydrocyclopenta[b]pyrazolo[4,3-e]pyridine-3,5-dione;

(−) 4-(3-bromo-4-fluorophenyl)-1-methyl-1,2,4,6,7,8-hexahydrocyclopenta[b]pyrazolo[4,3-e]pyridine-3,5-dione;

2-acetyl-4-(3-bromo-4-fluorophenyl)-1-methyl-1,2,4,6,7,8-hexahydrocyclopenta[b]pyrazolo[4,3-e]pyridine-3,5-dione;

(−) 4-(3-bromo-4-fluorophenyl)-1,6,6-trimethyl-4,7,8,9-tetrahydro-1H-pyrazolo[3,4 b]quinoline-3,5(2H,6H)-dione;

(+) 4-(3-bromo-4-fluorophenyl)-1,6,6-trimethyl4,7,8,9-tetrahydro-1H-pyrazolo[3,4-b]quinoline-3,5(2H,6H)-dione;

2-acetyl-4-(3-bromo-4-fluorophenyl)-1,6,6-trimethyl-4,7,8,9-tetrahydro-1H-pyrazolo[3,4-b]quinoline-3,5(2H,6H)-dione;

4-(3-bromo-4-fluorophenyl)-2-(methoxycarbonyl 1-methyl-1,2,4,6,7,8-hexahydrocyclopenta[b]pyrazolo[4,3-e]pyridine-3,5-dione;

4-(4-bromo-3-chlorophenyl)-1-methyl-1,2,4,6,7,8-hexahydrocyclopenta[b]pyrazolo[4,3-e]pyridine-3,5-dione;

4-(4-bromo-3-chlorophenyl)-1,6,6-trimethyl-4,7,8,9-tetrahydro-1H-pyrazolo[3,4 b]quinoline-3,5(2H,6H)-dione;

2-acetyl-4-(3-bromo-4-fluorophenyl)-1-methyl-1,2,4,9-tetrahydropyrano[3,4-b]pyrazolo[4,3-e]pyridine-3,5(6H,8H)-dione;

4-(3-bromo-4-fluorophenyl)-1,6-dimethyl-1,2,4,9-tetrahydropyrano[3,4-b]pyrazolo[4,3-e]pyridine-3,5(6H,8H)-dione;

4-(3-bromo-4-fluorophenyl)-1,6,6-trimethyl-1,2,4,9-tetrahydropyraro[3,4-b]pyrazolo[4,3-e]pyridine-3,5(6H,8H)-dione;

4-(3-bromo-4-fluorophenyl)-1-methyl-4,9-dihydro-1H-isoxazolo[3,4-b]pyrano[4,3-e]pyridine-3,5(6H,8H)-dione;

4-(3-bromo-4-fluorophenyl)-1,6,6-trimethyl-4,7,8,9-tetrahydroisoxazolo[3,4-b]quinoline-3,5(1H,6H)-dione;

4-(3-bromo-4-fluorophenyl)-1-methyl-4,8-dihydro-1H,3H-furo[3,4-b]isoxazolo[4,3-e]pyridine-3,5(7H)-dione;

4-(3-bromo-4-fluorophenyl)-1,2-dimethyl-1,2,4,9-tetrahydropyrano[3,4-b]pyrazolo[4,3-e]pyridine-3,5(6H,8H)-dione;

4-(3-bromo-4-methylphenyl)-1-methyl-4,9-dihydro-1H-isoxazolo[3,4-b]pyrano[4,3-e]pyridine-3,5(6H,8H)-dione;

4-(2,1,3-benzoxadiazol-5-yl)-1-methyl-4,9-dihydro-1H-isoxazolo[3,4-b]pyrano[4,3-e]pyridine-3,5(6H,8H)-dione;

4-[4-fluoro-3-(trifluoromethyl)phenyl]-1-methyl-4,9-dihydro-1H-isoxazolo[3,4-b]pyrano[4,3-e]pyridine-3,5(6H,8H)-dione;

4-(4-chloro-3-nitrophenyl)-1-methyl-4,9-dihydro-1H-isoxazolo[3,4-b]pyrano[4,3-e]pyridine-3,5(6H,8H)-dione;

3-1-methyl-3,5-dioxo-3,4,5,6,8,9-hexahydro-1H-isoxazolo[3,4-b]pyrano[4,3-e]pyridin-4-yl)benzonitrile;

4-(3-bromo-4-fluorophenyl)-1-methyl-4,6,7,8-tetrahydro-1H-cyclopenta[b]isoxazolo[4,3-e]pyridine-3,5-dione;

4-(3-bromo-4-fluorophenyl)-1-methyl-4,7,8,9-tetrahydroisoxazolo[3,4-b]quinoline-3,5(1H,6H)-dione;

4-(4-fluoro-3-iodophenyl)-1-methyl-4,9-dihydro-1H-isoxazolo[3,4-b]pyrano[4,3-e]pyridine-3,5(6H,8H)-dione;

1-methyl-4-(5-nitro-3-thienyl)-4,9-dihydro-1H-isoxazolo[3,4-b]pyrano[4,3-e]pyridine-3,5(6H,8H)-dione and pharmaceutically acceptable salts, esters, amides, or prodrugs thereof.

Abbreviations

Abbreviations which have been used in the descriptions of the schemes and the examples that follow are: AcOH for acetic acid, Ac$_2$O for acetic anhydride, AIBN for 2,2'-azobis (2-methylpropionitrile), DMF for N,N-dimethylformamide, EtOAc for ethyl acetate, EtOH for ethanol, MeOH for methanol, Ms for mesylate or —OS(OCH$_3$, THF for tetrahydrofuran, and Ts for tosylate or —OS(O)$_2$-para-CH$_3$Ph)

Preparation of Compounds of the Invention

The compounds and processes of the present invention will be better understood in connection with the following synthetic schemes and methods which illustrate a means by which the compounds of the invention can be prepared.

The compounds of this invention can be prepared by a variety of synthetic routes. Representative procedures are shown in Schemes 1–28.

Scheme 1

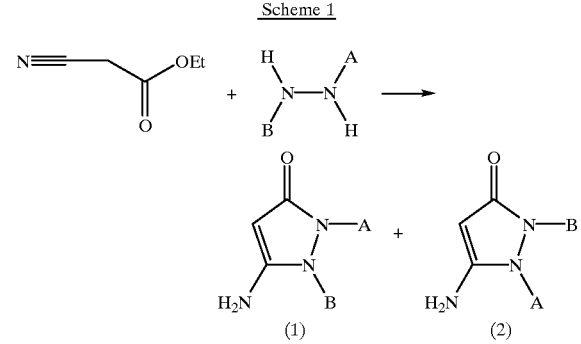

5-Amino-3-pyrazolones of general formula (1) or (2), wherein A and B are as defined in formula I, can be prepared as described in Scheme 1. Ethyl cyanoacetate can be treated with hydrazine (A and B are hydrogen), monosubstituted hydrazines (A is hydrogen or B is hydrogen), or 1,2-disubstituted hydrazines (A and B are other than hydrogen) to provide 5-amino-3-pyrazolones of general formula (1) or (2), depending on the A and B substituents. In the cases where both regioisomers are formed, as shown, chromatography can be used to separate isomers (1) from (2).

Scheme 2

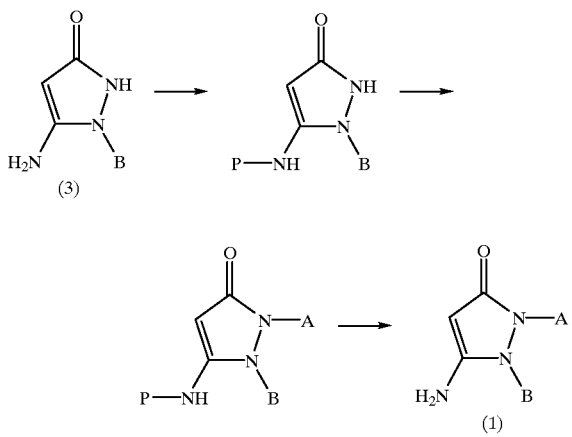

Alternatively, 1,2-disubstituted pyrazolones of general formula (1), wherein A and B are as defined in formula I, may be prepared as described in Scheme 2. Monosubstituted pyrazolones of general formula (3) can be treated with an appropriate nitrogen protecting reagent such as di-tert-butyl dicarbonate to provide 5-aminoprotected pyrazolones. 5-Aminoprotected pyrazolones can be alkylated or acylated to provide 1,2-disubstituted-5-aminoprotected pyrazolones. 5-Aminoprotected pyrazolones can be deprotected to provide 1,2-disubstituted-5-amino-3-pyrazolones of general formula (1).

Scheme 3

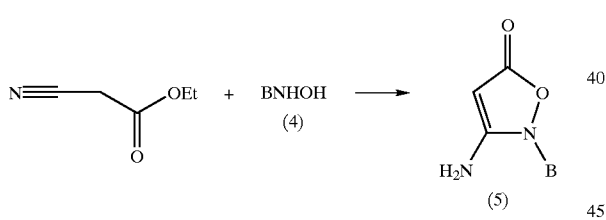

3-Amino-5(2H)-isoxazolones of general formula (5), wherein B is as defined in formula I, can be prepared as described in Scheme 3. Ethyl cyanoacetate can be treated with hydroxylamines of general formula (4) as described in (Bauer, L., Nambury, C. N. V., and Bell, C. L., Tetrahedron (1964) 20, 165171; and Barbieri, W., et al. Tetrahedron (1967) 23, 4395–4406) to provide 3-amino-5(2H)-isoxazolones of general formula (5).

Scheme 4

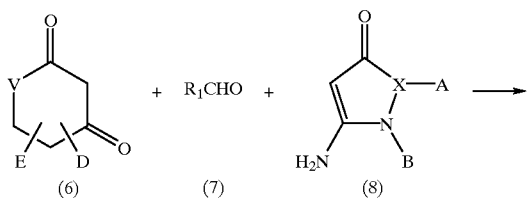

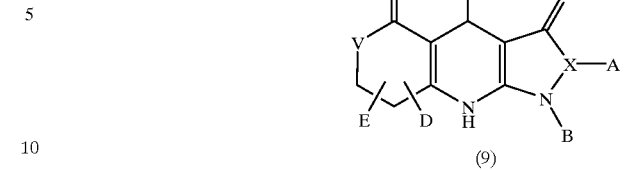

Dihydropyridines of general formula (9), wherein $R_1$, A, B, D, E, V, and X are as defined in formula I, can be prepared according to the method of Scheme 4. Dicarbonyl compounds of general formula (6) can be treated with aldehydes of general formula (7) and amino heterocycles of general formula (8), prepared as described in Schemes 1, 2, and 3 in a solvent such as ethanol, acetonitrile or dimethylformamide with heating to provide dihydropyridines of general formula (9). An additional heating step, with an acid such as HCl, may be required to drive the reaction to completion. Dicarbonyl compounds of general formula (6) may be prepared as described in (Nakagawa, S., Heterocycles 13 (1979) 477; and D'Angelo, J., Tetrahedron Letters 32 (1991) 3063).

Scheme 5

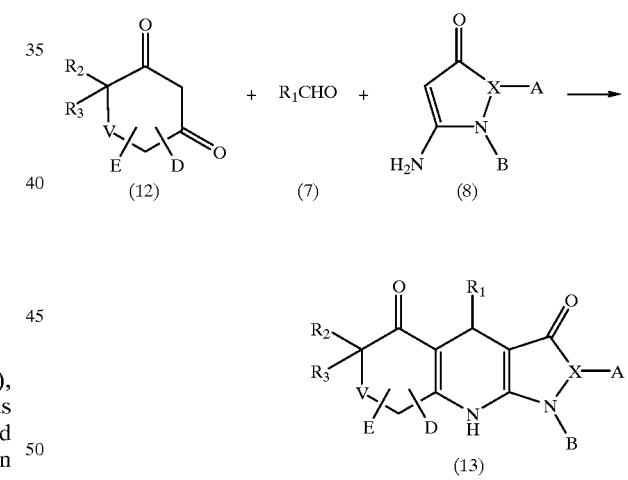

Dihydropyridines of general formula (13), wherein $R_1$, $R_2$, $R_3$, A, B, D, E, V, and X are as defined in formula I, can be prepared according to the method of Scheme 5. Dicarbonyl compounds of general formula (12), prepared as described in Scheme 6, can be treated with aldehydes of general formula (7) and amino heterocycles of general formula (8), prepared as described in Schemes 1, 2, and 3 in a solvent such as ethanol, acetonitrile or dimethylformamide with heating to provide dihydropyridines of general formula (13). An additional heating step, with an acid such as HCl, may be required to drive the reaction to completion.

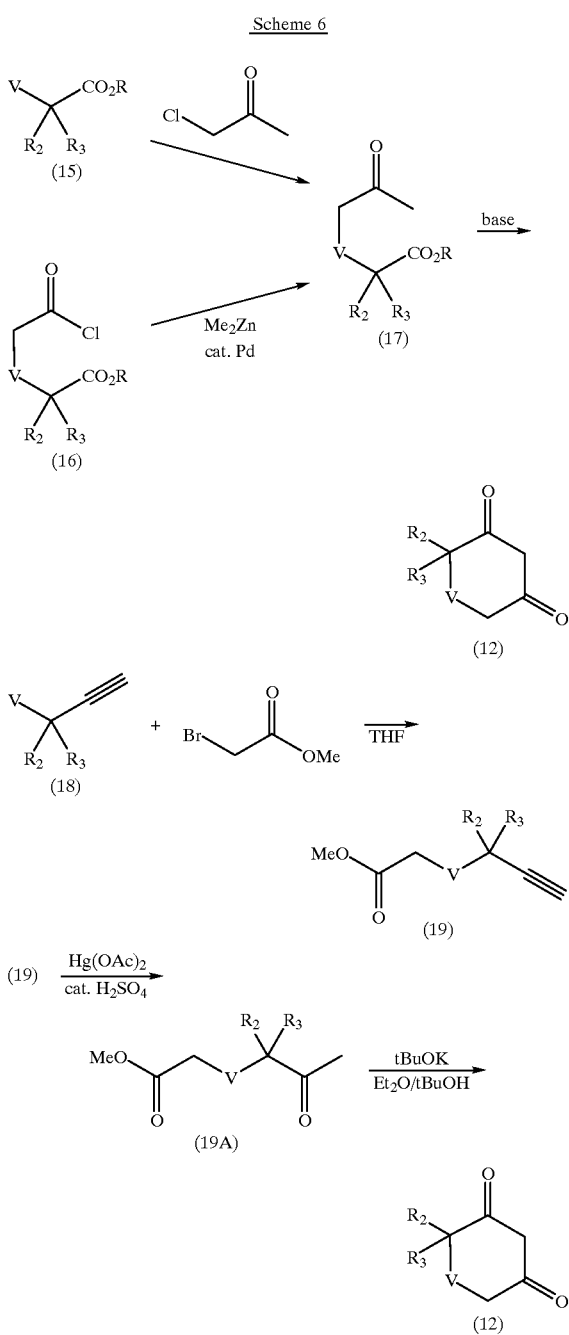

Scheme 6

An alternative method of preparing dicarbonyl compounds of general formula (12) can be used as described in Scheme 6. Alkynes of general formula (18) can be treated with methyl bromoacetate to provide ethers of general formula (19). A base such as sodium hydride may be necessary when V is O or S. Ethers of general formula (19) can be treated with a catalyst such as mercuric acetate in the presence of a catalytic amount of sulfuric acid with heating in a solvent such as methanol followed by treatment with aqueous acid to provide methyl ketones of general formula (19A). Methyl ketones of general formula (19A) can be treated with a strong base such as potassium tert-butoxide to provide dicarbonyl compounds of general formula (12).

Alkynes of general formula (18), wherein V=O, can be purchased or prepared by reaction of a nucleophilic source of acetylene such a ethynylmagnesium bromide with an appropriate ketone or aldehyde.

Chiral alkynes of general formula (18), wherein V=O, can also be purchased or generated by known methods (Midland, M. Tetrahedron (1984), 40, 1371–1380; Smith, R. J.Med.Chem. (1988), 31, 1558–1566) and then processed to provide chiral dicarbonyl compounds of general formula (12).

Dicarbonyl compounds of general formula (12) may also be prepared using the procedures described in (Ziegler, J. Amer. Chem. Soc. (1973), 95, 7458–7464; and Terasawa, T., Journal of Organic Chemistry 42 (1977) 1163).

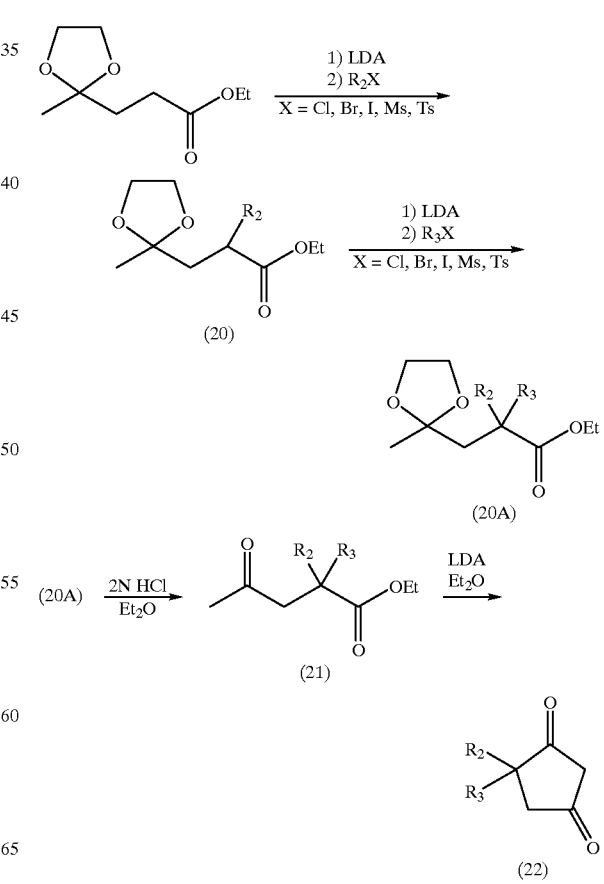

Scheme 7

Dicarbonyl compounds of general formula (12), wherein $R_2$, $R_3$, and V are as defined in formula I, can be prepared as described in Scheme 6. Esters of general formula (15), wherein V is selected from S or $NR_4$ and $R_4$ is as defined in formula I, can be alkylated with chloroacetone to provide ketoesters of general formula (17). Ketoesters of general formula (17) can cyclize in the presence of a base such as potassium tertbutoxide to provide dicarbonyl compounds of general formula (12). An alternative method of preparing ketoesters of general formula (17) can also be used. Acid chlorides of general formula (16), wherein V is O, prepared as described in (Terasawa, J. Org. Chem. (1977), 42, 1163–1169) can be treated with dimethyl zinc in the presence of a palladium catalyst to provide ketoesters of general formula (17).

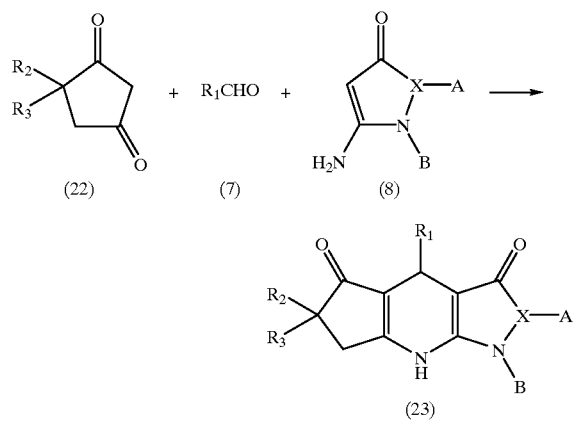

Dihydropyridines of general formula (23), wherein $R_1$, $R_2$, $R_3$, A, B, and X are as defined in formula I, can be prepared according to the method of Scheme 7. Dicarbonyl compounds of general formula (22) can be prepared as described in (Suihara, Y. Et al, JACS (1985) 107, 5894–5897). Ethyl 3-(2-methyl-1,3-dioxolan-2-yl)propanoate can be treated with a strong base such as lithium diisopropylamine and an electrophile to provide esters of general formula (20). Esters of general formula (20) can be treated again with the same alkylating conditions to provide esters of general formula (20A). Esters (20) or (20A) can be hydrolized under mild acid conditions and the resultant keto ester treated with strong base such as lithium diisopropylamine to provide dicarbonyl compounds of general formula (22). Dicarbonyl compounds of general formula (22) can be treated with aldehydes of general formula (7) and amino heterocycles of general formula (8), prepared as described in Schemes 1, 2, and 3 in a solvent such as ethanol, acetonitrile or dimethylformamide with heating to provide dihydropyridines of general formula (23).

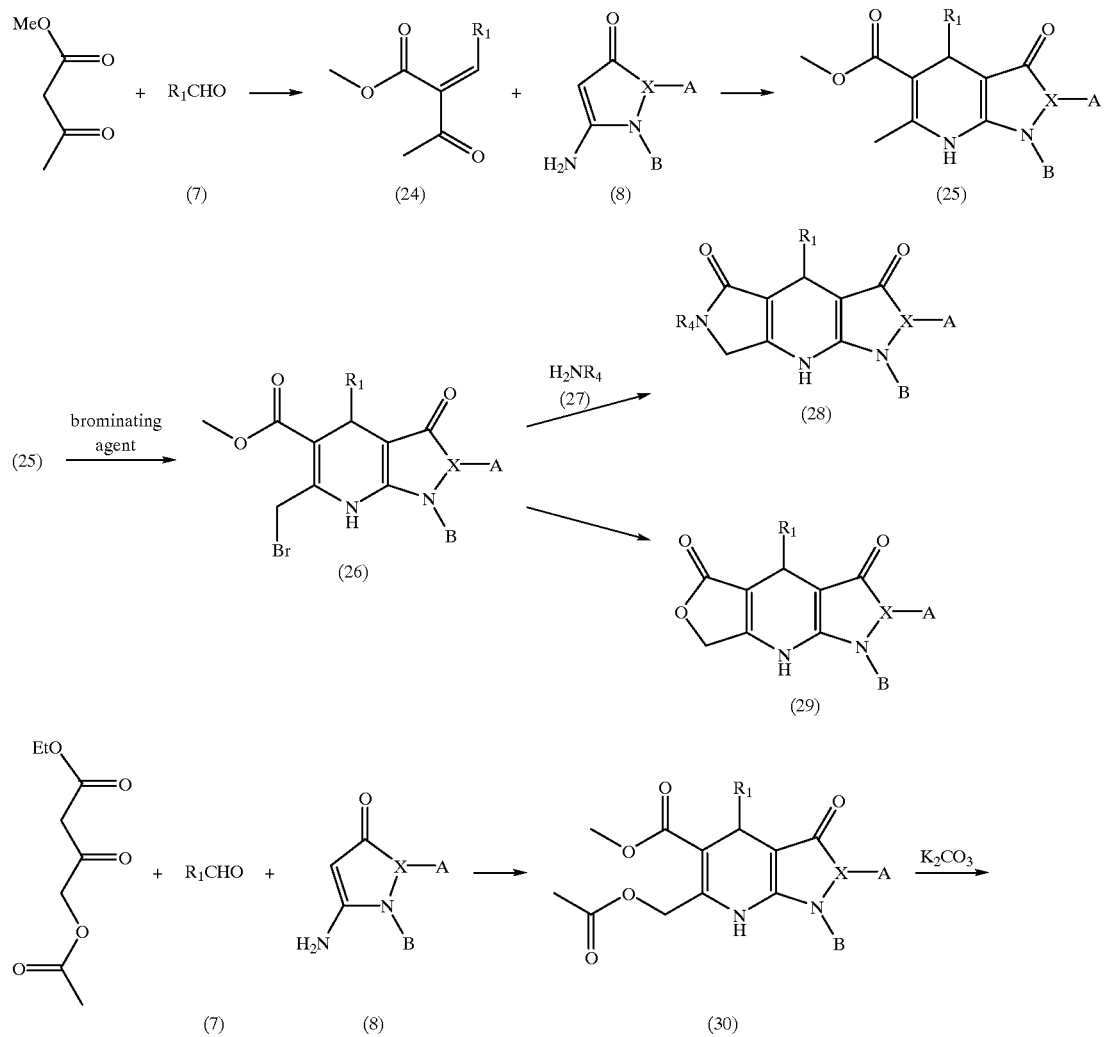

Scheme 8

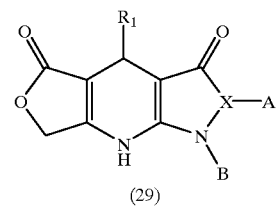

(29)

Dihydropyridines of general formula (28) and (29), wherein A, B, X, $R_1$, and $R_4$ are as defined in formula I, can be prepared as described in Scheme 8 Methyl acetoacetate can be condensed with aldehydes (7) to provide α,β-unsaturated ketones of general formula (24). α,β-Unsaturated ketones of general formula (24) can be treated with amino heterocycles of general formula (8), prepared as described in Schemes 1, 2, and 3 to provide dihydropyridnes of general formula (25). Dihydropyridines of general formula (25) can be treated with brominating agents such as N-bromosuccinimide or pyridinium tribromide in a solvent such as methanol, ethanol, isopropanol, or chloroform to provide dihydropyridines of general formula (26). Dihydropyridines of general formula (26) can be treated with primary amines of general formula (27) or ammonia with heat in a solvent such as ethanol to provide dihydropyridines of general formula (28). Dihydropyridines of general formula (26) can be heated neat or in a solvent such as chloroform to provide dihydropyridines of general formula (29).

An alternative and more preferred method of preparing dihydropyridines of general formula (29) can be used as described in Scheme 8. Ethyl 4(acetyloxy)-3-oxobutanoate prepared as described in (S. Husband, W. Fraser, C. J. Suckling, H. C. Wood, Tetrahedron, (1995) 51(3), 865), can be treated with aldehydes of general formula (7) and amino heterocycles of general formula (8) with heat in an alcoholic solvent such as ethanol to provide dihydropyridines of general formula (30). Dihydropyridines of general formula (30) can be treated with potassium carbonate in methanol to provide dihydropyridines of general formula (29).

Scheme 9

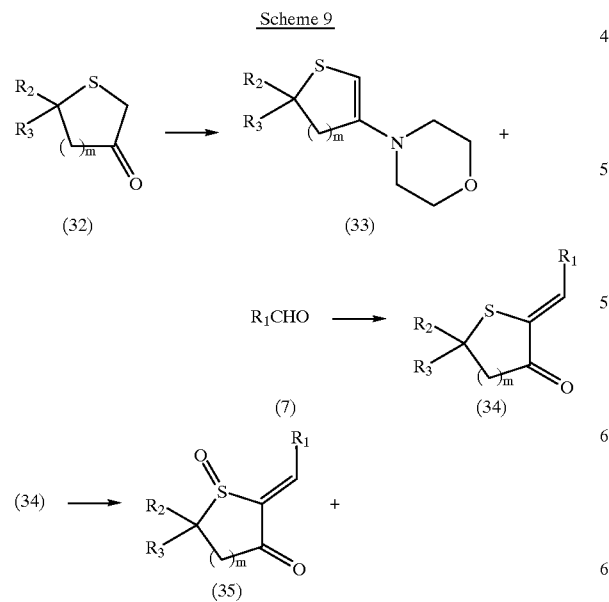

Dihydropyridines of general formula (36), wherein A, B, X, $R_2$, $R_3$, and m are as defined in formula I, can be prepared as described in Scheme 9. β-Keto sulfides of general formula (32) can be treated with secondary amines such as morpholine, pyrrolidine or piperidine to provide enamines of general formula (33) which can be condensed with aldehydes (7) in an appropriate organic solvent to provide sulfides of general formula (34). Sulfides of general formula (34) can be oxidized with an oxidant such as meta-chloroperoxybenzoic acid to sulfoxides of general formula (35). Sulfoxides of general formula (35) can be treated with amino heterocycles of general formula (8), prepared as described in Schemes 1, 2, and 3 with heating in a solvent such as ethyl alcohol or similar alcoholic solvent, acetonitrile or dimethylformamide to provide dihydropyridines of general formula (36).

Scheme 10

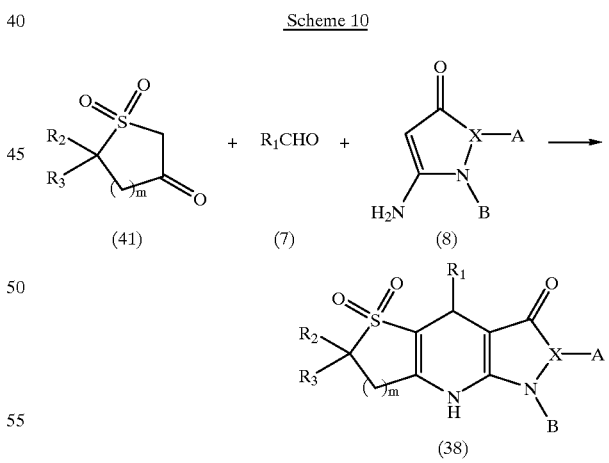

Dihydropyridines of general formula (38), wherein $R_1$, $R_2$, $R_3$, A, B, and m are as defined in formula I, can be prepared according to the method of Scheme 10. Ketosulfones of general formula (41), prepared as described in Scheme 11, can be treated with aldehydes of general formula (7) and amino heterocycles of general formula (8), prepared as described in Schemes 1, 2, and 3 in a solvent such as ethanol, acetonitrile or dimethylformamide with heating to provide dihydropyridines of general formula (38).

Scheme 11

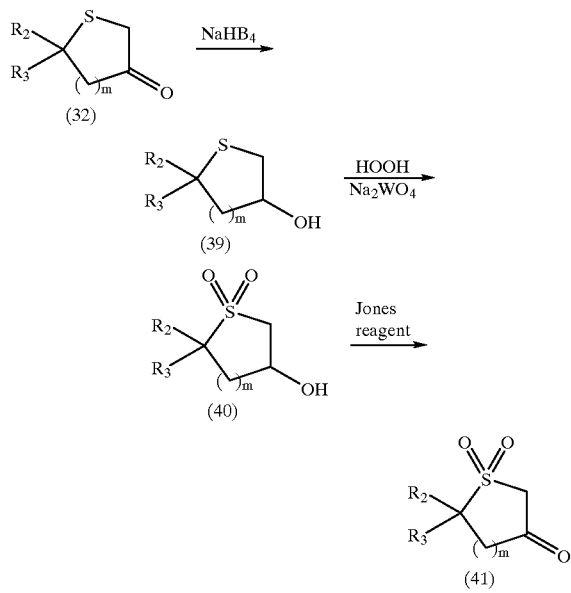

Ketosulfones of general formula (41), wherein $R_2$, $R_3$, and m are as defined in formula I, can be prepared as described in Scheme 1. Reduction of ketone (32) with sodium borohydride (or the like) in a solvent such as ethanol provides alcohols of general formula (39) which can be oxidized to the corresponding sulfones of general formula (40) using an oxidizing agent such as hydrogen peroxide catalyzed by sodium tungstate. Further oxidation of (40) using Jones reagent or the like provides ketosulfones of general formula (41).

Many of the starting aryl and heteroaryl aldehydes necessary to carry out the methods described in the preceeding and following Schemes may be purchased from commercial sources or may be synthesized by known procedures found in the chemical literature. Appropriate literature references for the preparation of aryl and heteroaryl aldehydes may be found in the following section or in the Examples. For starting materials not previously described in the literature the following Schemes are intended to illustrate their preparation through a general method.

The preparation of aldehydes used to synthesize many preferred compounds of the invention may be found in the following literature references: Pearson, Org. Synth. Coll. Vol V (1973), 117; Nwaukwa, Tetrahedron Lett. (1982), 23, 3131; Badder, J. Indian Chem. Soc. (1976), 53, 1053; Khanna, J. Med. Chem. (1997), 40, 1634; Rinkes, Recl. Trav. Chim. Pays-Bas (1945), 64, 205; van der Lee, Recl. Trav. Chim. Pays-Bas (1926), 45, 687; Widman, Chem. Ber. (1882), 15, 167;Hodgson, J. Chem. Soc. (1927), 2425; Clark, J. Fluorine Chem. (1990), 50, 411;Hodgson, J. Chem. Soc. (1929), 1635; Duff, J. Chem. Soc. (1951), 1512; Crawford, J. Chem. Soc. (1956), 2155; Tanouchi, J. Med. Chem. (1981), 24, 1149; Bergmann, J. Am. Chem. Soc. (1959), 81, 5641; Other: Eistert, Chem. Ber. (1964), 97, 1470; Sekikawa, Bull. Chem. Soc. Jpn. (1959), 32, 551.

Scheme 12

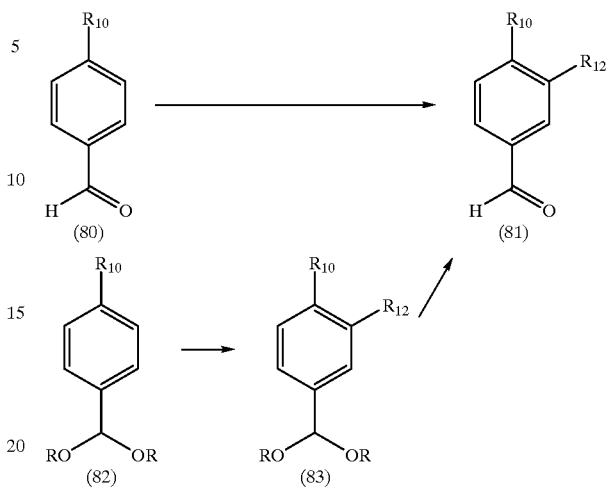

Meta, para-disubstituted aldehydes of general formula (81), wherein $R_{10}$ is selected from alkyl, haloalkyl, halogen, haloalkoxy, alkoxy, alkylthio, —$NZ_1Z_2$, and —$C(O)NZ_1Z_2$, wherein $Z_1$ and $Z_2$ are independently selected from hydrogen, alkyl, alkylcarbonyl, aryl, arylalkyl, and formyl and $R_{12}$ is selected from nitro, halogen, and alkylcarbonyl, can be prepared according to the method described in Scheme 12. A para substituted aldehyde of general formula (80) or the corresponding acetal protected aldehyde of general formula (82), wherein R is selected from alkyl or together with the oxygen atoms to which they are attached form a 5 or 6 membered ring wherein 1,3-dioxolanes are preferred, may by subjected to conditions of an electrophilic aromatic substitution reaction to provide aldehydes of general formula (81) or protected aldehydes of general formula (83). Preferred protecting groups for compounds of general formula (82) and (83) include dimethyl or diethyl acetals or the 1,3-dioxolanes. These protecting groups can be introduced at the beginning and removed at the end to provide substituted aldehydes of general formula (81) using methods well known to those skilled in the art of organic chemistry.

Scheme 13

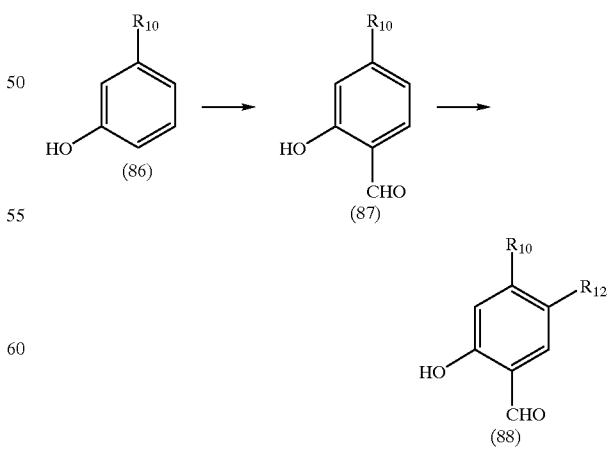

Aldehydes of general formula (88), wherein $R_{10}$ is selected from alkyl, haloalkyl, halo, haloalkoxy, alkoxy, alkylthio, —NZ$_1$Z$_2$, and —C(O)NZ$_1$Z$_2$, wherein Z$_1$ and Z$_2$ are independently selected from hydrogen, alkyl, alkylcarbonyl, aryl, arylalkyl, and formyl and R$_{12}$ is selected from nitro, halogen, and alkylcarbonyl, can be prepared by the method described in Scheme 13. A meta substituted phenol (86) is converted to the para substituted salicylaldehyde (87) by reaction with a base such as sodium hydroxide and a reagent such as trichloromethane or tribromomethane, known as the Reimer-Tiemann reaction. An alternate set of reaction conditions involves reaction with magnesium methoxide and paraformaldehyde (Aldred, J. Chem. Soc. Perkin Trans. 1 (1994), 1823). The aldehyde (87) may be subjected to conditions of an electrophilic aromatic substitution reaction to provide meta, para disubstituted salicylaldehydes of general formula (88).

Scheme 14

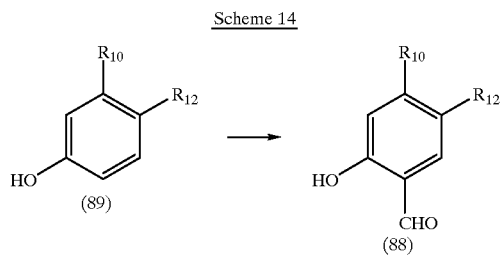

An alternative method of preparing meta, para disubstituted salicylaldehydes of general formula (88), wherein R$_{10}$ is selected from alkyl, haloalkyl, halo, haloalkoxy, alkoxy, alkylthio, —NZ$_1$Z$_2$, and —C(O)NZ$_1$Z$_2$, wherein Z$_1$ and Z$_2$ are independently selected from hydrogen, alkyl, alkylcarbonyl, aryl, arylalkyl, and formyl and R$_{12}$ is selected from nitro, halo, and alkylcarbonyl, can be used as described in Scheme 14. A meta, para disubstituted phenol of general formula (89) can be reacted with a base such as sodium hydroxide and a reagent such as trichloromethane or tribromomethane, known as the Reimer-Tiemann reaction, to provide disubstituted salicylaldehydes of general formula (88). An alternate set of reaction conditions involves reaction with magnesium methoxide and paraformaldehyde (Aldred, J. Chem. Soc. Perkin Trans. 1 (1994), 1823).

Scheme 15

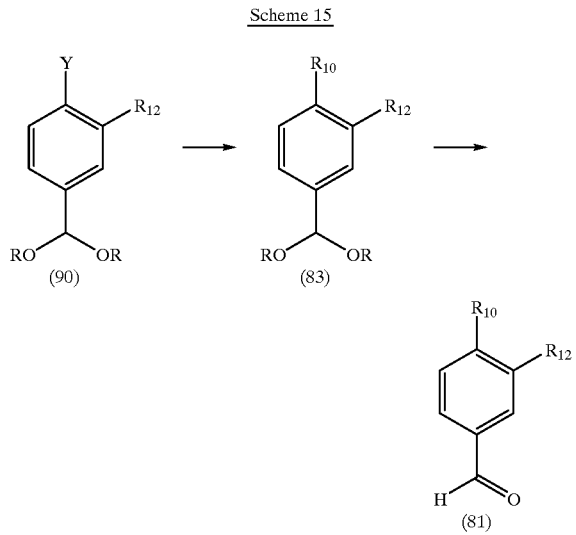

An alternative method of preparing benzaldehydes of general formula (81), wherein R$_{12}$ is selected from alkyl, haloalkyl, chlorine, fluorine, haloalkoxy, alkoxy, alkylthio, nitro, alkylcarbonyl, arylcarbonyl, —NZ$_1$Z$_2$, and —C(O)NZ$_1$Z$_2$, wherein Z$_1$ and Z$_2$ are independently selected from hydrogen, alkyl, alkylcarbonyl, aryl, arylalkyl, and formyl, and R$_{10}$ is selected from alkyl, hydroxyalkyl, alkylthio, alkylcarbonyl, and formyl, is described in Scheme 15. Protected benzaldehydes of general formula (90), wherein Y is selected from bromine or iodine and wherein R is selected from alkyl or together with the oxygen atoms to which they are attached form a 5 or 6 membered ring wherein 1,3-dioxolanes are preferred, can be converted to 3,4-disubstituted protected benzaldehydes of general formula (83) via conversion to an intermediate lithio or magnesio derivative, followed by reaction with an appropriate electrophile such as an aldehyde, dialkyldisulfide, a Weinreb amide, dimethylformamide, an alkyl halide or other electrophile followed by deprotection of the acetal to provide benzaldehydes of general formula (81).

An alternative method of preparing benzaldehydes of general formula (81), wherein R$_{12}$ is selected from alkyl, alkylcarbonyl, alkylsulfonyl, aryl, heteroaryl, cyano, haloalkyl, chlorine, fluorine, haloalkoxy, nitro, alkoxy, and alkylthio, and —C(O)NZ$_1$Z$_2$, wherein and Z$_2$ are independently selected from hydrogen, alkyl, alkylcarbonyl, aryl, arylalkyl, and formyl, and R$_{10}$ is selected from alkyl, alkynyl, vinyl, aryl, heteroaryl, cyano and the like, is also described in Scheme 15. Protected benzaldehydes of general formula (90), wherein Y is selected from bromine, iodine, or triflate, and wherein R is selected from alkyl or together with the oxygen atoms to which they are attached form a 5 or 6 membered ring wherein 1,3-dioxolanes are preferred, can be treated with suitable tin, boronic acid, alkyne, or unsaturated halide reagents in the presence of a catalyst such as a palladium catalyst with heating in a solvent such as dimethylformamide to effect a coupling reaction that provides protected benzaldehydes of general formula (83). Deprotection of the acetal of general formula (83) provides benzaldehydes of general formula (81).

Scheme 16

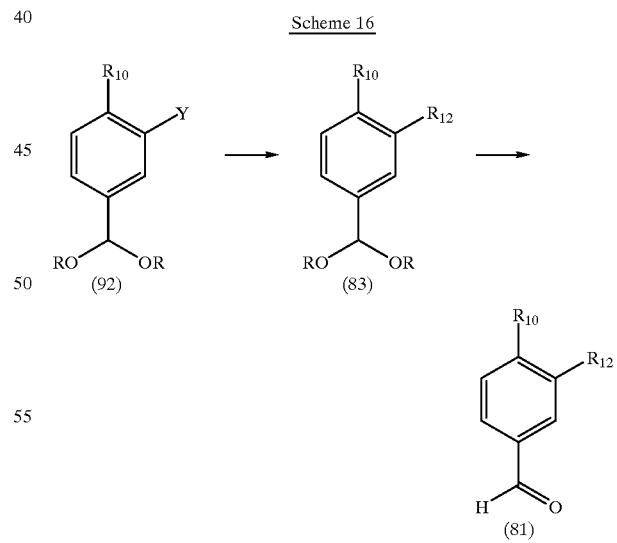

An alternative method of preparing benzaldehydes of general formula (81), wherein R$_{10}$ is selected from alkyl, haloalkyl, chlorine, fluorine, haloalkoxy, alkoxy, alkylthio, —NZ$_1$Z$_2$, and —C(O)NZ$_1$Z$_2$, wherein Z$_1$ and Z$_2$ are independently selected from hydrogen, alkyl, alkylcarbonyl, aryl, arylalkyl, and formyl, R$_{12}$ is selected from alkyl, hydroxyalkyl, alkylthio, alkylcarbonyl, arylcarbonyl, and formyl, can be used as described in Scheme 16. Protected benzaldehydes of general formula (92), wherein Y is selected from bromine or iodine, and wherein R is selected from alkyl or together with the oxygen atoms to which they are attached form a 5 or 6 membered ring wherein 1,3-dioxolanes are preferred can be converted to 3,4-disubstituted protected benzaldehydes of general formula (83) via conversion to an intermediate lithio or magnesio derivative, followed by reaction with an appropriate electrophile such as an aldehyde, dialkyldisulfide, a Weinreb amide, dimethylformamide, an alkyl halide or other electrophile followed by deprotection of the acetal to provide benzaldehydes of general formula (81).

An alternative method of preparing benzaldehydes of general formula (81), wherein $R_{10}$ is selected from alkyl, alkylcarbonyl, alkylsulfonyl, aryl, heteroaryl, cyano, haloalkyl, chlorine, fluorine, haloalkoxy, nitro, alkoxy, and alkylthio, and —C(O)NZ$_1$Z$_2$, wherein Z$_1$ and Z$_2$ are independently selected from hydrogen, alkyl, alkylcarbonyl, aryl, arylalkyl, and formyl, and $R_{12}$ is selected from alkyl, alkynyl, vinyl, aryl, heteroaryl, cyano and the like, is also described in Scheme 16. Protected benzaldehydes of general formula (92), wherein Y is selected from bromine, iodine, or triflate, and wherein R is selected from alkyl or together with the oxygen atoms to which they are attached form a 5 or 6 membered ring wherein 1,3-dioxolanes are preferred, can be treated with suitable tin, boronic acid, alkyne, or unsaturated halide reagents in the presence of a catalyst such as a palladium catalyst with heating in a solvent such as dimethylformamide to effect a coupling reaction that provides protected benzaldehydes of general formula (83). Deprotection of the acetals of general formula (83) provides benzaldehydes of general formula (81).

Scheme 17

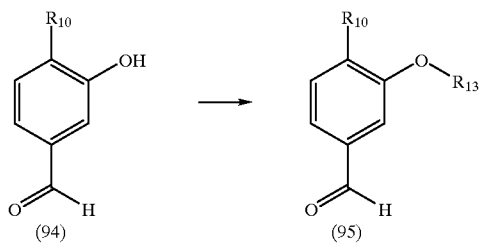

(94)                    (95)

Benzaldehydes of general formula (95), wherein $R_{10}$ is selected from hydrogen, alkyl, alkylsulfonyl, aryl, heteroaryl, cyano, haloalkyl, halo, haloalkoxy, nitro, alkoxy, alkylthio, —NZ$_1$Z$_2$, and —C(O)NZ$_1$Z$_2$, wherein Z$_1$ and Z$_2$ are independently selected from hydrogen, alkyl, alkylcarbonyl, aryl, arylalkyl, and formyl, and $R_{13}$ is selected from alkyl, arylalkyl, and haloalkyl wherein preferred haloalkyl groups are selected from difluoromethyl, 2,2,2-trifluoroethyl and bromodifluoromethyl, can be prepared as described in Scheme 17. 3-Hydroxybenzaldehyde of general formula (94) can be treated with suitable alkylating reagents such as benzylbromide, iodomethane, 2-iodo-1,1,1-trifluoroethane, chlorodifluoromethane, or dibromodifluoromethane in the presence of base such as potassium carbonate, potassium tert-butoxide or sodium tert-butoxide, to provide benzaldehydes of general formula (95). The synthesis of useful 3-hydroxybenzaldehydes of general formula (94) may be found in the following literature references: J. Chem. Soc. (1923), 2820; J. Med Chem. (1986), 29, 1982; Monatsh. Chem. (1963), 94, 1262; Justus Liebigs Ann. Chem. (1897), 294, 381; J. Chem. Soc. Perkin Trans. 1 (1990), 315; Tetrahedron Lett. (1990), 5495; J. Chem. Soc. Perkin Trans. 1 (1981), 2677.

Scheme 18

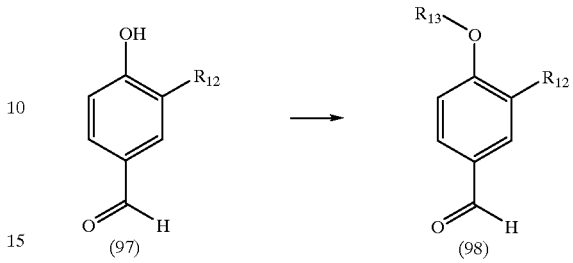

(97)                    (98)

Benzaldehydes of general formula (98), wherein $R_{12}$ is selected from hydrogen, alkyl, alkylsulfonyl, aryl, heteroaryl, cyano, haloalkyl, halo, haloalkoxy, nitro, alkoxy, alkylthio, —NZ$_1$Z$_2$, and —C(O)NZ$_1$Z$_2$, wherein Z$_1$ and Z$_2$ are independently selected from hydrogen, alkyl, alkylcarbonyl, aryl, arylalkyl, and formyl, and $R_{13}$ is selected from alkyl, arylalkyl, and haloalkyl wherein preferred haloalkyl groups are selected from difluoromethyl, 2,2,2-trifluoroethyl, and bromodifluoromethyl, can be prepared as described in Scheme 18. 4-Hydroxybenzaldehydes of general formula (97) can be treated with suitable alkylating reagents such as benzylbromide, iodomethane, 2-iodo-1,1,1-trifluoroethane, chlorodifluoromethane, or dibromodifluoromethane, in the presence of base such as potassium carbonate, potassium tert-butoxide or sodium tert-butoxide to provide benzaldehydes of general formula (98). The synthesis of useful 4-hydroxybenzaldehydes of general formula (97) may be found in the following literature references: Angyal, J. Chem. Soc. (1950), 2141; Ginsburg, J. Am. Chem. Soc. (1951), 73, 702; Claisen, Justus Liebigs Ann. Chem. (1913), 401, 107; Nagao, Tetrahedron Lett. (1980), 21, 4931; Ferguson, J. Am. Chem. Soc. (1950), 72, 4324; Barnes, J. Chem. Soc. (1950), 2824; Villagomez-Ibarra, Tetrahedron (1995), 51, 9285; Komiyama, J. Am. Chem. Soc. (1983), 105, 2018; DE 87255;Hodgson, J. Chem. Soc. (1929), 469;Hodgson, J. Chem. Soc. (1929), 1641.

Scheme 19

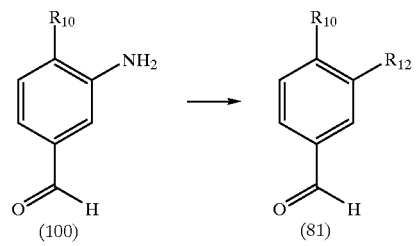

(100)                    (81)

An alternate method for introduction of substituents at the 3-position of benzaldehydes of general formula (81), wherein $R_{10}$ is selected from hydrogen, alkyl, alkylsulfonyl, aryl, heteroaryl, cyano, haloalkyl, halo, haloalkoxy, nitro, alkoxy, alkylthio, and —C(O)NZ$_1$Z$_2$, wherein Z$_1$ and Z$_2$ are independently selected from hydrogen, alkyl, alkylcarbonyl, aryl, arylalkyl, and formyl can be used as described in Scheme 19. This method, also known as the Sandmeyer reaction, involves converting 3-amino benzaldehydes of general formula (100) to an intermediate diazonium salt with sodium nitrite. The diazonium salts can be treated with a bromine or iodine source to provide the bromide or iodide. The Sandmeyer reaction and conditions for effecting the transformation are well known to those skilled in the art of organic chemistry. The types of $R_{12}$ substituents that may be introduced in this fashion include cyano, hydroxy, or halo. In order to successfully carry out this transformation it may in certain circumstances be advantageous to perform the Sandmeyer reaction on a protected aldehyde.

The resulting iodide or bromide can then be treated with unsaturated halides, boronic acids or tin reagents in the presence of a palladium catalyst such as tetrakis (triphenylphosphine)palladium (0) to provide benzaldehydes of general formula (81). The diazonium salts can also be treated directly with unsaturated halides, boronic acids or tin reagents in the presence of a palladium catalyst such as tetrakis(triphenylphosphine)palladium (0) to provide benzaldehydes of general formula (81).

Scheme 20

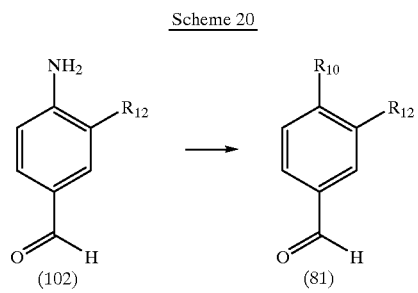

An alternate method for introduction of substituents at the 4-position of benzaldehydes of general formula (81), wherein $R_{12}$ is selected from hydrogen, alkyl, alkylsulfonyl, aryl, heteroaryl, cyano, haloalkyl, halo, haloalkoxy, nitro, alkoxy, alkylthio, and —C(O)NZ$_1$Z$_2$, wherein Z$_1$ and Z$_2$ are independently selected from hydrogen, alkyl, alkylcarbonyl, aryl, arylalkyl, and formyl, can be used as described in Scheme 20. This method, also known as the Sandmeyer reaction, involves converting 4-amino benzaldehydes of general formula (102) to an intermediate diazonium salt with sodium nitrite and then treating the diazonium salts in a similar manner as that described in Scheme 19. The types of $R_{10}$ substituents that may be introduced in this fashion include cyano, hydroxy, or halo. The Sandmeyer reaction and conditions for effecting the transformation are well known to those skilled in the art of organic chemistry. In order to successfully carry out this transformation it may in certain circumstances be advantageous to perform the Sandmeyer reaction on a protected aldehyde.

Scheme 21

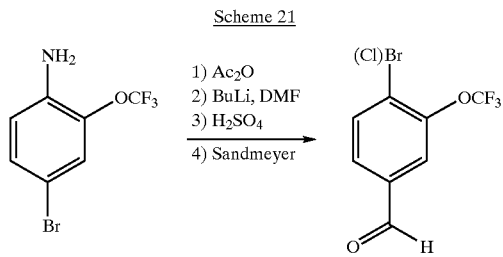

4-Bromo-3-(trifluoromethoxy)benzaldehyde or 4-chloro-3-(trifluoromethoxy)benzaldehyde can be prepared as described in Scheme 21. The commercially available 4-bromo-2-(trifluoromethoxy)aniline can be protected on the amino group with a suitable N-protecting group well known to those skilled in the art of organic chemistry such as acetyl or tert-butoxycarbonyl. The bromine can then be converted to the lithio or magnesio derivative and reacted directly with dimethylformamide to provide the 4-aminoprotected-3-(trifluoromethoxy)benzaldehyde derivative. Removal of the N-protecting group followed by conversion of the amine to a bromide or chloride via the Sandmeyer method of Scheme 19 followed by hydrolysis of the dioxolane provides 4bromo-3-(trifluoromethoxy) benzaldehyde or 4-chloro-3-(trifluoromethoxy) benzaldehyde.

Scheme 22

4-Trifluoromethylbenzaldehydes of general formula (105), wherein Y is selected from cyano, nitro, and halo may be prepared according to the method of Scheme 22. 4-Trifluoromethylbenzoic acid is first nitrated, using suitable conditions well known in the literature such as nitric acid with sulfuric acid, and the carboxylic acid group reduced with borane to provide 3-nitro-4-trifluoromethylbenzyl alcohol. From this benzyl alcohol may be obtained the 3-nitro-4-trifluoromethylbenzaldehyde by oxidation with typical reagents such as manganese dioxide. The nitro benzylic alcohol can be reduced to the aniline using any of a number of different conditions for effecting this transformation among which a preferred method is hydrogenation over a palladium catalyst. The aniline can be converted to either a halo or cyano substituent using the Sandmeyer reaction described in Scheme 19. Benzyl alcohols of general formula (104) can be oxidized using conditions well known to those skilled in the art such as manganese dioxide or Swern conditions to provide benzaldehydes of general formula (105).

For certain aromatic ring substitutions of $R_1$ for compounds of the present invention it is preferable to effect transformations of the aromatic ring substitutions after the aldehyde has been incorporated into the core structure of the present invention. As such, compounds of the present invention may be further transformed to other distinct compounds of the present invention. These transformations involve Stille, Suzuki and Heck coupling reactions all of which are well known to those skilled in the art of organic chemistry. Shown below are some representative methods of such transformations of compounds of the present invention to other compounds of the present invention.

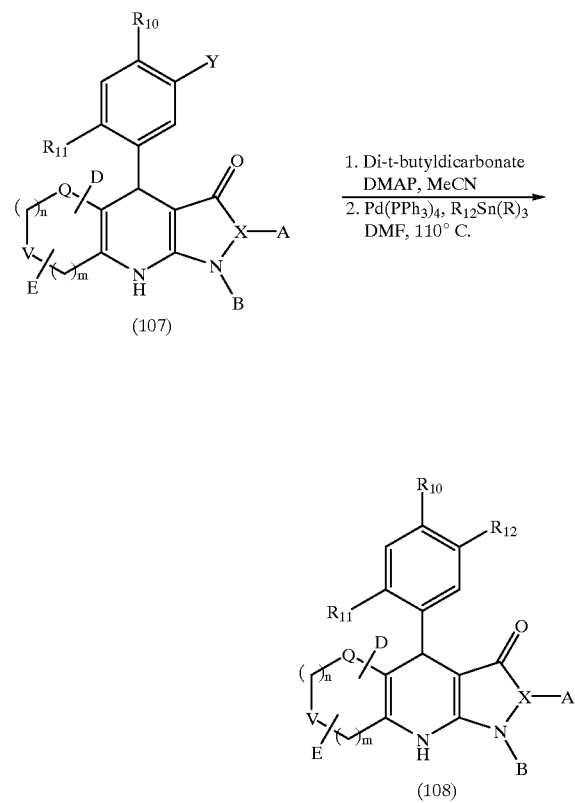

Scheme 23

(107)

(108)

Dihydropyridines of general formula (108), wherein Q, V, X, A, B, D, E, n and m are as defined in formula I, $R_{10}$ is selected from hydrogen, alkyl, alkylcarbonyl, alkylsulfonyl, aryl, heteroaryl, cyano, haloalkyl, chlorine, fluorine, haloalkoxy, nitro, alkoxy, and alkylthio, and —C(O)N$Z_1Z_2$, wherein $Z_1$ and $Z_2$ are independently selected from hydrogen, alkyl, alkylcarbonyl, aryl, arylalkyl, and formyl, $R_{11}$ is selected from hydrogen, hydroxy, alkoxy, haloalkoxy, and arylalkoxy, $R_{12}$ is selected from alkyl, vinyl, aryl, heteroaryl, cyano and the like, can be prepared as described in Scheme 23. Compounds of general formula (107), wherein Y is selected from bromine, iodine, and triflate, are protected with a tert butoxycarbonyl (Boc) group using standard procedures. The aromatic bromide, iodide, or triflate can be treated with a suitable tin, boronic acid, or unsaturated halide reagent in the presence of a palladium catalyst with heating in a solvent such as dimethylformamide to effect a coupling reaction that provides dihydropyridines of general formula (108). The conditions for this transformation also effect the removal of the Boc protecting group.

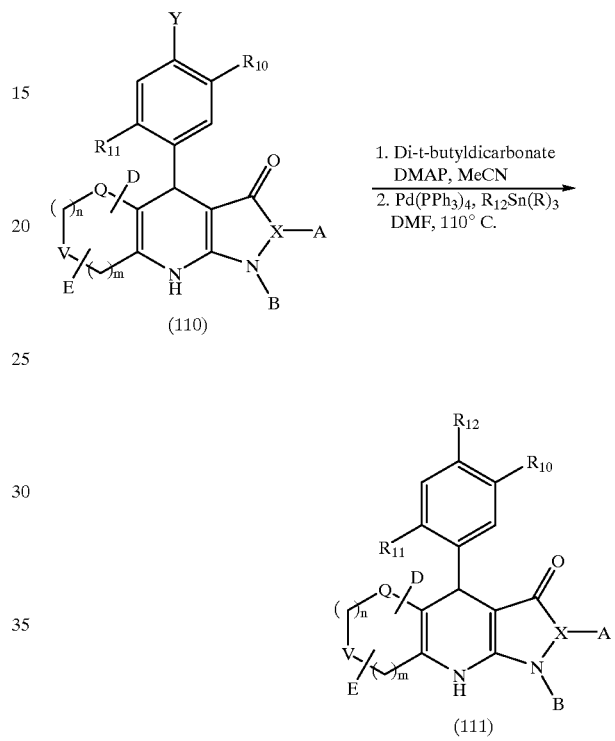

Scheme 24

(110)

(111)

Dihydropyridines of general formula (111), wherein Q, V, X, A, B, D, E, n and m are as defined in formula I, $R_{10}$ is selected from hydrogen, alkyl, alkylcarbonyl, alkylsulfonyl, aryl, heteroaryl, cyano, haloalkyl, chlorine, fluorine, haloalkoxy, nitro, alkoxy, alkylthio, and —C(O)N$Z_1R_2$, wherein $Z_1$ and $Z_2$ are independently selected from hydrogen, alkyl, alkylcarbonyl, aryl, arylalkyl, and formyl, $R_{11}$ is selected from hydrogen, hydroxy, alkoxy, haloalkoxy, and arylalkoxy, $R_{12}$ is selected from alkyl, vinyl, aryl, heteroaryl, cyano and the like, can be prepared as described in Scheme 24. Dihydropyridines of general formula (110), wherein Y is selected from bromine, iodine, and triflate, can be protected with a tert butoxycarbonyl (Boc) group using standard procedures. The aromatic bromide, iodide, or triflate can be reacted with a suitable tin, boronic acid, or unsaturated halide reagent in the presence of a palladium catalyst with heating in a solvent such as dimethylformamide to effect a coupling reaction that provides dihydropyridines of general formula (111). The conditions for this transformation also effect the removal of the Boc protecting group.

Scheme 25

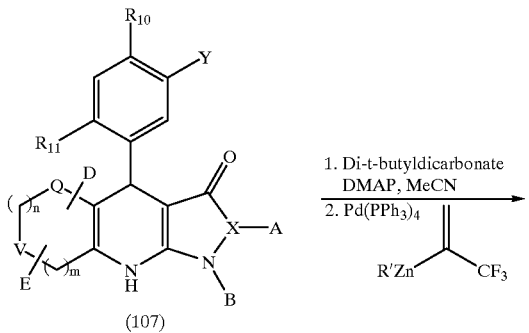

Scheme 26

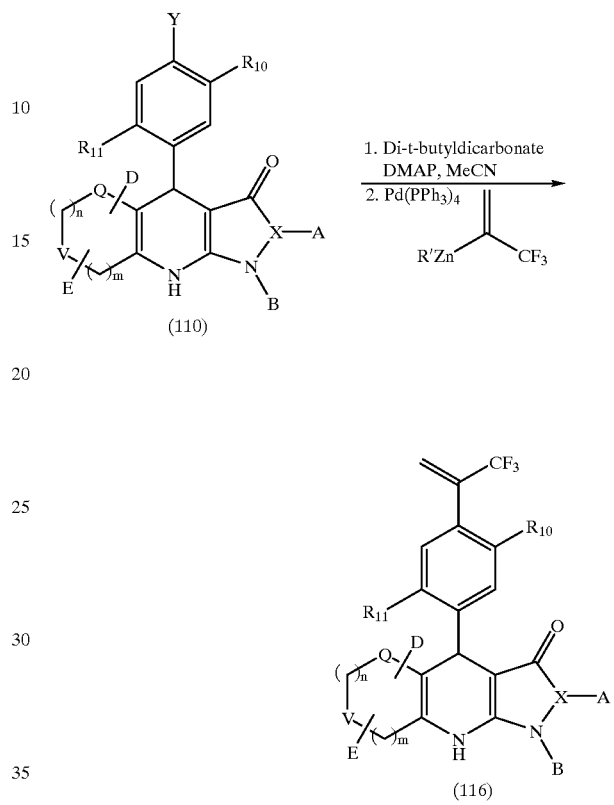

Dihydropyridines of general formula (113), wherein Q, V, X, A, B, D, E, n and m are as defined in formula I, $R_{10}$ is selected from hydrogen, alkyl, alkylcarbonyl, alkylsulfonyl, aryl, heteroaryl, cyano, haloalkyl, chlorine, fluorine, haloalkoxy, nitro, alkoxy, alkylthio, and —C(O)N$Z_1Z_2$, wherein $Z_1$ and $Z_2$ are independently selected from hydrogen, alkyl, alkylcarbonyl, aryl, arylalkyl, and formyl, and $R_{11}$ is selected from hydrogen, hydroxy, alkoxy, haloalkoxy, and arylalkoxy, can be prepared as described in Scheme 25. Dihydropyridines of general formula (107), wherein Y is selected from bromine, iodine, and triflate can be protected with a tert-butoxycarbonyl (Boc) group using standard procedures. The aromatic bromide, iodide, or triflate can be treated with a suitable halozinc reagent in the presence of a palladium catalyst with heating in a solvent such as dimethylformamide to effect a coupling reaction that provides dihydropyridines of general formula (113). The conditions for this transformation also effect the removal of the Boc protecting group. The types of meta substituents that may be introduced in this fashion include trihalopropenyl and more specifically the trifluoropropenyl group.

Dihydropyridines of general formula (116), wherein Q, V, X, A, B, D, E, n and m are as defined in formula I, $R_{10}$ is selected from hydrogen, alkyl, alkylcarbonyl, alkylsulfonyl, aryl, heteroaryl, cyano, haloalkyl, chlorine, fluorine, haloalkoxy, nitro, alkoxy, alkylthio, —C(O)N$Z_1Z_2$, wherein $Z_1$ and $Z_2$ are independently selected from hydrogen, alkyl, alkylcarbonyl, aryl, arylalkyl, and formyl, $R_{11}$ is selected from hydrogen, hydroxy, alkoxy, haloalkoxy, and arylalkoxy, can be prepared as described in Scheme 26. Dihydropyridines of general formula (110), wherein Y is selected from bromine, iodine, and triflate can be protected with a tert-butoxycarbonyl (Boc) group using standard procedures. The aromatic bromide, iodide, or triflate can be treated with a suitable halozinc reagent in the presence of a palladium catalyst with heating in a solvent such as dimethylformamide to effect a coupling reaction that provides dihydropyridines of general formula (116). The conditions for this transformation also effect the removal of the Boc protecting group. The types of para substituents that may be introduced in this fashion include trihalopropenyl and more specifically the trifluoropropenyl group.

Scheme 27

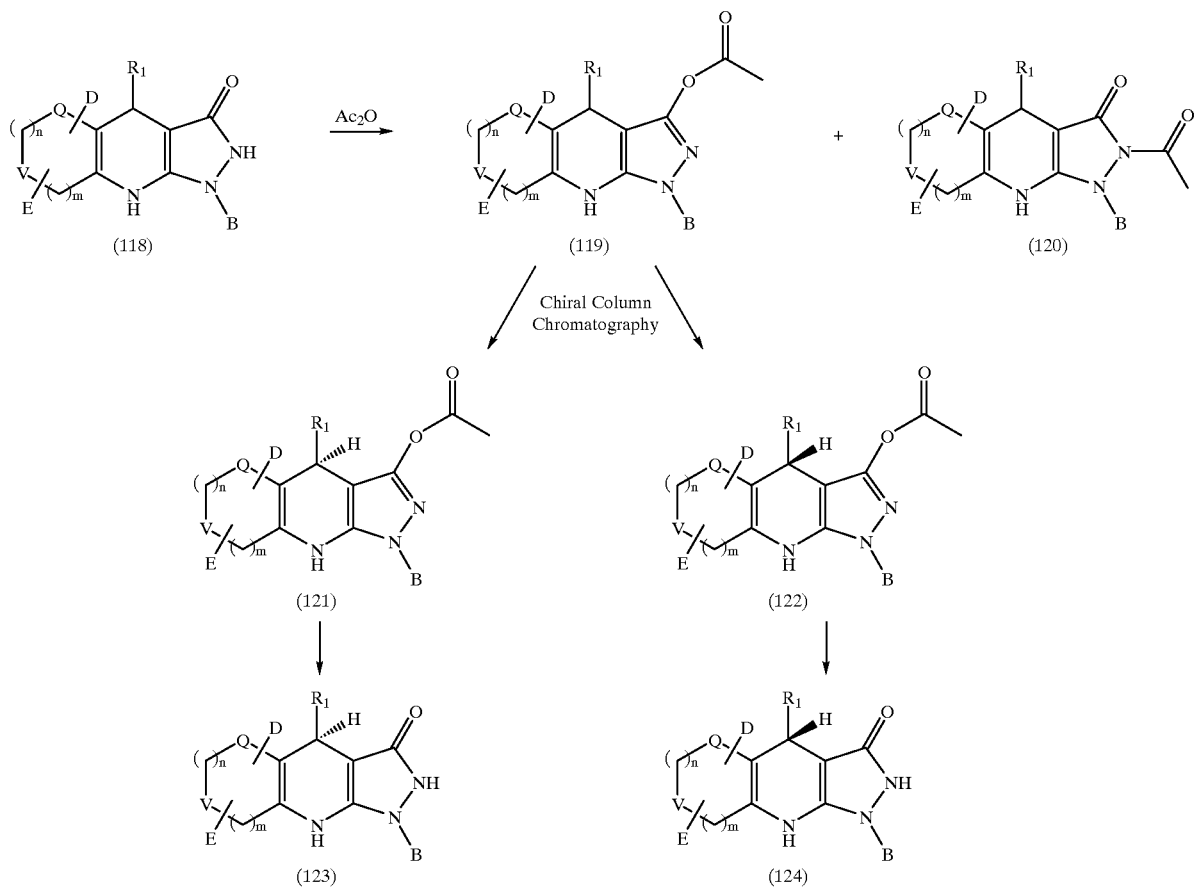

Dihydropyridines of general formula 118, wherein $R_1$, Q, V, B, D, E, m, and n are as defined in formula I provided that B is other than hydrogen, may be separated into individual enantiomers using the procedure described in Scheme 27. Dihydropyridines of general formula (118) can be treated with acetic anhydride (excess) and heat to provide acylated dihydropyridines of general formula (119) and (120). Dihydropyridines of general formula (119) and (120) can be separarted by flash chromatography. Dihydropyridines of general formula (119) can then be subjected to chiral column chromatography to provide enantiomers of general formula (121) and (122). Enantiomers of general formula (121) and (122) can be treated with 6N HCl in methanol with heat to provide enantiomerically pure dihydropyridines of general formula (123) and (124). Scheme 27 represents one technique for separation of dihydropyridine racamates. Racemates may also be separated via chiral column chromatography before treatment with acetic anhydride.

The compounds and processes of the present invention will be better understood by reference to the following examples, which are intended as an illustration of and not a limitation upon the scope of the invention. Further, all citations herein are incorporated by reference.

EXAMPLE 1

4-(3-bromo4-fluorophenyl)-1-methyl-1,2,4,6,7,8-hexahydrocyclopenta[b]pyrazolo[4,3-e]pyridine-3,5-dione 5-Amino-1-methyl-1,2-dihydropyrazol-3-one (0.23 g, 2 mmol), prepared as described in (C. Taylor and J. Barton, J.Am.Chem. Soc., (1959) 81, 2448), 3-bromo4-fluorobenzaldehyde (0.4 g, 2 mmol), and 1,3-cyclopentanedione (0.2 g, 2 mmol) in ethyl alcohol (4 mL) were heated at 80° C. for 2 days in a sealed tube. The reaction was cooled and the resulting precipitate was filtered off to provide 0.6 g (79%) of the title compound as a tan solid. $^1$H NMR (300 MHz, DMSO-$d_6$) δ 2.3 (t, 2H), 2.69 (m, 2H), 3.5 (s, 3H), 4.7 (s, 1H), 7.15 (m, 1H), 7.2 (t, 1H), 7.39 (dd, 1H), 9.56 (s, 1H), 10.42(s, 1H); MS (ESI+) m/z 380 (M+H)$^+$; Anal. calcd for $C_{16}H_{13}N_3BrFO_2 \cdot C_2H_6O$: C, 50.96;H, 4.51; N, 9.90. Found: C, 50.51; H, 4.58; N, 9.79.

EXAMPLE 2

4-(3-bromo-4-fluorophenyl)-1,2,4,6,7,8-hexahydrocyclopenta[b]pyrazolo[4,3-e]pyridine-3,5-dione 5-Amino-1,2-dihydropyrazol-3-one (0.15 g, 1.5 mmol), 3-bromo-4-fluorobenzaldehyde (0.31 g, 1.5 mmol), and 1,3-cyclopentanedione (0.15 g, 1.5 mmol) in ethyl alcohol (3 mL) were heated at 80° C. for 2 days in a sealed tube. The reaction mixture was evaporated under reduced pressure and the residue was chromatographed on silica gel eluting with ethyl acetate:formic acid:water (18:1: 1) to provide 0.125 g of the title compound as a tan solid. $^1$H NMR (300 MHz, DMSO-$d_6$) δ 2.22 (t, 2H), 2.61 (m, 2H), 4.73 (s, 1H), 7.15 (m, 1H), 7.2 (m, 1H), 7.4 (dd, 1H), 9.75 (s, 1H), 10.21 (s, 1H), 11.3 (bs, 1H); MS (ESI−) m/z 362 (M−H)$^-$; Anal. calcd for $C_{15}H_{11}N_3BrFO_2 \cdot 0.5H_2O$: C, 48.28;H, 3.24; N, 11.26. Found: C, 48.88;H, 3.29; N, 10.83.

EXAMPLE 3

4-(3-bromo-4-fluorophenyl)-4,7,8,9-tetrahydro-1H-pyrazolo[3,4-b]quinoline-3,5(2H,6H)-dione 5-Amino-1,2-dihydropyrazol-3-one (0.15 g, 1.5 mmol), 3-bromo-4-fluorobenzaldehyde (0.3 g, 1.5 mmol), and 1,3-cyclohexanedione (0.17 g, 1.5 mmol) were processed as described in Example 2 to provide 0.14 g of the title compound. $^1$H NMR (300 MHz, DMSO-$d_6$)δ 1.85 (m, 2H), 2.18 (m, 2H), 2.55 (m, 2H), 4.94 (s, 1H), 7.12 (m, 1H), 7.18 (t, 1H), 7.4 (dd, 1H), 9.75 (s, 1H), 10.35 (bs, 1H), 11.33 (bs, 1H); MS (ESI−) m/z 376 (M−H:)$^-$ Anal. Calcd for $C_{16}H_{13}N_3BrFO_2$: C, 50.79;H, 3.44; N, 1 1.11. Found: C, 50.45;H, 3.42; N, 11.33.

EXAMPLE 4

4-(3-bromo-4-fluorophenyl)-1-ethyl-1,2,4,6,7,8-hexahydrocyclopentafblpyrazolo[4,3-e]pyridine-3,5-dione 5-Amino-1-ethyl-1,2-dihydropyrazol-3-one (0.13 g, 1 mmol), prepared by the method of (A. Weisberger and A. Porter, J. Amer. Chem. Soc, (1944) 66,1849) from ethylhydrazine and ethyl cyanoacetate, 3-bromo-4-fluorobenzaldehyde (0.2 g, 1 mmol), and 1,3-cyclopentanedione (0.1 g, 1 mmol) in ethyl alcohol (2 mL) were heated at 80° C. for 2 days in a sealed tube. The reaction mixture was cooled and the resulting precipitate was filtered off to provide 0.23 g (58%) of the title compound as a tan solid. $^1$H NMR (300 MHz, DMSO-$d_6$)δ1.22 (t, 3H), 2.28 (t, 2H), 2.68 (m, 2H), 3.82 (q, 2H), 4.7 (s, 1H), 7.17 (m, 1H), 7.2 (t, 1H), 7.4 (dd, 1H), 9.64 (bs, 1H), 10.4 (s, 1H); MS (ESI−) m/z 392 (M−H:)$^-$, Anal. calcd for $C_{17}H_{15}N_3BrFO_2.0.5H_2O$: C, 50.89;H, 4.02; N, 10.47. Found: C, 50.85;H, 3.72; N, 10.25.

EXAMPLE 5

4-(3-bromo-4fluorophenyl)-1-tert-butyl-1,2,4,6,7,8-hexahydrocyclopenta[b]pyrazolo[4,3-e]pyridine-3,5-dione 5-Amino-1-tert-butyl-1,2-dihydropyrazol-3-one (0.23 g, 1.5 mmol), prepared by the method of (A. Weisberger and A. Porter, J. Amer. Chem. Soc, (1944) 66, 1849) from tert-butylhydrazine and ethyl cyanoacetate, 3-bromo-4-fluorobenzaldehyde (0.3 g, 1.5 mmol), and 1,3-cyclopentanedione (0.147 g, 1.5 mmol) in ethyl alcohol (3 mL) were heated at 80° C. for 2 days in a sealed tube. The solvent was evaporated under reduced pressure and the residue was chromatograhed on silica gel eluting with 10% ethanol/methylene chloride to provide 0.12 g of the title compound as a tan solid. $^1$H NMR (300 MHz, DMSO-$d_6$) δ 1.51 (s, 9H), 2.28 (m, 2H), 2.71 (m, 2H), 4.69 (s, 1H), 7.12 (m, 1H), 7.21 (t, 1H), 7.39 (dd, 1H), 9.43 (bs, 1H), 9.57 (s, 1H); MS (ESI−) m/z 420 (M−H)$^-$; Anal. calcd for $C_{19}H_{19}N_3BrFO_2$: C, 54.17;H, 4.79; N, 9.97. Found: C, 54.17;H, 4.81; N, 9.85.

EXAMPLE 6

4-(3-bromo-4-fluorophenyl)-1-(2-pyridinyl)-1,2,4,6,7,8-hexahydrocyclopenta[b]pyrazolo[4,3-e]pyridine-3,5-dione 5-Amino-1-(2-pyridyl)-1,2-dihydropyrazol-3-one (0.26 g, 1.5 mmol), prepared as described in (Weisberger A., Porter H. D., J. Am. Chem. Soc., (1944) 66, 1849), 3bromo-4-fluorobenzaldehyde (0.3 g, 1.5 mmol), and 1,3-cyclopentanedione (0.147 g, 1.5 mmol) in ethyl alcohol (3 mL) were heated at 80° C. for 2 days in a sealed tube. The reaction mixture was cooled and the resulting precipitate was filtered off to provide 0.2 g of the title compound as a tan solid. $^1$H NMR (300 MHz, DMSO-$d_6$) δ 2.32 (m, 2H), 2.8 (m, 2H), 4.82 (s, 1H), 7.22 (m, 3H), 7.48 (dd, 1H), 7.55 (dd, 1H), 7.92 (t, 1H), 8.41 (m, 1H), 10.42 (s, 1H), 10.55 (bs, 1H); MS (ESI−) m/z 439 (M−H)$^-$; Anal. calcd for $C_2H_{14}N_4BrFO_2.0.25H_2O$: C, 53.89;H, 3.28; N, 12.57. Found: C, 53.76;H, 3.01; N, 13.22.

EXAMPLE 7

1-methyl-4-[4-(trifluoromethoxy)phenyl]-1,2,4,6,7,8-hexahydrocyclopenta[b]pyrazolo[4,3-e]pyridine-3,5-dione 4-Trifluoromethoxybenzaldehyde (0.28 g, 1.5 mmol), 1,3-cyclopentadione (0.15 g, 1.5 mmol), and 5-amino-1-methyl-1,2-dihydropyrazol-3-one (0.17 g, 1.5 mmol) were processed as described in Example 1 to provide 0.15 g of the title compound. $^1$H NMR (300 MHz, DMSO-$d_6$) δ 2.3 (t, 2H), 2.68 (m, 2H), 3.49 (s, 3H), 4.72 (s, 1H), 7.18 (d, 2H), 7.23 (d, 2H), 9.5 (bs, 1H) 10.37 (s, 1H); MS (ESI−) m/z 364 (M−H)$^-$; Anal. calcd for $C_{17}H_{14}N_3F_3O_3.0.25\ H_2O$: C, 55.21;H, 3.95; N, 11.36. Found: C, 55.34;H, 3.78; N, 10.97.

EXAMPLE 8

4-(3-bromo-4-methylphenyl)-1-methyl-1,2,4,6,7,8-hexahydrocyclopenta[b]pyrazolo[4,3-e]pyridine-3,5-dione 4-Methyl-3-bromobenzaldehyde (0.3 g, 1.5 mmol), prepared as described in (Pearson et al., J. Org. Chem. (1958) 23, 1412–1416), 1,3-cyclopentadione (0.15 g, 1.5 mmol), and 5-amino-1-methyl-1,2-dihydropyrazol-3-one (0.17 g, 1.5 mmol) were processed as described in Example 1 to provide 0.34 g of the title compound. $^1$H NMR (300 MHz, DMSO-$d_6$) δ 2.27 (s, 3H), 2.29 (t, 2H), 2.67 (m, 2H), 3.5 (s, 3H), 4.63 (s, 1H), 7.04 (dd, 1H), 7.18 (d, 1H), 7.29 (ds, 1H), 9.51 (bs, 1H), 10.37 (s, 1H); MS (ESI−) m/z 361 (M−H)$^-$; Anal. calcd for $C_{17}H_{16}N_3BrO_2$: C, 54.54;H, 4.28; N, 11.23. Found: C, 54.30;H, 4.46;N, 10.94.

EXAMPLE 9

4-[4-fluoro-3-(trifluoromethyl)phenyl]-1-methyl-1,2,4,6,7,8-hexahydrocyclopenta[b]pyrazolo[4,3-e]pyridine-3,5-dione 4-Fluoro-3-trifluoromethylbenzaldehyde (0.28 g, 1.5 mmol), 1,3-cyclopentadione (0.15 g, 1.5 mmol), and 5-amino-1-methyl-1,2-dihydropyrazol-3-one (0.17 g, 1.5 mmol) were processed as described in Example 1 to provide 0.35 g of the title compound. $^1$H NMR (300 MHz, DMSO-$d_6$) δ 2.21 (m, 2H), 2.7 (m, 2H), 3.51 (s, 3H), 4.8 (s, 1H), 7.35 (t, 1H), 7.45 (m, 1H), 7.55 (d, 1H), 9.6 (bs, 1H), 10.48 (s, 1H); MS (ESI−) m/z 366 (M−H)$^-$; Anal. calcd for $C_{17}H_{13}N_3F_4O_2$: C, 55.59;H, 3.51; N, 11.44. Found: C, 55.41;H, 3.37; N, 11.21.

EXAMPLE 10

4-(4-chloro-3-nitrophenyl)-1-methyl-1,2,4,6,7,8-hexahydrocyclopenta[b]pyrazolo[4,3-e]pyridine-3,5-dione 4-Chloro-3-nitrobenzaldehyde (0.27 g, 1.5 mmol), 1,3cyclopentadione (0.15 g, 1.5 mmol), and 5-amino-1- methyl-1,2-dihydropyrazol-3-one (0.17 g, 1.5 mmol) were processed as described in Example 1 to provide 0.3 g of the title compound. $^1$H NMR (300 MHz, DMSO-d$_6$) δ 2.3 (t, 2H), 2.68 (m, 2H), 3.5 (s, 3H), 4.81 (s, 1H), 7.48 (dd, 1H), 7.6 (d, 1H), 7.78 (d, 1H), 9.61 (bs, 1H), 10.49 (s, 1H); MS (ESI−) m/z 359 (M−H)$^-$; Anal. calcd for C$_{16}$H$_{13}$N$_4$ClO$_4$: C, 53.27;H, 3.63; N, 15.53. Found: C, 53.16;H, 3.88; N, 14.83.

EXAMPLE 11

4-(3-iodo-4-methylphenyl)-1-methyl-1,2,4,6,7,8-hexahydrocyclopenta[b]pyrazolo[4,3-e]pyridine-3,5-dione

Example 11A 3-iodo-4-methylbenzaldehyde

3-Iodo-4-methyl-benzoic acid (1.0 g, 3.96 mmol) in dry CH$_2$Cl$_2$:THF 1:1 (200 mL) was treated with oxalyl chloride (1 mL, 11.9 mmol) and several drops of DMF. The mixture was heated at 65° C. for 30 minutes, cooled to ambient temperature, and concentrated under reduced pressure to provide a light yellow solid. The obtained solid in THF (200 mL) was treated with LiAlH(O$^t$Bu)$_3$ (4.1 mL, 4.1 mmol) via syringe at −78° C. After 30 minutes at −78° C., a saturated solution of Rochelle's salt was added and the mixture was allowed to warm to ambient temperature. The organic layer was washed in succession with 1 NHCl, saturated NaHCO$_3$, brine, dried over Na$_2$SO$_4$, and the solvent removed under reduced pressure. The resulting residue was purified by flash chromatography using hexanes:EtOAc (4:1) as eluent to provide 3-iodo-4-methylbenzaldehyde as a white solid (300 mg, 18%).

Example 11B 4-(3-iodo-4-methylphenyl)-1-methyl-1,2,4,6,7,8-hexahydrocyclopenta[b]pyrazolo[4,3-e]pyridine-3,5-dione 3-Iodo-4-methylbenzaldehyde (0.37 g, 1.5 mmol) from Example 11A, 1,3-cyclopentadione (0.15 g, 1.5 mmol), and 5-amino-1-methyl-1,2-dihydropyrazol-3-one (0.17 g, 1.5 mmol) were processed as described in Example 1 to provide 0.15 g of the title compound. $^1$H NMR (300 MHz, DMSO-d$_6$) δ 2.25 (s, 3H) 2.3 (m, 2H), 2.68 (m, 2H), 3.49 (s, 3H), 4.6 (s, 1H), 7.05 (dd, 1H), 7.14 (d, 1H), 7.53 (d, 1H), 9.5 (bs, 1H), 10.35 (s, 1H); MS (ESI−) m/z 420 (M−H)$^-$; Anal. calcd for C$_{17}$H$_{16}$N$_3$IO$_2$.0.75 C$_2$H$_6$O: C, 48.75;H, 4.53; N, 9.22. Found: C, 49.03;H, 4.50; N, 9.72.

EXAMPLE 12

4-(4-fluoro-3-iodophenyl)-1-methyl-1,2,4,6,7,8-hexahydrocyclopenta[b]pyrazolo[4,3-e]pyridine-3,5-dione

Example 12A (3-amino-4-fluorophenyl)methanol

3-Amino-4-fluorobenzoic acid (15 g, 97 mmol) in tetrahydrofuran at 0° C. was treated with 1.0 M borane-tetrahydrofuran complex (50 mL). After stirring overnight at ambient temperature, the mixture was treated with an additional 130 mL of 1.0 M borane-tetrahydrofuran complex. After stirring for 10 hours, the mixture was quenched by the addition of methanol, stirred 3 hours at ambient temperature, concentraed and partitioned between aqueous sodium bicarbonate/methylene chloride. The methylene chloride layer was dried (sodium sulfate), filtered and concentrated. The residue was purified by flash chromatography over silica gel (ethyl acetate/hexane 1:1) to provide 7.0 g of the title compound.

$^1$H NMR (300 MHz, CDCl$_3$) δ 4.58 (s, 2H), 6.67 (br m, 1H), 6.81 (d, 1H), 6.95 (t, 1H).

Example 12B (4-fluoro-3-iodophenyl)methanol

The product from Example 12A (7.0 g, 50 mmol) in water (100 mL) at 0° C. was treated slowly with concentrated sulfuric acid (30 mL) at a rate to maintain the temperature below 10° C. and then treated dropwise with an aqueous solution of sodiumnitrite (3.45 g, 50 mmol). This solution was then added to a solution of potassium iodide (8.13 g, 50 mmol) in water (15 mL), heated at 60° C. for 2 hours, cooled and extracted with methylene chloride. The methylene chloride layer was washed with 10% sodiumhydroxide, washed with 1 M sodium thiosulfate, washed with 10% hydrochloric acid, washed with aqueous sodium bicarbonate, dried (sodium sulfate), filtered and concentrated. The residue was purified by flash chromatography over silica gel (ethyl acetate/hexane 7:3) to provide 6.4 g of the title compound. $^1$H NMR (300 MHz, CDCl$_3$) δ 1.69 (t, 1H), 4.66 (d, 2H), 7.05 (t, 1H), 7.60 (d, 1H), 7.78 (dd, 1H).

Example 12C 4-fluoro-3-iodobenzaldehyde

The product from Example 12B (6.4 g, 26 mmol) in chloroform (300 mL) was treated with manganese dioxide (4.5 g, 50 mmol), stirred overnight, treated with an additional portion of manganese dioxide (2.25 g), stirred overnight, filtered and concentrated. The residue was purified by flash chromatography over silica gel (ethyl acetate/hexane 1:4) to provide 1.9 g of the title compound. $^1$H NMR (300 MHz, CDCl$_3$) δ 7.23 (t, 1H), 7.89 (m, 1H), 8.32 (dd, 1H), 9.91 (s, 1H).

Example 12D 4-(4-fluoro-3-iodophenyl)-1-methyl-1,2,4,6,7,8-hexahydrocyclopenta[b]pyrazolo[4,3-e]pyridine-3,5-dione 4-Fluoro-3-iodobenzaldehyde (0.25 g, 1.0 mmol) from Example 12C, 1,3 cyclopentadione (0.1 g, 1.0 mmol) and 5-amino-1-methyl-1,2-dihydropyrazol-3-one (0.11 g, 1.0 mmol) were processed as described in Example 1 to provide 0.27 g of the title compound.

$^1$H NMR (300 MHz, DMSO-d$_6$) δ 2.3 (m, 2H), 2.68 (m, 2H), 3.5 (s, 3H), 4.67 (s, 1H), 7.1 (t, 1H), 7.15 (m, 1H), 7.52 (dd, 1H), 9.52 (s, 1H), 10.4 (s, 1H); MS (ESI−) m/z 424 (M−H)$^-$; Anal. calcd for C$_{16}$H$_{13}$N$_3$FIO$_2$: C, 46.27;H, 3.55; N, 9.25. Found: C, 46.65;H, 3.65; N, 9.55.

EXAMPLE 13

4-(3,4-dichlorophenyl)-1-methyl-1,2,4,6,7,8-hexahydrocyclopenta[b]pyrazolo[4,3-e]pyridine-3,5-dione 3,4-Dichlorobenzaldehyde (0.17 g, 1.0 mmol), 1,3-cyclopentadione (0.1 g, 1.0 mmol), and 5-amino-1-methyl-1,2-dihydropyrazol-3-one (0.11 g, 1.0 mmol) were processed as described in Example 1 to provide 0.24 g of the title compound. $^1$H NMR (300 MHz, DMSO-d$_6$) δ 2.28 (t, 2H), 2.68 (m, 2H), 3.5 (s, 3H), 4.7 (s, 1H), 7.13 (dd, 1H), 7.33 (d, 1H), 7.49 (d, 1H), 9.58 (s, 1H), 10.45 (s, 1H); MS (ESI−) m/z 348 (M−H)$^-$; Anal. calcd for C$_{16}$H$_{13}$N$_3$Cl$_2$O$_2$:C, 54.71;H, 4.32; N, 11.26. Found: C, 54.37;H, 4.40; N, 10.80.

EXAMPLE 14

4-[4-fluoro-3-(2-furyl)phenyl]-1-methyl-1,2,4,6,7,8-hexahydrocyclopenta[b]pyrazolo[4,3-e]pyridine-3,5-dione

Example 14A 4-fluoro-3-(2-furyl)-benzaldehyde

3-Bromo-4fluorobenzaldehyde (1 g, 4.93 mmol) in DMF (25 ml) was treated with 2 (tributylstannyl)furan (2.4 ml, 1.05 mmol), di-tert-butyl dicarbonate (1.75 g, 4.94 mmol), and tetrakis(triphenylphosphine)palladium (0) (570 mg, 0.4 mmol). The mixture was heated at 110° C. in a sealed high pressure tube over night, allowed to cool to ambient temperature, diluted with ethyl acetate, and washed with brine. The organic layer was further washed with 1N HCl, saturated NaHCO$_3$, brine, dried (Na$_2$SO$_4$), and concentrated under reduced pressure. The residue was purified by flash chromatography using hexanes:diethyl ether (20:1) as eluent to provide the title compound as a pale yellow oil (0.96 g, 98%).

Example 14B

4-[4-fluoro-3-(2-furyl)phenyl]-1-methyl-1,2,4,6,7,8-hexahydrocyclopenta[b]pyrazolo[4,3-e]pyridine-3,5-dione 4-Fluoro-3-(2-furyl)-benzaldehyde (0.38 g, 2.0 mmol) from Example 14A, 1,3-cyclopentadione (0.2 g, 2.0 mmol), and 5-amino-1-methyl-1,2-dihydropyrazol-3-one (0.22 g, 2.0 mmol) were processed as described in Example 1 to provide 0.54 g of the title compound.

$^1$H NMR (300 MHz, DMSO) δ 2.29 (m, 2H), 2.67 (m, 2H), 3.50 (s, 3H), 4.73 (s, 1H), 6.63 (q, 1H, J=1.5 Hz), 6.79 (t, 1H, J=3.30 Hz), 7.05–7.17 (m, 2H), 7.58 (dd, 1H, J=7.35, 2.21 Hz), 7.81 (d, 1H, J=1.47 Hz), 9.51 (s, 1H), 10.29 (s, 1H); MS (ESI−) m/z 364 (M−H)$^-$; Anal. calcd for C$_{20}$H$_{16}$N$_3$FO$_3$: C, 65.75;H, 4.41; N, 11.50. Found: C, 65.99;H, 4.56; N, 11.12.

EXAMPLE 15

1-methyl-4-(5-nitro-3-thienyl)-1,2,4,6,7,8-hexahydrocyclopenta[b]pyrazolo[4,3-e]pyridine-3,5-dione 2-Nitrothiophene-4-carboxaldehyde (0.16 g, 1.0 mmol), 1,3-cyclopentadione (0.1 g, 1.0 mmol), and 5-amino-1-methyl-1,2-dihydropyrazol-3-one (0.11 g, 1.0 mmol) were processed as described in Example 1 to provide 0.24 g of the title compound. $^1$H NMR (300 MHz, DMSO-d$_6$) δ 2.35 (m, 2H), 2.68 (m, 2H), 3.5 (s, 3H), 4.8 (s, 1H), 7.51 (d, 1H), 7.89 (d, 1H), 9.75 (bs, 1H), 10.47 (s, 1H); MS (ESI−) m/z 331 (M−H)$^-$; Anal. calcd for C$_4$H$_{12}$N$_4$O$_4$S: C, 50.60;H, 3.64; N, 16.86. Found: C, 51.06;H, 3.68; N, 16.97.

EXAMPLE 16

4-(2,1,3-benzoxadiazol-5-yl)-1-methyl-1,2,4,6,7,8-hexahydrocyclopenta[b]pyrazolo[4,3-e]pyridine-3,5-dione 2,1,3-Benzoxadiazole-5-carboxaldehyde (0.15 g, 1.0 mmol), prepared as described in (Gasco, A. M., Ermondi, G. Eur. J. Med. Chem., (1996) 31, 3), 1,3cyclopentadione (0.1 g, 1.0 mmol), and 5-amino-1-methyl-1,2-dihydropyrazol-3-one (0.11 g, 1.0 mmol) were processed as described in Example 1 to provide 0.17 g of the title compound. $^1$H NMR (300 MHz, DMSO-d$_6$) δ 2.32 (m, 2H), 2.71 (m, 2H), 3.51 (s, 3H), 4.87 (s, 1H), 7.5 (dd, 1H), 7.6 (s, 1H), 7.9 (d, 1H), 9.61 (bs, 1H), 10.52 (s, 1H);

MS (ESI−) m/z 322 (M−H)$^-$; Anal. Calcd for C$_{16}$H$_{13}$N$_5$O$_3$: C, 59.44;H, 4.05; N, 21.66. Found: C, 59.14;H, 3.84; N, 21.77.

EXAMPLE 17

4-(2,1,3-benzothiadiazol-5-yl)-1-methyl-1,2,4,6,7,8-hexahydrocyclopenta[b]pyrazolo[4,3-e]pyridine-3,5-dione

Example 17A

5-Bromomethylbenzo-2,1,3-thiadiazole

5-Methylbenzo-2,1,3-thiadiazole (5 g, 33.3 mmol) in CHCl$_3$ (75 mL) was treated with N-bromosuccinimide (5.32 g, 33.3 mmol) and a catalytic amount of AIBN and heated at reflux for 16 hours. After cooling to ambient temperature, the resulting precipitate was fitered off and the filtrate was concentrated under reduced pressure. The residue was recrystallized from ethanol to provide 4.8 g of the title compound. $^1$H NMR (300 MHz, CDCl$_3$) δ 4.62 (s, 2H), 7.65 (dd, 1H), 8.0 (m, 2H).

Example 17B 2,1,3-thiadiazole-5-benzylalcohol

The product from Example 17A (4.8 g, 21 mmol) and CaCO$_3$ (10 g, 100 mmol) in 1:1 dioxane:water (120 mL) were heated at reflux for 3 hours. The reaction mixture was evaporated under reduced pressure and partitioned between 2N HCl/CH$_2$Cl$_2$. The organic layer was dried (MgSO$_4$) and concentrated under reduced pressure. The residue was chromatographed on silica gel eluting with 1:1 ethyl acetate-:hexane to provide 2.66 g of the title compound. $^1$H NMR (300 MHz, CDCl$_3$) δ 1.93 (t, 1H), 4.9 (d, 2H), 7.6 (dd, 1H), 8.0 (m, 2H).

Example 17C 2,1,3-Benzthiodiazole-5-carboxaldehyde

The product from the Example 17B (2.6 g, 16 mmol) in chloroform (150 mL) was treated with manganese dioxide (6 g, 64 mmol). After stirring overnight, the mixture was filtered and the filtrate concentrated under reduced pressure to provide the title compound. $^1$H NMR (CDCl$_3$) δ 8.12 (s, 2H), 8.5 (s, 1H), 10.21 (s, 1H).

Example 17D 4-(2,1,3-benzothiadiazol-5-yl)-1-methyl-1,2,4,6,7,8-hexahydrocyclopenta[b]pyrazolo[4,3-e]pyridine-3,5-dione 2,1,3-Benzthiodiazole-5-carboxaldehyde (0.24 g, 1.5 mmol) from Example 17C, 1,3 cyclopentadione (0.15 g, 1.5 mmol), and 5-amino-1-methyl-1,2-dihydropyrazol-3-one (0.17 g, 1.5 mmol) were processed as described in Example 1 to provide 0.21 g of the title compound.

$^1$H NMR (300 MHz, DMSO-d$_6$) δ 2.3 (t, 2H), 2.6 (m, 2H), 3.51 (s, 3H), 4.91 (s, 1H), 7.6 (dd, 1H), 7.7 (s, 1H), 7.91 (d,

1H), 9.53 (bs, 1H), 10.49 (s, 1H); MS (ESI) m/z 338 (M–H)⁻; Anal. Calcd for $C_{16}H_{13}N_5O_2S$: C, 56.63; H, 3.83; N, 20.65. Found: C, 56.74;H, 4.11; N, 20.34.

EXAMPLE 18

4-(3-bromo-4-fluorophenyl)-1-methyl-4,7,8,9-tetrahydro-1H-pyrazolo[3,4b]quinoline-3,5(2H,6H)-dione 3-Bromo-4-fluorobenzaldehyde (0.2 g, 1.0 mmol), 1,3cyclohexanedione (0.11 g, 1.0 mmol), and 5-amino-1-methyl-1,2-dihydropyrazol-3-one (0.11 g, 1.0 mmol) were processed as described in Example 1 to provide 0.27 g of the title compound. ¹H NMR (300 MHz, DMSO-$d_6$) δ 1.9 (m, 2H), 2.2 (m, 2H), 2.6 (m, 2H), 3.45 (s, 3H), 4.88 (s, 1H), 7.12 (m, 1H), 7.18 (t, 1H), 7.38 (dd, 1H), 9.53 (s, 1H), 9.72 (s, 1H); MS (ESI–) m/z 390 (M–H); Anal. Calcd for $C_{17}H_{15}N_3BrFO_2 \cdot C_2H_6O$: C, 52.06;H, 4.61; N, 9.85. Found: C, 51.72;H, 4.56 N, 9.58.

EXAMPLE 19

4-(3-bromo-4-fluorophenyl)-2-methyl-1,2,4,6,7,8-hexahydrocyclopenta[b]pyrazolo[4,3-e]pyridine-3,5-dione 3-Bromo-4-fluorobenzaldehyde (0.3 g, 1.5 mmol), 1,3cyclopentadione (0.15 g, 1.5 mmol), and 5-amino-2-methyl-1,2-dihydropyrazol-3-one (0.17 g, 1.5 mmol), prepared by the method of (C. Taylor and J. Barton, J.Am.ChemSoc., (1959) 81, 2448) were processed as described in Example 1 to provide 0.32 g of the title compound. ¹H NMR (300 MHz, DMSO-$d_6$) δ 2.21 (t, 2H), 2.59 (m, 2H), 3.38 (s, 3H), 4.75 (s, 1H), 7.13 (m, 1H), 7.2 (t, 1H), 7.42 (dd, 1H), 10.16 (s, 1H), 10.51 (bs, 1H); MS (ESI–) m/z 378 (M–H⁻) Anal. Calcd for $C_{16}H_{13}N_3BrFO_2$: C, 50.21;H, 3.56; N, 10.98. Found: C, 50.76;H, 4.09; N, 10.52.

EXAMPLE 20

4-(3-bromo-4-fluorophenyl)-2-phenyl-1,2,4,6,7,8-hexahydrocyclopenta[b]pyrazolo[4,3-e]pyridine-3,5-dione 3-Bromo-4-fluorobenzaldehyde (0.3 g, 1.5 mmol), 1,3-cyclopentadione (0.15 g, 1.5 mmol), and 5-amino-2-phenyl-1,2-dihydropyrazol-3-one (0.26 g, 1.5 mmol) were processed as in Example 1. The resulting precipitate was chromatographed on silica gel eluting with 10% ethanol/$CH_2Cl_2$ to provide 0.32 g of the title compound. ¹H NMR (300 MHz, DMSO-$d_6$) δ 2.26 (m, 2H), 2.63 (m, 2H), 4.86 (s, 1H), 7.21 (m, 3H), 7.4 (t, 2H), 7.51 (d, 1H), 7.67 (d, 2H),10.47 (s, 1H), 11.2 (s, 1H); MS (ESI–) m/z 438 (M+H)⁻; Anal. Calcd for $C_{21}H_{15}N_3FBrO_2$: C, 56.71;H, 3.51; N, 9.45. Found: C, 56.55;H, 3.86; N, 9.12.

EXAMPLE 21

4-(3-bromo-4-fluorophenyl)-1-methyl-1,2,4,6,7,8-hexahydro-3H-pyrazolo[3,4-b]thieno[2,3-e]pyridin-3-one 5,5-dioxide 5-Amino-1-methyl-1,2-dihydropyrazol-3-one (0.17 g, 1.5 mmol), 3-bromo-4-fluorobenzaldehyde (0.3 g, 1.5 mmol), and tetrahydrothiophene-3-oxo-1,1-dioxide (0.2 g, 1.5 mmol) in ethyl alcohol (3 mL) were heated at 80° C. for 2 days in a sealed tube. The reaction mixture was cooled and the resulting precipitate was filtered off and washed with ethyl acetate to provide 0.41 g of the title compound as a tan solid. ¹H NMR (300 MHz, DMSO-$d_6$) δ 2.88 (m, 1H), 3.03 (m, 1H), 3.4 (m, 2H), 3.48 (s, 3H), 4.92 (s, 1H), 7.21 (m, 1H), 7.24 (t, 1H), 7.4 (d, 1H), 9.55 (s, 1H), 9.89 (s, 1H);MS (ESI–) m/z 414 (M–H)⁻; Anal. Calcd for $C_{15}H_{13}N_3BrFO_3S$: C, 43.49;H, 3.16; N, 10.14. Found: C, 43.64;H, 3.50; N, 9.84.

EXAMPLE 22

4-(3-bromo-4-fluorophenyl)-1,6,6-trimethyl-4,7,8,9-tetrahydro-1H-pyrazolo[3,4-b]quinoline-3,5(2H,6H)-dione 5-Amino-1-methyl-1,2-dihydropyrazol-3-one (0.23 g, 2 mmol), 3-bromo-4-fluorobenzaldehyde (0.4 g, 2 mmol), and 4,4-dimethyl-1,3-cyclohexanedione (0.28 g, 2 mmol) in ethyl alcohol (3 mL) were heated at 80° C. in a sealed tube for 2 days. The reaction mixture was cooled and the resulting precipitate was filtered off and washed with ethyl acetate to provide 0.55 g of the title compound as a tan solid. ¹H NMR (300 MHz, DMSO-$d_6$) δ 0.92 (s, 3H), 0.98 (s, 3H), 1.78 (t, 2H), 2.63 (m, 2H), 3.43 (s, 3H), 4.83 (s, 1H), 7.11 (m, 1H), 7.17 (t, 1H), 7.33 (dd, 1H), 9.53 (s, 1H), 9.66(s, 1H); MS (ESI–) m/z 420 (M–H)⁻; Anal. calcd for $C_{19}H_{19}N_3BrFO_2$: C, 54.30;H, 4.56; N, 10.00. Found: C, 54.29;H, 4.61; N, 9.97.

EXAMPLE 23

4-(4-fluoro-3-iodophenyl)-1,6,6-trimethyl-4,7,8,9-tetrahydro-1H-pyrazolo[3,4-b]quinoline-3,5(2H,6H)-dione 5-Amino-1-methyl-1,2-dihydropyrazol-3-one (0.06 g, 0.5 mmol), 3-iodo-4-fluorobenzaldehyde (0.125 g, 0.5 mmol), and 4,4-dimethy 1,3-cyclohexanedione (0.07 g, 0.5 mmol) were processed as described in Example 22 to provide 0.15 g (66%) of the title compound. ¹H NMR (300 MHz, DMSO-$d_6$) δ 0.92 (s, 3H), 0.98 (s, 3H), 1.78 (t, 2H), 2.63 (m, 2H), 3.42 (s, 3H), 4.81 (s, 1H), 7.05 (t, 1H), 7.1 (m, 1H), 7.5 (dd, 1H), 9.5 (s, 1H), 9.61 (s, 1H); MS (ESI–) m/z 466 (M–H)³¹; Anal. calcd for $C_{19}H_{19}N_3ClO_2$: C, 48.82;H, 4.07; N, 9.00. Found: C, 48.83;H, 4.20; N, 8.83.

EXAMPLE 24

4-(3,4-dichlorophenyl)-1,6,6-trimethyl-4,7,8,9-tetrahydro-1H-pyrazolo[3,4-b]quinoline-3,5(2H,6H)-dione 5-Amino-1-methyl-1,2-dihydropyrazol-3-one (0.08 g, 0.75 mmol), 3,4 dichlorobenzaldehyde (0.13 g, 0.75 mmol), and 4,4-dimethyl-1,3-cyclohexanedione (0.10 g, 0.75 mmol) were processed as described in Example 22 to provide 0.2 g (67%) of the title compound. ¹H NMR (300 MHz, DMSO-$d_6$) δ 0.92 (s, 3H), 0.99 (s, 3H), 1.78 (t, 2H), 2.65 (m, 2H), 3.45 (s, 3H), 4.83 (s, 1H), 7.08 (dd, 1H), 7.29 (d, 1H), 7.42 (d, 1H), 9.52 (s, 1H), 9.68 (s, 1H); MS (ESI–) m/z 390 (M–H)⁻; Anal. calcd for $C_{19}H_{19}N_3Cl_2O_2$: C, 58.16;H, 4.84; N, 10.71. Found: C, 58.23;H, 4.75; N, 10.68.

EXAMPLE 25

4-[4-fluoro-3-(2-furyl)phenyl]-1,6,6-trimethyl-4,7,8,9-tetrahydro-1H-pyrazolo[3,4 b]quinoline-3,5(2H,6H)-dione 5-Amino-1-methyl-1,2-dihydropyrazol-3-one (0.11 g, 1 mmol), 4fluoro-3-(2-furyl)-benzaldehyde (0.19 g, 1 mmol), and 4,4-dimethyl-4,3-cyclohexanedione (0.14 g, 1 mmol) were processed as described in Example 22 to provide 0.28 g (67%) of the title compound. $^1$H NMR (300 MHz, DMSO-d$_6$) δ 0.92 (s, 3H), 0.99 (s, 3H), 1.78 (t, 2H), 2.65 (m, 2H), 3.45 (s, 3H), 4.88 (s, 1H), 6.62 (m, 1H), 6.76 (m, 1H), 7.06 (m, 1H), 7.1 (t, 1H), 7.55 (dd, 1H), 7.81 (dd, 1H), 9.49 (s, 1H), 9.6 (s, 1H); MS (ESI-) m/z 406 (M-H)$^-$; Anal. calcd for C$_{23}$H$_{22}$N$_3$FO$_3$: C, 67.80;H, 5.40; N, 10.3. Found: C, 68.05;H, 5.39; N, 10.25.

EXAMPLE 26

4-(3-bromo-4-fluorophenyl)-1-methyl-1,2,4,9-tetrahydropyrano[3,4-b]pyrazolo[4,3 e]pyridine-3,5 (6H,8H)-dione

Example 26A

Methyl(2-oxopropoxy)acetate

2M Dimethyl zinc in toluene (21 mL, 42 mmol) and trans-benzyl(chloro)bis(triphenylphosphine)palladium(II) (0.57 g, 76 mmol) were treated with methyl 2-(chloroformylmethoxy)acetate (12.6 g, 76 mmol) dropwise over 0.5 hours at 0° C. under a nitrogen atmosphere. After stirring for 0.5 hours at 0° C., the mixture was allowed to warm to ambient temperature and stir for 16 hours. The reaction mixture was treated with 1 M HCl (40 mL) and brine (20 mL). The phases were separated and the organic layer was dried (MgSO$_4$), filtered, and concentrated under reduced pressure. The residue was purified by flash chromatography over silica gel (1:2 ethyl acetate:hexanes) to provide the title compound (5.2 g).

Example 26B 2H-pyran-3,5(4H,6H)-dione

The product from Example 26A (5.0 g, 34 mmol) in diethyl ether (40 mL) was added dropwise over 2.5 hours to a 0° C. solution of 1 M potassium tert-butoxide (in tert-butanol, 34 mL) in diethyl ether (270 mL). The mixture was treated with 1M HCl (120 mL) followed by ethyl acetate (250 mL) and brine (50 mL). The layers were separated and the aqueous layer was extracted with ethyl acetate (2×, 250 mL). The combined organic layers were washed with brine (2×, 60 mL), dried (MgSO$_4$), filtered, and concentrated under reduced pressure (keeping the temperature below 40° C.) to provide the title compound as described in (Terasawa, J. Org. Chem. (1977), 42, 1163–1169) in approximately 30% purity. The title compound can be further purified by chromatography on silica gel using 200:1:1:100 ethyl acetate::formic acid:water:hexane.

Example 26C 4-(3-bromo-4-fluorophenyl 1-methyl-1,2,4,9-tetrahydropyrano[3,4-b]pyrazolo[4,3-e]pyridine-3,5 (6H,8H)-dione 2H-Pyran-3,5(4H,6H)-dione (0.34 g, 3 mmol), 3-bromo-4-fluorebenzaldehyde (0.61 g, 3 mmol), and 5-amino-1-methyl-1,2-dihydropyrazol-3-one (0.34g, 3 mmol) in ethyl alcohol (6 mL) were heated at 80° C. for 2 days in a sealed tube. The reaction mixture was cooled and the resulting precipitate was filtered off to provide 0.55 g (46%) of the title compound as a tan solid. $^1$H NMR (300 MHz, DMSO-d$_6$) δ 3.5 (s, 3H), 4.1 (s, 2H), 4.53 (q, 2H), 4.98 (s, 1H), 7.18 (m, 1H), 7.21 (t, 1H), 7.4 (dd, 1H), 9.65 (bs, 1H), 10.52 (s, 1H); MS (ESI-) m/z 394,392 (M-H)$^-$; Anal. calcd for C$_{16}$H$_{13}$N$_3$BrFO$_3$: C, 49.11;H, 4.35; N, 9.54. Found: C, 49.08; H, 3.83; N, 9.35.

EXAMPLE 27

4-(3-bromo-4-fluorophenyl)-1-ethyl-1,2,4,9-tetrahydropyrano[3,4-b]pyrazolo[4,3-e]pyridine-3,5 (6H,8H)-dione 2H-Pyran-3,5(4H,6H)-dione (0.11 g, 1 mmol), 3-bromo-4-fluorebenzaldehyde (0.2 g, 1 mmol), and 5-amino-1-ethyl-1,2-dihydropyrazol-3-one (0.12g, 1 mmol) were processed as described in Example 26C to provide 0.1 g of the title compound. $^1$H NMR (300 MHz, DMSO-d$_6$) δ 1.2 (t, 3H), 3.82 (q ,2H), 3.99 (s, 2H), 4.52 (q, 2H), 4.96 (s, 1H), 7.18 (m, 1H), 7.21 (t, 1H), 7.39 (dd, 1H), 9.65 (bs, 1H), 10.52 (s, 1H); MS (ESI) m/z 406 (M-H)$^-$; Anal. calcd for C$_{17}$H$_{15}$N$_3$BrFO$_3$.0.5 C$_2$H$_5$OH: C, 50.13;H, 4.21; N, 9.74. Found: C, 49.94;H, 3.96; N, 9.21.

EXAMPLE 28

4-(4-fluoro-3-iodophenyl)-1-methyl-1,2,4,9-tetrahydropyrano[3,4-b]pyrazolo[4,3-e]pyridine-3,5 (6H,8H)-dione 2H-Pyran-3,5(4H,6H)-dione (0.085 g, 0.75 mmol), 3-iodo-4-fluoro-benzaldehyde (0.182 g, 0.75 mmol) and 5-amino-1-methyl-1,2-dihydropyrazol-3-one (0.084g, 0.75 mmol) were processed as described in Example 26C to provide 0.23 g of the title compound. $^1$H NMR (300 MHz, DMSO-d$_6$) δ 3.5 (s, 3H), 4.0 (s, 2H), 4.52 (q, 2H), 4.92 (s, 1H), 7.1 (t, 1H), 7.18 (m, 1H), 7.55 (dd, 1H), 9.62 (bs, 1H), 10.1 (s, 1H); MS (ESI-) m/z 440 (M-H)$^-$; Anal. calcd for C$_{16}$H$_{13}$N$_3$FIO$_3$.C$_2$H$_5$OH: C, 44.37;H, 3.93; N, 8.62. Found: C, 44.38;H, 3.89; N, 8.74.

EXAMPLE 29

4-(3-iodo-4-methylphenyl)-1-methyl-1,2,4,9-tetrahydropyrano[3,4-b]pyrazolo[4,3-e]pyridine-3,5 (6H,8H)-dione 2H-Pyran-3,5(4H,6H)-dione (0.085 g, 0.75 mmol), 3-iodo4-methyl-benzaldehyde (0.18 g, 0.75 mmol), and 5-amino-1-methyl-1,2-dihydropyrazol-3-one (0.084 g, 0.75 mmol) were processed as described in Example 26C to provide 0.14 g of the title compound. $^1$H NMR (300 MHz, DMSO-d$_6$) δ 2.38 (s, 3H), 3.49 (s, 3H), 4.0 (s, 2H), 4.52 (q, 2H), 4.88 (s, 1H), 7.05 (dd, 1H), 7.16(d, 1H), 7.56 (d, 1H), 9.58 (bs, 1H), 10.03 (s, 1H); MS (ESI-) m/z 436 (M-H)$^-$; Anal. calcd for C$_{17}$H$_{16}$N$_3$IO$_3$.0.5 C$_2$H$_5$OH: C, 46.97;H, 4.16; N, 9.13. Found: C, 46.60;H, 4.42; N, 9.32.

EXAMPLE 30

4-(4-bromo-3-chlorophenyl)-1-methyl-1,2,4,9-tetrahydropyrano[3,4-b]pyrazolo[4,3-e]pyridine-3,5 (6H,8H)-dione 2H-Pyran-3,5(4H,6H)-dione (0.057 g, 05 mmol), 3-chloro4-bromo-benzaldehyde (0.11 g, 0.5 mmol), and 5-amino-1-methyl-1,2-dihydropyrazol-3-one (0.056g, 0.5 mmol) were processed as described in Example 26C to provide 0.145 g of the title compound. $^1$H NMR (300 MHz, DMSO-d$_6$) δ 3.5 (s, 3H), 4.0 (s, 2H), 4.52 (q, 2H), 4.92 (s, 1H), 7.03 (dt, 1H), 7.32(t, 1H), 7.6 (dd, 1H), 9.62 (s, 1H), 10.1 (s, 1H); MS (ESI-) m/z 410 (M-H:) Anal. calcd for C$_{16}$H$_{13}$N$_3$BrClO$_3$: C, 46.80;H,3.19; N, 10.23. Found: C, 46.77;H, 3.43; N, 10.27.

EXAMPLE 31

4-(3-bromo-4-fluorophenyl)-1-methyl-1,2,4,7,8,9-hexahydropyrano[4,3-b]pyrazolo[4,3-e]pyridine-3,5-dione

Example 31A 4-(1-ethoxyethoxy)-1-butyne

3-Butyn-1-ol (46.33 g, 0.661 mole) in methylene chloride (700 mL) was treated with ethyl vinyl ether (0.661 mole, 63.2 mL) and pyridinium p-toluenesulfonate (0.033, 8.31 g) (note: upon addition of pyridinium p-toluenesulfonate an exothermic reaction takes place). After stirring 2 hours, the reaction mixture was concentrated and filtered through a pad of silica gel (ethyl acetate:hexane, 1:1) to provide the title compound as a colorless liquid (80.29 g, 85.5%).

Example 31B benzyl 5-(1-ethoxyethoxy)-2-pentynoate

The product from Example 31 A (79.99 g, 0.563 mole) in tetrahydrofuran (1 L) was treated dropwise at −78° C. with n-butyllithium (2.5 M in hexane, 0.563 mole, 225 mL). The reaction mixture was stirred at −78° C. for 30 minutes and then benzyl chloroformate (0.563 mole, 80.4 mL) was added dropwise. The reaction mixture was stirred at −78° C. for 2 hours, allowed to warm to ambient temperature and stirred overnight. After quenching with water, ethyl acetate was added and the layers were separated. The organic layer was dried over magnesium sulfate, filtered and concentrated. Flash chromatography of the residue (silica, hexane to hexane:ethyl acetate, 30:1 to 4:1) provided the title compound as a colorless oil (155.5 g, 78%).

Example 31C benzyl 5-hydroxy-2-pentynoate

A solution of the product from Example 31B (122.1 g, 0.442 mole) in acetone (400 mL) was treated at ambient temperature with an aqueous hydrochloric acid solution (0.5 N, 200 mL). The reaction mixture was stirred for 6 hours and then diluted with water and ethyl acetate. The layers were separated, and the organic layer was dried over magnesium sulfate, filtered and concentrated to provide the title compound as a colorless oil (90.17 g, 100%). $^1$H NMR (300 MHz, CDCl$_3$) δ 2.61 (t, 2H), 3.79 (t, 2H), 5.19 (s, 2H), 7.32–7.40 (m, 5H).

Example 31D 4-(benzyloxy)-5,6-dihydro-2H-pyran-2-one

A heterogeneous mixture of benzyl alcohol (2.65 mole, 274.4 mL), mercury (II) oxide (red) (13.26 mmol, 2.87 g) and boron trifluoride diethyl etherate (0.133 mole, 16.3 mL) was heated at 60° C. for 3 hours (eventually turned homogeneous). A solution of the product from Example 31 C (90.17 g, 0.442 mole) in benzyl alcohol (91.5 mL) was added at ambient temperature, and the reaction mixture was stirred at 70° C. for 4 hours and again at ambient temperature overnight. It was poured into an aqueous saturated sodium bicarbonate solution and extracted with ethyl acetate. The organic layer was dried over magnesium sulfate, filtered and concentrated. The residue was purified via flash chromatography (silica, hexane to hexane:ethyl acetate, 30:1 to 1:2) to provide the title compound as a white solid (49.6 g, 55%).

$^1$H NMR (300 MHz, CDCl$_3$) δ 2.60 (t, 2H), 4.38 (t, 2H), 4.95 (s, 2H), 5.28 (s, 1H), 7.32–7.46 (m, 5H).

Example 31E dihydro-2H-pyran-2,4(3H)-dione

The product from Example 31D (9.17 g, 0.045 mole) was dissolved in isopropanol (500 mL) and treated with palladium hydroxide (20 wt. % palladium, dry basis, on carbon) (4 g). The reaction mixture was stirred under a hydrogen atmosphere at atmospheric pressure overnight, filtered through a pad of silica gel (elution with ethyl acetate), and concentrated to provide the title compound as a white solid (4.28 g, 84%).

$^1$H NMR (300 MHz, CDCl$_3$) δ 2.73 (t, 2H), 3.57 (s, 2H), 4.61 (t, 2H).

Example 31F 4-(3-bromo-4-fluorophenyl)-1-methyl-1,2,4,7,8,9-hexahydropyrano[4,3-b]pyrazolo[4,3-e]pyridine-3,5-dione Dihydro-2H-pyran-2,4(3H)-dione(0.11 g, 1 mmol), 3-bromo-4-fluoro-benzaldehyde (0.2 g, 1 mmol) and 5-amino-1-methyl-1,2-dihydropyrazol-3-one (0.12g, 1 mmol) were processed as described in Example 26C to provide 0.27 g of the title compound. $^1$H NMR (300 MHz, DMSO-d$_6$)δ 2.55 (m, 1H), 2.8 (m, 1H), 3.5 (s, 3H), 4.22 (m, 2H), 4.86 (s, 1H), 7.2 (m, 2H), 7.41 (dd, 1H), 9.49 (s, 1H), 9.92 (s, 1H); MS (ESI−) m/z 392 (M−H$^-$) Anal. Calcd for C$_{16}$H$_{13}$N$_3$BrFO$_3$.C$_2$HO: C, 49.11;H, 4.35; N, 9.54. Found: C, 48.87;H, 4.24; N, 9.40.

EXAMPLE 32

4-(3-bromo-4-fluorophenyl)-1-methyl-4,8-dihydro-1H-furo[3,4-b]pyrazolo[4,3e]pyridine-3,5(2H,7H)-dione

Example 32A ethyl 6-[(acetyloxy)methyl]-4-(3-bromo-4-fluorophenyl)-1-methyl-3-oxo-2,3,4,7-tetrahydro-1H-pyrazolo[3,4-b]pyridine-5-carboxylate Ethyl 4-(acetyloxy)-3-oxobutanoate (0.19 g, 1 mmol), prepared as described in (S. Husband, W. Fraser, C. J. Suckling, H. C. Wood, Tetrahedron, (1995) 51(3), 865), 3-bromo-4-fluorobenzaldehyde (0.2 g, 1 mmol) and 5-amino-1-methyl-1,2-dihydropyrazol-3-one (0.11 g, 1 mmol) in ethyl alcohol (3 mL) were heated at 80° C. for 24 hours in a sealed tube. The reaction mixture was evaporated under reduced pressure and chromatographed on silica gel eluting with 5% ethanol/methylene chloride to provide 0.1 g of the title compound. $^1$H NMR (300 MHz, DMSO-d$_6$) δ 1.03 (t, 3H), 2.1 (s, 3H), 3.46 (s, 3H), 3.92 (q, 2H), 4.95 (s, 1H), 5.12 (q, 2H), 7.18 (m, 1H), 7.22 (t, 1H), 7.38 (dd, 1H), 9.43 (s, 1H); MS (ESI−) m/z 468(M−H)$^-$.

Example 32B 4-(3-bromo-4-fluorophenyl)-1-methyl-4,8-dihydro-1H-furo[3,4-b]pyrazolo[4,3-e]pyridine-3,5(2H,7H)-dione The product from Example 32A (0.09 g) and potassium carbonate(0.03 g) in methanol (10 mL) were stirred at ambient temperature for 1 hour. The solvent was evaporated under reduced pressure and the obtained residue was chromatographed on silica gel eluting with 10% EtOH/CH$_2$Cl$_2$ to provide 0.04 g of the title compound. $^1$H NMR (300 MHz, DMSO-d$_6$) δ 3.49 (s, 3H),4.76 (s, 1H),4.9 (q, 2H), 7.23 (m, 2H), 7.42 (dd, 1H), 9.51 (bs, 1H), 9.78 (s, 1H)

MS (ESI-) m/z 378 (M-H)$^-$; Anal. calcd for C$_{15}$H$_{11}$N$_3$BrFO$_3$.0.5 C$_2$H$_6$P: C, 47.66;H, 3.50; N, 10.42. Found: C, 48.10;H, 2.97; N, 10.04.

EXAMPLE 33

(4-(3-bromo-4-fluorophenyl)-1-methyl-1,2,4,6,7,8-hexahydrocyclopenta[b]pyrazolo[4,3-e]pyridine-3,5-dione Example 33A 4-(3-bromo-4-fluorophenyl)-1-methyl-5-oxo-1,4,5,6,7,8-hexahydrocyclopenta[b]pyrazolo[4,3-e]pyridin-3-yl acetate The product from Example 1 (0.4 g) was heated on a steam bath in acetic anhydride (5 mL) for 15 minutes. The reaction mixture was evaporated under reduced pressure and the residue was chromatographed on silica gel eluting with 5% ethanol/methylene chloride to provide a less polar compound (0.27 g) and a more polar compound (0.07 g). The less polar compound was determined to be the title compound. $^1$H NMR (300 MHz, DMSO-d$_6$) δ 2.35 (t, 2H), 2.36 (s, 3H), 2.74 (m, 2H), 3.35 (s, 3H), 4.59 (s, 1H), 7.25 (d, 2H),), 7.55 (d, 1H), 11.0 (s, 1H); MS (ESI—) m/z 423 (M-H)$^-$.

Example 33B (+) 4-(3-bromo-4-fluorophenyl)-1-methyl-1,2,4,6,7,8-hexahydrocyclopenta[b]pyrazolo[4,3-e]pyridine-3,5-dione The title compound from Example 33A (0.4 g) was chromatographed on a chiral column (Chiracel OJ 4.6×250 mm using 75:25 hexane:ethanol at ImL/min) to provide two products. Product A had a retention time of 10.9 minutes (0.174 g). Product B had a retention time of 18.4 minutes (0.16 g).

Product A (0.17 g), retention time of 10.9 minutes from above, in aqueous methanol (10 mL) was treated with 6N HCl (1 mL) and then heated at reflux for 1 hour. The reaction mixture was evaporated under reduced pressure and the residue was chromatographed eluting with 15% ethanol/methylene chloride to provide 0.09 g of the title compound. $[α]^{23}_D$+168. 1° (DMSO); $^1$H NMR (DMSO-d$_6$) δ 2.3 (t, 2H), 2.7 (m, 2H), 3.5 (s, 3H), 4.7 (s, 1H), 7.18 (m, 1H), 7.2 (t, 1H), 7.39 (dd, 1H), 9.51 (bs, 1H), 10.42(s, 1H); MS (ESI-) m/z 378 (M-H)$^-$; Anal. calcd for C$_{16}$H$_{13}$N$_3$BrFO$_2$: C, 50.81;H, 3.46; N, 11.11. Found: C, 50.35;H, 3.23; N, 11.08.

EXAMPLE 34

(-) 4-(3-bromo-4-fluorophenyl)-1-methyl 1,2,4,6,7,8-hexahydrocyclopenta[b]pyrazolo[4,3-e]pyridine-3,5-dione Product B from Example 33B (0. 16 g), retention time 18.4 minutes, in aqueous methanol (10 mL) was treated with 6N HCl (1 mL) and then heated at reflux for 1 hour. The reaction mixture was evaporated under reduced pressure and the residue was chromatographed eluting with 15% ethanol/methylene chloride to provide 0.09 g of the title compound. $[αα]^{23}_D$ 166.70 (DMSO); $^1$H NMR (DMSO-d$_6$) δ 2.3 (t, 2H), 2.7 (m, 2H), 3.5 (s, 3H), 4.7 (s, 1H), 7.18 (m, 1H), 7.2 (t, 1H), 7.39 (dd, 1H), 9.51 (bs, 1H), 10.42(s, 1H); MS (ESI-) m/z 378 (M-H;)$^-$ Anal. calcd for C$_{16}$H$_{13}$N$_3$BrFO$_2$: C, 50.81;H, 3.46; N, 11.11. Found: C, 50.82;H, 3.74; N, 10.75.

EXAMPLE 35

2-acetyl-4-(3-bromo-4-fluorophenyl)-1-methyl-1,2,4,6,7,8-hexahydrocyclopenta[b]pyrazolo[4,3-e]pyridine-3,5-dione The title compound was obtained as the more polar compound isolated from the chromatography described in Example 33A. $^1$H NMR (300 MHz, DMSO-d$_6$) δ 2.05 (s, 3H), 2.31 (t, 2H), 2.74 (m, 2H), 3.65 (s, 3H), 4.65 (s, 1H), 7.1 (m, 1H), 7.22 (t, 1H), 7.35 (dd, 1H), 10.7 (s, 1H); MS (ESI-) m/z 423 (M-H)$^-$ Anal. Calcd for C$_{18}$H$_{15}$N$_3$BrFO$_3$: C, 51.45;H, 3.60; N, 10.00. Found: C, 51.43;H, 3.61; N, 9.82.

EXAMPLE 36

(+) 4-(3-bromo-4-fluorophenyl)-1,6,6-trimethyl-4,7,8,9-tetrahydro-1H-pyrazolo[3,4-b]quinoline-3,5(2H,6H)-dione Example 36A 4-(3-bromo-4-fluorophenyl)-1,6,6-trimethyl-5-oxo-4,5,6,7,8,9hexahydro-1H-pyrazolo[3,4-b]quinolin-3-yl acetate The product from Example 22 (0.6 g) in 5 mL of acetic anhydride was heated for 10 minutes on a steam bath. The reaction mixture was evaporated under reduced pressure and chromatographed on silica gel to provide a less polar (0.36 g) compound and a more polar compound (0.15 g). The less polar compound was determined to be the title compound.

Example 36B (+) 4-(3-bromo-4-fluorophenyl)-1,6,6-trimethyl-4,7,8,9-tetrahydro-1H-pyrazolo[3,4-b]quinoline-3,5(2H,6H)-dione The title compound from Example 36A (0.36g) was chromatographed on a chiral column (Chiracel OJ column 4.6×250 mm using hexane:ethanol (85:15) at 1 mL/min) to provide two products. Product A had a retention time of 7.63 minutes (0.14 g). Product B had a retention time of 10.18 minutes (0.14 g).

Product A (0.14 g), retention time 7.63 minutes from above, in aqueous methanol (10 mL) was treated with 6N HCl (1 mL) and heated at reflux for 2 hours. The reaction mixture was evaporated under reduced pressure and chromatographed on silica gel eluting with 10% ethanol/methylene chloride to provide 0.09 g of the title compound. $[α]^{23}_D$+25.3° (DMSO); $^1$H NMR (DMSO-d$_6$) δ 0.92 (s, 3H), 0.98 (s, 3H), 1.78 (t, 2H), 2.63 (m, 2H), 3.44 (s, 3H), 4.83 (s, 1H), 7.12 (m, 1H), 7.16 (t, 1H), 7.33 (dd, 1H), 9.52 (bs, 1H), 9.63 (s, 1H); MS (ESI-) m/z 420 (M-H)$^-$; Anal. Calcd for C$_{19}$H$_{19}$N$_3$BrFO$_2$: C, 54.30;H, 4.56; N, 10.00. Found: C, 53.95;H, 4.45; N, 9.63.

EXAMPLE 37

(-) 4-(3-bromo-4-fluorophenyl)-1,6,6-trimethyl4,7,8,9-tetrahydro-1H-pyrazolo[3,4-b]quinoline-3,5(2H,6H)-dione Product B from Example 36B(0.16 g), retention time 10.18 minutes, was treated with 6N HCl (1 mL) and then heated at reflux for 1 hour. The reaction mixture was evaporated under reduced pressure and the residue was chromatographed eluting with 15% ethanol/methylene chloride to provide 0.08 g of the title compound. $[\alpha]^{23}_D$ –23.9° (DMSO); $^1$H NMR (DMSO-d$_6$) δ 0.92 (s, 3H), 0.98 (s, 3H), 1.78 (t, 2H), 2.63 (m, 2H), 3.44 (s, 3H), 4.83 (s, 1H), 7.12 (m, 1H), 7.16 (t, 1H), 7.33 (dd, 1H), 9.52 (bs, 1H), 9.63 (s, 1H); MS (ESI–) m/z 420 (M–H)$^-$; Anal. Calcd for $C_{19}H_{19}N_3BrFO_2$: C, 54.30;H, 4.56; N, 10.00. Found: C,54.17; H, 4.49; N, 9.95.

EXAMPLE 38

2-acetyl-4-(3-bromo-4-fluorophenyl)-1,6,6-trimethyl-4,7,8,9-tetrahydro-1H-pyrazolo[3,4-b]quinoline-3,5(2H,6H)-dione The title compound was obtained as the more polar compound isolated from the chromatography described in Example 36A. $^1$H NMR (DMSO-d$_6$) δ 0.89 (s, 3H), 0.97 (s, 3H),1.79 (t, 2H), 2.13 (s, 3H),2.68 (m, 2H) 3.61 (s, 3H), 4.78 (s, 1H), 7.06 (m, 1H), 7.19 (t, 1H), 7.28 (dd, 1H), 9.38 (s, 1H); MS (ESI–) m/z 460 (M–H)$^-$; Anal. Calcd for $C_{21}H_{21}N_3BrFO_3$: C, 54.54;H, 4.54; N, 9.09. Found: C, 54.57;H, 4.49; N, 8.80.

EXAMPLE 39

4-(3-bromo-4-fluorophenyl)-2-(methoxycarbonyl)-1-methyl-1,2,4,6,7,8-hexahydrocyclopentafblpyrazolo[4,3-e]pyridine-3,5-dione The product from Example 1 (0.1 g) in methylene chloride (10 mL) was stirred overnight with methyl chloroformate (0.04 mL) and pyridine (0.06 mL). The reaction mixture was evaporated under reduced pressure and the residue was chromatographed on silica gel eluting with 5% ethanol/methylene chloride to provide 0.038 g of the title compound. $^1$H NMR (DMSO-d$_6$) δ 2.32 (t, 2H), 2.72 (m, 2H), 3.65 (s, 3H), 3.7 (s, 3H), 4.72 (s, 1H), 7.11 (m, 1H), 7.22 (t, 1H), 7.32 (dd, 1H), 10.80 (s, 1H); MS (ESI+) m/z 438 (M+H$^+$); Anal. Calcd for $C_{18}H_{15}N_3BrFO_4$: C, 49.54;H, 3.44; N, 9.63. Found: C, 49.69;H, 3.27; N, 9.72.

EXAMPLE 40

4-(4-bromo-3-chlorophenyl)-1-methyl-1,2,4,6,7,8-hexahydrocyclopenta[b]pyrazolo[4,3-e]pyridine-3,5-dione

Example 40A 4-bromo-3-nitrobenzaldehyde

A suspension of sodium nitrate (1.37 g, 16.2 mmol) in concentrated sulfuric acid (15 mL) was stirred at 10° C. until a homogeneous solution was obtained. The solution was treated with 4-bromobenzaldehyde (2.50 g, 13.5 mmol) in portionwise fashion over a 20 minute period. The mixture was poured onto ice (50 g) and the resulting pale yellow precipitate was collected by filteration. The precipitate was washed with copious amounts of water and then dried at 30° C. under reduced pressure to provide the title compound (2.95 g, 12.8 mmol, 95%) as a pale yellow solid. MS (DCI/NH$_3$) m/e 229 (M+H)$^+$.

Example 40B 3-amino-4-bromobenzaldehyde

The product from Example 40A (992 mg, 4.31 mmol) in CHCl$_2$ at 23° C. (6 mL) was treated with water (1.5 mL) and N,N'-diheptyl-4,4bipyridinium dibromide (43 mg, 10 mg/mmol of substrate) as described in (Park, K. K.; Oh, C. H.; Joung, W. K. Tetrahedron Lett. (1993) 34, 7445–7446). The biphasic mixture was cooled to 5° C. and treated with a solution of sodium dithionite (3.00 g, 17.2 mmol) and $K_2CO_3$ (2.68 g, 19.4 mmol) in water (3.5 mL). The cooling bath was removed and the biphasic mixture stirred vigorously at 23° C. for 4 hours. The mixture was partitioned between additonal $CH_2Cl_2$ (15 mL) and water (10 mL) and the phases separated. The aqueous layer was extracted with $CH_2Cl_2$ (10 mL). The organic fractions were combined, washed with brine (10 mL), and dried (Na$_2$SO$_4$). Ethyl acetate (5 mL) was added along with silica gel (5 g) and the suspension was filtered through a small pad of Celite, rinsing with 10% EtOAc/CH$_2$Cl$_2$ (15 mL). The filtrate was concentrated to provide the title compound (716 mg, 3.58 mmol, 82%) as an off-yellow powder. MS (DCI/NH$_3$) m/e 218 (M+NH$_4$)$^+$.

Example 40C 4-bromo-3-chlorobenzaldehyde

The product from Example 40B (1.97 g, 9.85 mmol) in concentrated HCl (20 mL) at 0° C. was treated with NaNO$_2$ (714 mg, 10.3 mmol). After stirring for 30 minutes, the mixture was transferred cold in portionwise fashion by dropping pipet to a stirred solution of CuCl (1.37 g, 13.8 mmol) in concentrated HCl (15 mL) at 23° C. (significant frothing!). The line green solution was heated at 60° C. for 45 minutes, cooled, and diluted with ethyl acetate (200 mL) and water (50 mL). The phases were separated and the organic portion was washed in succession with water (4×50 mL), aqueous NaHCO$_3$ (2×60 mL), brine (100 mL), dried (Na$^2$SO$_4$) and concentrated. The residue was purified by flash chromatogrpahy (elution with 10% EtOAc/hexanes) to provide the title compound (1.45 g, 6.59 mmol, 68%) as a waxy, off-white solid.

Example 40D 4-(4-bromo-3-chlorophenyl)-1-methyl-1,2,4,6,7,8-hexahydrocyclopenta[b]pyrazolo[4,3-e]pyridine-3,5-dione 5-Amino-1-methyl-1,2-dihydropyrazol-3-one (0.84 g, 0.75 mmol), 4bromo-3-chlorobenzaldehyde (0.157 g, 0.75 mmol) from Example 40C, and 1,3-cyclopentanedione (0.074 g, 0.75 mmol) was processed as described in Example 1 to provide 0.20 g of the title compound. $^1$H NMR (DMSO-d$_6$) δ 2.29 (t, 2H), 2.68 (m, 2H), 3.49 (s, 3H), 4.69 (s, 1H), 7.02 (dd, 1H), 7.33 (d, 1H), 7.6 (d, 1H), 9.55 (s, 1H), 10.41 (s, 1H); MS (ESI–) m/z 394 (M–H)$^-$; Anal. Calcd for $C_{16}H_{13}N_3BrClO_2$: C, 48.66;H, 3.29; N, 10.64. Found: C, 48.92;H, 3.13; N, 10.72.

EXAMPLE 41

4-(4-bromo-3-chlorophenyl)-1,6,6-trimethyl-4,7,8,9-tetrahydro-1H-pyrazolo[3,4-b]quinoline-3,5(2H,6H)-dione 5-Amino-1-methyl-1,2-dihydropyrazol-3-one (0.08 g, 0.75 mmol), 3-chloro-4-bromobenzaldehyde (0.13 g, 0.75 mmol) from Example 40C, and 4,4dimethyl-1,3-cyclohexanedione (0.10 g, 0.75 mmol) were processed as described in Example 22 to provide the title compound (0.22 g, 67%). $^1$H NMR (DMSO-d$_6$) δ 0.92 (s, 3H), 0.98 (s, 3H), 1.78 (t, 2H), 2.55 (m, 2H), 3.47 (s, 3H), 4.81 (s, 1H), 7.0 (dd, 1H), 7.29 (d, 1H), 7.55 (d, 1H), 9.52 (bs, 1H), 9.67 (s, 1H); MS (ESI−) m/z 436 (M−H)−; Anal. Calcd for $C_{19}H_{19}N_3BrClO_2$: C, 52.23; H, 4.35; N, 9.62. Found: C, 52.35;H, 4.24; N, 9.62.

EXAMPLE 42

2-acetyl-4-(3-bromo-4-fluorophenyl)-1-methyl-1,2, 4,9-tetrahydropyrano[3,4-b]pyrazolo[4,3-e]pyridine-3,5(6H,8H)-dione The product from Example 26C (0.1 g) was heated for 15 minutes on a steam bath with 5 mL of acetic anhydride. The reaction mixture was evaporated under reduced pressure and the residue was chromatographed on silica gel eluting with 5% ethanol/methylene chloride to provide 0.035 g of the title compound as the more polar compound. $^1$H NMR (DMSO-$d_6$) δ 2.12 (s, 3H), 3.55 (s, 3H), 4.0 (m, 2H), 4.56 (q, 2H), 4.89 (s, 1H), 7.15 (m, 1H), 7.22 (t, 1H), 7.35 (dd, 1H), 10.18 (s, 1H); MS (ESI−) m/z 436 (M−H)−; Anal. Calcd for $C_{18}H_{15}N_3BrFO_4$: C, 49.58;H, 3.47; N, 9.63. Found: C, 49.31;H, 3.32; N, 9.62.

EXAMPLE 43

4-(3-bromo-4-fluorophenyl)-1,6,6-trimethyl-1,2,4,9-tetrahydropyrano[3,4-b]pyrazolo[4,3-e]pyridine-3,5 (6H,8H)-dione

Example 43A

Methyl[(1,1-dimethyl-2-propynyl)oxy]acetate

A mechanically stirred suspension of sodium hydride (60% dispersion in mineral oil, 10.0 g, 0.25 mol) in THF (170 mL) at 0° C. under $N_2$ gas was treated with 2-methyl-3-butyn-2-ol (29.1 mL, 0.30 mol) in THF (70 mL) dropwise. After stirring at 0° C. for 1 hour, the reaction mixture was treated with methyl bromoacetate (35.5 mL, 0.38 mol) in THF (100 mL). After stirring at ambient temperature overnight, the mixture was quenched into 1 M HCl (300 mL) and extracted with ethyl acetate (3×300 mL). The organic layers were combined, dried over $Na_2SO_4$, and concentrated to half the volume. The residue was distilled by vacuum distillation (bp. 118–120° C./20 mmHg) to provide the tittle compound (10.0 g). $^1$H NMR (CDCl$_3$) δ 1.52 (s, 6H), 2.47 (s, 1H), 3.77 (s, 3H), 4.25 (s, 2H).

Example 43B methyl (1,1-dimethyl-2-oxopropoxy)acetate

A solution of the product from Example 43A (10.0 g, 64 mmol) in methanol (320 mL) was treated with mercury (II) acetate (2.0 g, 6.4 mmol) and sulfuric acid (0.5 mL). After heating the reaction mixture at reflux for 1.5 hours, the mixture was allowed to cool to ambient temperature and then concentrated to a volume of 100 mL. The reaction mixture was poured into 1N HCl (300 mL) and extracted with dichloromethane (3×300 mL). The organic layers were combined, washed with NaHCO$_3$, washed with brine, dried over Na$_2$SO$_4$, and concentrated to provide the title compound (10.3 g). $^1$H NMR (CDCl$_3$) δ 1.34 (s, 6H), 2.25 (s, 3H), 3.76 (s, 3H), 4.01 (s, 2H).

Example 43C 2,2-dimethyl-2H-pyran-3,5(4H,6H)-dione

Potassium tert-butoxide (1M in tert-butanol, 12.1 mL, 12.1 mmol) in ether (7.5 mL) at 0° C. under N$_2$ gas was treated with the product from Example 43B in ether (3 mL). After 10 minutes, the reaction mixture was quenched into 2N HCl (25 mL) and extracted with ether (3×25 mL). The organic layers were combined, washed with brine, dried over Na$_2$SO$_4$, concentrated to an oil, treated with 10% dichloromethane in hexane (5 mL), and placed in the freezer for 1 hour. The resulting crystals were collected by filtration, washed with a cold solution of 10% dichloromethane in hexane, and dried to provide the title compound (431 mg). $^1$H NMR (CDCl$_3$) δ 1.25 (s, 6H), 4.16 (s, 2H), 5.20 (s, 1H), 11.70 (s, 1H).

Example 43D 4-(3-bromo-4-fluorophenyl)-1,6,6-trimethyl-1,2,4,9-tetrahydropyrano[3,4-b]pyrazolo[4,3-e]pyridine-3,5 (6H,8H)-dione 5-Amino-1-methyl-1,2-dihydropyrazol-3-one (339 mg, 3.0 mmol), 3-bromo-4-fluorobenzaldehyde (627 mg, 3.0 mmol), and the product from Example 43C (426 mg, 3.0 mmol) were processed as described in Example 22 to provide the title compound.
$^1$H NMR (DMSO) δ 1.15 (s, 3H), 1.25 (s, 3H), 3.47 (s, 3H), 4.55 (s, 2H), 4.88 (s, 1H), 7.19 (m, 2H), 7.38 (d, 1H), 9.60 (s, 1H), 9.99 (s, 1H); MS (APCI+) m/z 422 (M+H)$^+$; Anal. Calcd for $C_{18}H_{17}BrFN_3O_3$: C, 51.20;H, 4.06; N, 9.95. Found: C, 51.52;H, 4.1 1; N, 10.04.

EXAMPLE 44

4-(3-bromo-4-fluorophenyl)-1,6-dimethyl-1,2,4,9-tetrahydropyrano[3,4b]pyrazolo[4,3-e]pyridine-3,5 (6H,8H)-dione

Example 44A methyl[(1-methyl-2-propynyl)oxy]acetate

Sodium hydride (60% dispersion in mineral oil, 10 g, 0.25 mol), (±)-3-butyn-2-ol (21 g, 0.30 mol), and methyl bromoacetate were processed as described in Example 43A to provide the title compound. $^1$H NMR (CDCl$_3$) δ 1.51 (d, 3H), 2.46 (d, 1H), 3.76 (s, 3H), 4.25 (AB q, 2H), 4.39 (dq, 1H).

Example 44B methyl (1-methyl-2-oxopropoxy)acetate

The product from Example 44A (20 g, 0.14 mol) and mercury (II) acetate (4.6 g, 0.014 mol) were processed as described in Example 43B to provide the title compound. $^1$H NMR (CDCl$_3$) δ 1.37 (d, 3H), 2.31 (s, 3H), 3.76 (s, 3H), 3.96 (q, 1H), 4.15 (AB q, 2H).

Example 44C 2-methyl-2H-pyran-3,5(4H,6H)-dione

Potassium tert-butoxide in tert-butanol (1 M, 203 mL) and the product from Example 44B (15.5 g, 97 mmol) in ether (55 mL) were processed as described in Example 43C. The residue was purified on silica gel eluting with ethyl acetate-:formic acid:water:hexane (200:1:1:200) provided the title compound. $^1$H NMR (CDCl$_3$) δ 1.48 (d, 3H), 3.43 (d, 1H), 3.92 (d, 1H), 3.97 (q, 1H), 4.04 (d, 1H), 4.44 (d, 1H).

Example 44D 4-(3-bromo-4-fluorophenyl)-1,6-dimethyl-1,2,4,9-tetrahydropyrano[3,4-b]pyrazolo[4,3-e]pyridine-3,5 (6H,8H)-dione 5-Amino-1-methyl-1,2-dihydropyrazol-3-one, 3-bromo-4-fluorobenzaldehyde, and the product from Example 44C could be processed as described in Example 22 to provide the title compound.

EXAMPLE 45

4-(3-bromo-4-fluorophenyl)-1-methyl)-4,9-dihydro-1H-isoxazolo[3,4-b]pyrano[4,3-e]pyridine-3,5(6H,8H)-dione

Example 45A 3-amino-2-methyl-5(2H)-isoxazolone

Sodium spheres (1.15 g) were dissolved in ethanol (100 mL) and the resulting solution of sodium ethoxide was treated with methylhydroxylamine hydrochloride (4.2 g) and ethylcyanoacetate(5.65 g). After refluxing for 5 hours, the mixture was filtered and the filtrate was evaporated under reduced pressure. The residue was chromatographed on silica gel eluting with 5% ethanol/dichloromethane to provide the title compound as a solid (12 g). $^1$H NMR (300 MHz, DMSO-$d_6$) δ 3.08 (s, 3H), 4.13 (s, 1H), 7.05 (s, 2H).

Example 45B 4-(3-bromo-4-fluorophenyl)-1-methyl)-4,9-dihydro-1H-isoxazolo[3,4-b]pyrano[4,3-e]pyridine-3,5(6H,8H)-dione The product from Example 45A (0.11 g, 1 mmol), 3-bromo-4-fluorobenzaldehyde(0.2 g, 1 mmol), and 2H-pyran-3,5(4H,6H)-dione (0.11 g, 1 mmol) in ethyl alcohol (3 mL) were heated at 80° C. for 2 days in a sealed tube. The reaction mixture was allowed to cool to ambient temperature and was evaporated under reduced pressure. The residue was chromatographed eluting with 5% ethanol/dichloromethane to provide the title compound as a white solid (0.09 g). $^1$H NMR (300 MHz, DMSO-$d_6$) δ 3.27 (s, 3H), 4.05 (s, 2H), 4.57 (q, 2H), 4.78 (s, 1H), 7.28 (m, 2H), 7.54 (d, 1H), 10.77 (s, 1H); MS (ESI) m/z 395 (M−H)$^-$; Anal. Calcd for $C_{16}H_{12}BrFN_2O_4$: C, 48.63;H, 3.06; N, 7.09. Found: C, 48.70;H, 3.28; N, 6.79.

EXAMPLE 46

4-(3-bromo-4-fluorophenyl)-1,6,6-trimethyl-4,7,8,9-tetrahydroisoxazolo[3,4-b]quinoline-3,5(1H,6H)-dione The product from Example 45A (0.11 g, 1 mmol), 3-bromo-4-fluorebenzaldehyde(0.2 g, 1 mmol), and 4,4-dimethyl 1,3-cyclohexanedione (0.11 g, 1 mmol) in ethyl alcohol (3 mL) were heated at 80° C. for 2 days in a sealed tube. The reaction mixture was allowed to cool to ambient temperature and evaporated under reduced pressure. The residue was chromatographed eluting with 5% ethanol/dichloromethane to yield 0.130 g of the title compound as a white solid. $^1$H NMR (300 MHz, DMSO-$d_6$) δ 0.92 (s, 3H), 1.0 (s, 3H), 1.82 (t, 2H), 2.65 (m, 2H), 3.22 (s, 3H), 4.67 (s, 1H), 7.21 (m, 2H), 7.43 (dd, 1H), 10.39 (s, 1H);
MS (ESI) m/z 419,421 (M−H)$^-$; Anal. Calcd for $C_{19}H_{18}BrFN_2O_3$: C, 54.15;H, 4.27; N, 6.65. Found: C, 54.19;H, 4.39; N, 6.60.

EXAMPLE 47

4-(3-bromo-4-fluorophenyl)-1-methyl-4,8-dihydro-1H,3H-furo[3,4-b]isoxazolo[4,3-e]pyridine-3,5(7H)-dione

Example 47A ethyl 6-[(acetyloxy)methyl]-4-(3-bromo-4fluorophenyl)-1-methyl-3-oxo-1,3,4,7-tetrahydroisoxazolo[3,4-b]pyridine-5-carboxylate The product from Example 45A (0.17 g, 1.5 mmol), ethyl 4-(acetyloxy)butanoate (0.28 g, 1.5 mmol), prepared as described in (Husband, et al., Tetrahedron (1995) 51(3), 865), and 3-bromo-4-fluorobenzaldehyde (0.3 g, 1.5 mmol) in ethyl alcohol (4 mL) were heated at 80° C. for 24 hours in a sealed tube. The reaction mixture was evaporated under reduced pressure and the residue chromatographed on silica gel eluting with 5% ethanol/methylene chloride to provide the title compound (0.2 g). $^1$H NMR (300 MHz, DMSO-$d_6$) δ 1.03 (t, 3H), 2.1 (s, 3H), 3.23 (s, 3H), 3.82 (q, 2H), 4.8 (s, 1H), 5.12 (q, 2H), 7.25 (m, 1H), 7.3 (t, 1H), 7.48 (dd, 1H), 10.2 (s, 1H); MS (ESI−) m/z 467 (M−H)$^-$.

Example 47B 4-(3-bromo-4-fluorophenyl)-1-methyl-4,8-dihydro-1H,3H-furo[3,4-b]isoxazolo[4,3-e]pyridine-3,5(7H)-dione The product from Example 47A (0.16 g) in methanol (10 mL) was treated with potassium carbonate(0.05 g) at ambient temperature. After stirring for 1 hour, the solvent was evaporated under reduced pressure and the residue was chromatographed on silica gel eluting with 5% ethanol/methylene chloride to provide the title compound (0.04). $^1$H NMR (300 MHz, DMSO-$d_6$) δ 3.28 (s, 3H),4.71 (s, 1H),4.96 (q, 2H), 7.32 (m, 2H), 7.58 (dd, 1H), 11.18 (bs, 1H); MS (ESI−) m/z 381 (M−H)$^-$.

EXAMPLE 48

4-(3-bromo-4-fluorophenyl)-1,2-dimethyl-1,2,4,9-tetrahydropyrano[3,4-b]pyrazolo[4,3-e]pyridine-3,5(6H,8H)-dione 2H-Pyran-3,5-(4H,6H)-dione (0.08 g, 0.7 mmol), 3-bromo-4-fluorobenzaldehyde (0.14 g, 0.7 mmol), and 5-amino-1,2-dimethyl-1,2-dihydro-3H-pyrazol-3-one (0.09 g, 0.7 mmol) in ethyl alcohol (2 mL) were heated at 80° C. for 24 hours in a sealed tube. The reaction mixture was allowed to cool to ambient temperature and then filtered to provide the title compound (0.11 g). $^1$H NMR (300 MHz, DMSO-$d_6$) δ 3.0 (s, 3H), 3.12 (s, 3H), 4.12 (s, 1H), 4.52 (q, 2H), 4.78 (s, 1H), 7.23 (m, 2H), 7.48 (dd, 1H), 10.18 (s, 1H); MS (ESI−) m/z 408 (M−H.)$^-$.

EXAMPLE 49

4-(3-bromo-4-methylphenyl)-1-methyl-4,9-dihydro-1H-isoxazolo[3,4-b]pyrano[4,3-e]pyridine-3,5(6H,8H)-dione The product from Example 45A (0.11 g, 1 mmol), 4-methyl-3-bromobenzaldehyde (0.2 g, 1 mmol), prepared as described in (Pearson et al., J.Org. Chem.(1958),23, 1412–1416) and 2H-pyran-3,5(4H,6H)-dione (0.11 g, 1 mmol) in ethyl alcohol (2 mL) were heated at 80° C. for 2 days in a sealed tube. The reaction mixture was allowed to cool to ambient temperature and was evaporated under reduced pressure. The residue was chromatographed eluting with 19:0.5:0.5 ethylacetate:formic acid: water to provide the title compound (0.07 g).
$^1$H NMR (300 MHz, DMSO-$d_6$) δ 2.29 (s, 3H), 3.23 (s, 3H), 4.05 (s, 2H), 4.55 (d, 2H), 4.7 (s, 1H), 7.11 (dd, 1H), 7.23 (d, 1H), 7.47 (d, 1H), 10.8 (s, 1H); MS (ESI) m/z 389 (M−H)$^-$; Anal. Calcd for $C_{17}H_{15}N_2BrO_4 \cdot 0.0.5C_2H_6O$: C, 52.19;H, 4.38; N, 6.76. Found: C, 51.88;H, 3.83; N, 6.34.

EXAMPLE 50

4-(2,1,3-benzoxadiazol-5-yl)-1-methyl-4,9-dihydro-1H-isoxazolo[3,4-b]pyrano[4,3-e]pyridine-3,5(6H,8H)-dione The product from Example 45A (0.11 g, 1 mmol), 2,1,3-benzoxadiazole-5-carboxaldehyde(0.15 g, 1 mmol), prepared as described in (Gasco, A. M., Ermondi, G. Eur. J. Med. Chem., (1996) 31, 3)and 2H-pyran-3,5(4H,6H)-dione (0.11 g, 1 mmol) were heated in 2 mL of ethanol for 2 days. The resulting mixture was allowed to cool to ambient temperature and filtered to provide the title compound as the filter cake (0.09 g). $^1$H NMR (300 MHz, DMSO-d$_6$) δ 3.28 (s, 3H), 4.08 (s, 2H), 4.6 (q, 2H), 4.92 (s, 1H), 7.62 (dd, 1H), 7.76 (s, 1H), 8.0 (dd, 1H), 10.8 (s, 1H); MS (ESI) m/z 339 (M–H)$^-$; Anal. Calcd for C$_{16}$H$_{12}$N$_4$O$_5$: C, 56.47; H, 3.52; N, 16.47. Found: C, 56.03;H, 3.97; N, 15.57.

EXAMPLE 51

4-[4-fluoro-3-(trifluoromethyl)phenyl]-1-methyl-4,9-dihydro-1H-isoxazolo[3,4-b]pyrano[4,3-e]pyridine-3,5(6H,8H)-dione The product from Example 45A (0.11 g, 1 mmol),4-fluoro-3-triflouromethylbenzaldehyde and 2H-pyran-3,5(4H,6H)-dione (0.11 g, 1 mmol) were heated in 2 mL of ethanol for 2 days. The reaction mixture was evaporated under reduced pressure and the remaining residue was triturated with methylene chloride. The resulting precipitate was filtered to provide the title compound as the filter cake. $^1$H NMR (300 MHz, DMSO-d$_6$) δ 3.28 (s, 3H), 4.07 (s, 2H), 4.58 (q, 2H), 4.87 (s, 1H), 7.42 (t, 1H), 7.59 (m, 2H), 10.8 (s, 1H); MS (ESI) m/z 383 (M–H)$^-$; Anal. Calcd for C$_{16}$H$_{12}$N$_2$F$_4$O$_4$: C, 51.61;H, 3.22; N, 7.52. Found: C, 51.09;H, 3.11; N,6.98.

EXAMPLE 52

4-(4-chloro-3-nitrophenyl)-1-methyl4,9-dihydro-1H-isoxazolo[3,4-b]pyrano[4,3-e]pyridine-3,5(6H,8H)-dione The product from Example 45A (0.085 g, 0.75 mmol), 3nitro-4-chlorobenzaldehyde(0.14 g, 0.75 mmol) and 2H-pyran-3,5(4H,6H)-dione (0.085 g, 0.75 mmol) were heated in 2 mL of ethanol for 2 days. The resulting mixture was allowed to cool to ambient temperature and filtered to provide the title compound as the filter cake (0.09 g). $^1$H NMR (300 MHz, DMSO-d$_6$) δ 3.28 (s, 3H), 4.06 (s, 2H), 4.58 (s, 2H), 4.88 (s, 1H), 7.6 (dd, 1H), 7.7 (d, 1H), 7.9 (d, 1H), 10.8 (s, 1H); MS (ESI) m/z 376 (M–H)$^-$; Anal. Calcd for C$_{16}$H$_{12}$N$_3$ClO$_6$: C, 50.88;H, 3.20; N, 11.12. Found: C, 50.86;H, 3.63; N, 10.52.

EXAMPLE 53

3-(1-methyl-3,5-dioxo-3,4,5,6,8,9-hexahydro-1H-isoxazolo[3,4-b]pyrano[4,3-e]pyridin-4-yl)benzonitrile The product from Example 45A (0.085 g, 0.75 mmol), 3-cyanobenzaldehyde (0.14 g, 0.75 mmol) and 2H-pyran-3,5(4H,6H)-dione (0.085 g, 0.75 mmol) were heated in 2 mL of ethanol for 2 days. The resulting mixture was allowed to cool to ambient temperature and filtered to provide the title compound as the filter cake (0.09 g). $^1$H NMR (300 MHz, DMSO-d$_6$) δ 3.28 (s, 3H), 4.05 (s, 2H), 4.59 (q, 2H), 4.81 (s, 1H), 7.5 (t, 1H), 7.6 (m, 1H), 7.62 (m, 1H), 7.64 (d, 1H), 10.8 (s, 1H); MS (ESI) m/z 322 (M–H)$^-$; Anal. Calcd for C$_{17}$H$_{13}$N$_3$O$_4$.0.25H$_2$O: C, 62.48;H, 3.86; N, 12.86. Found: C, 62.55;H, 4.07; N, 12.61.

EXAMPLE 54

4-(3-bromo-4-fluorophenyl)-1-methyl-4,6,7,8-tetrahydro-1H-cyclopenta[b]isoxazolo[4,3-e]pyridine-3,5-dione The product from Example 45A (0.11 g, 1 mmol), 3-bromo-4-fluorobenzaldehyde (0.2 g, 1 mmol), and 1,3-cyclopentanedione (0.1 g, 1 mmol) in ethyl alcohol (2 mL) were heated at 80° C. for 2 days in a sealed tube. The reaction mixture was allowed to cool to ambient temperature and was evaporated under reduced pressure. The residue was chromatographed eluting with 19:0.5:0.5 ethylacetate:formic acid: water to provide the title compound (0.07 g). $^1$H NMR (300 MHz, DMSO-d$_6$) δ 2.35 (t, 2H), 2.72 (m, 2H), 3.29 (s, 3H), 4.6 (s, 1H), 7.23 (d, 2H), 7.5 (d, 1H) 11.0 (s, 1H); MS (ESI) m/z 379 (M–H)$^-$; Anal. Calcd for C$_{16}$H$_{12}$N$_3$FBrO$_3$: C, 50.68;H, 3.19; N, 7.39. Found: C, 50.34;H, 3.20; N, 7.34.

EXAMPLE 55

4-(3-bromo-4-fluorophenyl)-1-methyl-4,7,8,9-tetrahydroisoxazolo[3,4-b]quinoline-3,5(1H,6H)-dione The product from Example 45A (0.086 g, 0.75 mmol), 3-bromo-4-fluorobenzaldehyde (0.15 g, 0.075 mmol), and 1,3-cyclohexanedione (0.084 g, 0.75 mmol) in ethyl alcohol (2 mL) were heated at 80° C. for 2 days in a sealed tube. The resulting mixture was allowed to cool to ambient temperature and filtered to provide the title compound as the filter cake (0.09 g). $^1$H NMR (300 MHz, DMSO-d$_6$) δ 1.95 (m, 2H), 2.27 (m, 2H), 2.63 (m, 2H), 3.24 (s, 3H), 4.69 (s, 1H), 7.2 (m, 1H), 7.23 (t, 1H), 7.45 (dd, 1H), 10.2 (s, 1H); MS (ESI) ml/z 393 (M–H)$^-$; Anal. Calcd for C$_{17}$H$_{14}$N$_2$BrFO$_3$: C, 62.48;H, 3.86;N, 12.86. Found: C, 62.55;H, 4.07; N, 12.61.

EXAMPLE 56

4-(4-fluoro-3-iodophenyl)-1-methyl-4,9-dihydro-1H-isoxazolo[3,4-b]pyrano[4,3-e]pyridine-3,5(6H,8H)-dione The product from Example 45A (0.086 g, 0.75 mmol), the product from Example 12C (0.19 g, 0.75 mmol) and 2H-pyran-3,5(4H,6H)-dione (0.085 g, 0.75 mmol) in ethyl alcohol (2 mL) were heated at 80° C. for 2 days in a sealed tube. The reaction mixture was allowed to cool to ambient temperature and was evaporated under reduced pressure. The residue was chromatographed eluting with 5% methanol/methylene chloride to provide the title compound (0.03 g). $^1$H NMR (300 MHz, DMSO-d$_6$) δ 3.23 (s, 3H), 4.06 (s, 2H), 4.58 (q, 2H), 4.72 (s, 1H), 7.18 (t, 1H), 7.25 (m, 1H), 7.63 (dd, 1H), 10.9 (s, 1H); MS (ESI) m/z 441 (M–H)$^-$; Anal. Calcd for C$_{16}$H$_{12}$N$_2$FIO$_4$: C, 43.46;H, 2.74; N, 6.34. Found: C, 42.96;H, 2.93; N, 5.98.

EXAMPLE 57

1-methyl-4-(5-nitro-3-thienyl)-4,9-dihydro-1H-isoxazolo[3,4-b]pyrano[4,3-e]pyridine-3,5(6H,8H)-dione The product from Example 45A (0.086 g, 0.75 mmol), nitro-3-thiophenecarbaldehyde (0.12 g, 0.75 mmol) and 2H-pyran-3,5(4H,6H)-dione (0.085 g, 0.75 mmol) in ethyl alcohol (2 mL) were heated at 80° C. for 2 days in a sealed tube. The reaction mixture was allowed to cool to ambient temperature and was evaporated under reduced pressure. The residue was crystallized from methylene chloride/ ethanol to provide the title product. $^1$H NMR (300 MHz, DMSO-d$_6$) δ 3.23 (s, 3H), 4.1 (q, 2H), 4.53 (s, 2H), 4.88 (s, 1H), 7.7 (d, 1H), 7.92 (d, 1H), 10.8 (s, 1H); MS (ESI) m/z 348 (M–H)$^-$; Anal. Calcd for C$_{14}$H$_{11}$N$_3$O$_6$S: C, 48.13;H, 3.15; N, 12.03. Found: C, 47.76;H, 3.25; N, 11.78.

Determination of Potassium Channel Opening
Activity Membrane Hyperpolarization Assays Compounds were evaluated for potassium channel opening activity using primary cultured guinea-pig urinary bladder (GPB) cells.

For the preparation of urinary bladder smooth muscle cells, urinary bladders were removed from male guinea-pigs (Hartley, Charles River, Wilmington, Mass.) weighing 300–400 g and placed in ice-cold $Ca^{2+}$-free Krebs solution (Composition, mM: KCl, 2.7; $KH_2PO_4$, 1.5; NaCl, 75; $Na_2HPO_4$, 9.6; $Na_2HPO_4 \cdot 7H_2O$, 8; $MgSO_4$, 2; glucose, 5; HEPES, 10; pH 7.4). Cells were isolated by enzymatic dissociation as previously described with minor modifications in (Klockner, U. and Isenberg, G., Pflugers Arch. 1985, 405, 329–339), hereby incorporated by reference. The bladder was cut into small sections and incubated in 5 mL of the Kreb's solution containing 1 mg/mL collagenase (Sigma, St. Louis, Mo.) and 0.2 mg/mL pronase (Calbiochem, La Jolla, Calif.) with continuous stirring in a cell incubator for 30 minutes. The mixture was then centrifuged at 1300×g for 5 minutes, and the pellet resuspended in Dulbecco's PBS (GIBCO, Gaithersburg, Md.) and recentrifuged to remove residual enzyme. The cell pellet was resuspended in 5 mL growth media (composition: Dulbecco's modified Eagle's medium supplemented with 10% fetal bovine serum, 100 units/mL penicillin, 100 units/mL streptomycin and 0.25 mg/mL amphotericin B) and further dissociated by pipetting the suspension through a flame-polished Pasteur pipette and passing it through a polypropylene mesh membrane (Spectrum, Houston, Tex.). The cell density was adjusted to 100,000 cells/mL by resuspension in growth media. Cells were plated in clear-bottomed black 96-well plates (Packard) for membrane potential studies at a density of 20,000 cells/well and maintained in a cell incubator with 90% air: 10% $CO_2$ until confluent. Cells were confirmed to be of smooth muscle type by cytoskeletal staining using a monoclonal mouse anti human-α-smooth muscle actin (Biomeda, Foster City, Calif.).

Functional activity at potassium channels was measured by evaluating changes in membrane potential using the bis-oxonol dye $DiBAC(4)_3$ (Molecular Probes) in a 96-well cell-based kinetic assay system, Fluorescent Imaging Plate Reader (FLIPR) (K. S. Schroeder et al., J. Biomed. Screen., v. 1 pp. 75–81 (1996)), hereby incorporated by reference. $DiBAC(4)_3$ is an anionic potentiometric probe which partitions between cells and extracellular solution in a membrane potential-dependent manner. With increasing membrane potential (for example, $K^+$ depolarization), the probe further partitions into the cell; this is measured as an increase in fluorescence due to dye interaction with intracellular lipids and proteins. Conversely, decreasing membrane potential (hyperpolarization by potassium channel openers) evokes a decrease in fluorescence.

Confluent guinea-pig urinary bladder cells cultured in black clear-bottomed 96-well plates were rinsed twice with 200 mL assay buffer (composition, mM: HEPES, 20; NaCl, 120; KCl, 2; $CaCl_2$, 2; $MgCl_2$, 1; glucose, 5; pH 7.4 at 25° C.) containing 5 $\mu$M $DiBAC(4)_3$ and incubated with 180 mL of the buffer in a cell incubator for 30 minutes at 37° C. to ensure dye distribution across the membrane. After recording the baseline fluorescence for 5 minutes, the reference or test compounds, prepared at 10 times the concentration in the assay buffer, were added directly to the wells. Changes in fluorescence were monitored for an additional 25 minutes. Hyperpolarization responses were corrected for any background noise and were normalized to the response observed with 10 $\mu$M of the reference compound P1075, N''-cyano-N-(tert-pentyl)-N'-(3-pyridinyl)guanidine, which was assigned as 100%. P1075 is a potent opener of smooth muscle $K_{ATP}$ channels (Quast et al., Mol. Pharmacol., v. 43 pp. 474–481 (1993)) and was prepared using the procedures described in (Manley, J. Med. Chem. (1992) 35, 2327–2340), hereby incorporated by reference.

Routinely, five concentrations of P1075 or test compounds (log or half-log dilutions) were evaluated and the maximal steady-state hyperpolarization values (expressed as % relative to P1075) plotted as a function of concentration. The $EC_{50}$ (concentration that elicites 50% of the maximal response for the test sample) values were calculated by non-linear regression analysis using a four parameter sigmoidal equation. The maximal response of each compound (expressed as % relative to P1075) is reported. Stock solutions of compounds were prepared in 100% DMSO and further dilutions were carried out in the assay buffer and added to a 96-well plate. The maximal steady-state hyperpolarization values (expressed as % relative to P1075) and the $EC_{50}$ values for representative compounds of the present invention are shown in Table 1.

TABLE 1

Membrane Hyperpolarization (MHP) in Guinea-Pig Bladder (GPB) Cells

| Example Number | Maximal Response (% P1075) | $EC_{50}(\mu M)$ |
| --- | --- | --- |
| 1 | 91 | 0.55 |
| 2 | 90 | 2.77 |
| 3 | 82 | 1.72 |
| 4 | 103 | 0.27 |
| 5 | — | >10 |
| 6 | — | >10 |
| 7 | — | >10 |
| 8 | 83 | 0.48 |
| 9 | 89 | 0.68 |
| 10 | 90 | 2.35 |
| 11 | 109 | 0.53 |
| 12 | 101 | 0.32 |
| 13 | 101 | 0.67 |
| 14 | — | >10 |
| 15 | 58 | 7.7 |
| 16 | — | >10 |
| 17 | — | >10 |
| 18 | 80 | 1.97 |
| 19 | — | >10 |
| 20 | 48 | >10 |
| 21 | — | >10 |
| 22 | 105 | 0.33 |
| 23 | 90 | 0.070 |
| 24 | 82 | 0.18 |
| 25 | 78 | 3.2 |
| 26 | 99 | 0.050 |
| 27 | | |
| 28 | | |
| 29 | | |
| 30 | | |
| 31 | 96 | 0.76 |
| 32 | 73 | 0.52 |

As shown by the data in Table 1, the compounds of this invention reduce stimulated contractions of the bladder and therefore may have utility in the treatment of diseases prevented by or ameliorated with potassium channel openers.

Compounds of the present invention may exist as stereoisomers wherein, asymmetric or chiral centers are present, These stereoisomers are "R" or "S" depending on the configuration of substituents around the chiral carbon atom.

The terms "R" and "S" used herein are configurations as defined in IUPAC 1974 Recommendations for Section E, Fundamental Stereochemistry, Pure Appl. Chem., 1976, 45: 13–30. In particular, the stereochemistry at the point of attachment of $R_1$, as shown in formula I–V, may independently be either (R) or (S), unless specifically noted otherwise. The present invention contemplates various stereoisomers and mixtures thereof and are specifically included within the scope of this invention. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The present invention provides pharmaceutical compositions which comprise compounds of the present invention formulated together with one or more non-toxic pharmaceutically acceptable carriers. The pharmaceutical compositions can be formulated for oral administration in solid or liquid form, for parenteral injection or for rectal administration.

Further included within the scope of the present invention are pharmaceutical compositions comprising one or more of the compounds of formula I–V prepared and formulated in combination with one or more non-toxic pharmaceutically acceptable compositions. The pharmaceutical compositions can be formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar—agar, tragacanth, and mixtures thereof.

If desired, and for more effective distribution, the compounds of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The active compounds can also be in micro-encapsulated form, if appropriate, with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions which can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidinone, sucrose, and acacia; c) humectants such as glycerol; d) disintegrating agents such as agar—agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate;) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Compounds of the present invention may also be administered in the form of liposomes. As is known in the art, liposomes are generally derived from phospholipidsor other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N. Y., (1976), p 33 et seq.

The terms "pharmaceutically acceptable salts, esters and amides," as used herein, refer to carboxylate salts, amino acid addition salts, zwitterions, esters and amides of compounds of formula I–V which are, within the scope of sound medical judgement, suitable for use in contact with the tissues of humans and lower animals without undue toxicity, irritation, allergic response, and the like, are commensurate with a reasonable benefit/risk ratio, and are effective for their intended use.

The compounds of the present invention can be used in the form of pharmaceutically acceptable salts derived from inorganic or organic acids. By "pharmaceutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quatemized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Preferred salts of the compounds of the invention include phosphate, tris and acetate.

The term "pharmaceutically acceptable ester," as used herein, refers to esters of compounds of the present invention which hydrolyze in vivo and include those that break down readily in the human body to leave the parent compound or a salt thereof. Examples of pharmaceutically acceptable, non-toxic esters of the present invention include $C_1$-to-$C_6$ alkyl esters and $C_5$-to-$C_7$ cycloalkyl esters, although $C_{1\text{-}to\text{-}C4}$ alkyl esters are preferred. Esters of the compounds of formula I–V may be prepared according to conventional methods. For example, 9-(3,4-dichlorophenyl)-3-(4-carboxyphenyl)-5,6,7,9-tetrahydropyrazolo[5,1-b]quinazolin-8(4H)-one can be treated with an acid, such as HCl, in an alcoholic solvent, such as methanol, to provide the ester 9-(3,4-dichlorophenyl)-3-(4-methoxycarbonylphenyl)-5,6,7,9-tetrahydropyrazolo[5,1-b]quinazolin-8(4H)-one.

The term "pharmaceutically acceptable amide," as used herein, refers to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula I–V may be prepared according to conventional methods. For example, 9-(3,4-dichlorophenyl)-3-(4carboxyphenyl)-5,6,7,9-tetrahydropyrazolo[5,1-b]quinazolin-8(4H)-one can be treated with a chloroformate, such as isobutylchloroformate, in an organic solvent, such as tetrahydrofuran or methylene chloride at a temperature of about 0° C. to ambient temperature, to provide an intermediate anhydride which can then be treated with an amine, such as dimethylamine, to provide 9(3,4-dichlorophenyl)-3-(4-dimethylaminocarbonylphenyl)-5,6,7,9-tetrahydropyrazolo [5,1-b]quinazolin-8(4H)-one. It is further intended that amides of the present invention include amino acid and peptide derivatives of the compounds of formula I, as well.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to the parent compound of the above formula, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

The present invention contemplates pharmaceutically active compounds either chemically synthesized or formed by in vivo biotransformation to compounds of formula I–V.

The compounds of the invention, including but not limited to those specified in the examples, possess potassium channel opening activity in mammals (especially humans). As potassium channel openers, the compounds of the present invention may be useful for the treatment and prevention of diseases such as asthma, epilepsy, male sexual dysfunction, female sexual dysfunction, pain, bladder overactivity, stroke, diseases associated with decreased skeletal blood flow such as Raynaud's phenomenon and intermittent claudication, eating disorders, functional bowel disorders, neurodegeneration, benign prostatic hyperplasia (BPH), dysmenorrhea, premature labor, alopecia, cardioprotection, coronary artery disease, angina and ischemia.

The ability of the compounds of the present invention, including but not limited to those specified in the examples, to treat bladder overactivity, sensations ofincontinence urgency, urinary incontinence, pollakiuria, bladder instability, nocturia, bladder hyerreflexia, and enuresis may be demonstrated by (Resnick, The Lancet (1995) 346, 94–99;Hampel, Urology (1997) 50 (Suppl 6A), 4–14; Bosch, BJU International (1999) 83 (Suppl 2), 7–9; Andersson, Urology (1997) 50 (Suppl 6A), 74–84; Lawson, Pharmacol. Ther., (1996) 70, 39–63; Nurse., Br. J. Urol., (1991) 68, 27–31;Howe, J. Pharmacol. Exp. Ther., (1995) 274, 884–890; Gopalakrishnan, Drug Development Research, (1993) 28, 95–127).

The ability of the compounds of the present invention, including but not limited to those specified in the examples, to treat male sexual dysfunction such as male erectile dysfunction, impotence and premature ejaculation may be demonstrated by (Andersson, Pharmacological Reviews (1993) 45, 253; Lee, Int. J. Impot. Res. (1999) 11(4), 179–188; Andersson, Pharmacological Reviews (1993) 45, 253; Lawson, Pharmacol. Ther., (1996) 70, 39–63, Vick, J. Urol. (2000) 163: 202).

The ability of the compounds of the present invention, including but not limited to those specified in the examples, to treat female sexual dysfunction such as clitoral erectile insufficiency, vaginismus and vaginal engorgement may be demonstrated by (J. J. Kim, J. W. Yu, J. G. Lee, D. G. Moon, "Effects of topical K-ATP channel opener solution on clitoral blood flow", J. Urol. (2000) 163 (4): 240; I. Goldstein and J. R. Berman., "Vasculogenic female sexual dysfunction: vaginal engorgement and clitoral erectile insufficiency syndromes"., Int. J. Impotence Res. (1998) 10:S84–S90).

The ability of the compounds of the present invention, including but not limited to those specified in the examples, to treat benign prostatic hyperplasia (BPH) may be demonstrated by (Pandita, The J. of Urology (1999) 162, 943;Andersson; Prostate (1997) 30: 202–215).

The ability of the compounds of the present invention, including but not limited to those specified in the examples, to treat premature labor and dysmenorrhoea may be demonstrated by (Sanbom, Semin. Perinatol. (1995) 19, 31–40; Morrison, Am. J. Obstet. Gynecol. (1993) 169(5), 1277-85; Kostrzewska, Acta Obstet. Gynecol. Scand.(1996) 75(10), 886-91; Lawson, Pharmacol. Ther., (1996) 70, 39–63).

The ability of the compounds of the present invention, including but not limited to those specified in the examples, to treat functional bowel disorders such as irritable bowel syndrome may be demonstrated by (Lawson, Pharmacol. Ther., (1996) 70, 39–63).

The ability of the compounds of the present invention, including but not limited to those specified in the examples, to treat asthma and airways hyperreactivity may be demonstrated by (Lawson, Pharmacol. Ther., (1996) 70, 39–63; Buchheit, Pulmonary Pharmacology & Therapeutics (1999) 12, 103; Gopalakrishnan, Drug Development Research, (1993) 28, 95–127).

The ability of the compounds of the present invention, including but not limited to those specified in the examples, to treat various pain states including but not limited to migraine and dyspareunia may be demonstrated by (Rodrigues, Br. J. Pharmacol.(2000) 129(1), 110-4; Vergoni, Life Sci. (1992) 50(16), PL135-8; Asano, Anesth. Analg. (2000) 90(5), 1146-51; Lawson, Pharmacol. Ther., (1996) 70, 39–63; Gopalakrishnan, Drug Development Research, (1993) 28, 95–127; Gehlert, Prog. Neuro-Psychopharmacol. & Biol. Psychiat., (1994) 18, 1093–1102).

The ability of the compounds of the present invention, including but not limited to those specified in the examples, to treat epilepsy may be demonstrated by (Lawson, Pharmacol. Ther., (1996) 70, 39–63; Gopalakrishnan, Drug Development Research, (1993) 28, 95–127; Gehlert, Prog. Neuro-Psychopharmacol & Biol. Psychiat., (1994) 18, 1093–1102).

The ability of the compounds of the present invention, including but not limited to those specified in the examples, to treat neurodegenerative conditions and diseases such as cerebral ischemia, stroke, Alzheimer's disease and Parkinson's disease may be demonstrated by (Lawson, Pharmacol. Ther., (1996) 70, 39–63; Gopalakrishnan, Drug Development Research, (1993) 28, 95–127; Gehlert, Prog. NeuroPsychopharmacol. & Biol. Psychiat., (1994) 18, 1093–1102; Freedman, The Neuroscientist (1996) 2, 145).

The ability of the compounds of the present invention, including but not limited to those specified in the examples, to treat diseases or conditions associated with decreased skeletal muscle blood flow such as Raynaud's syndrome and intermittent claudication may be demonstrated by (Lawson, Pharmacol. Ther., (1996) 70, 39–63; Gopalakrishnan, Drug Development Research, (1993) 28, 95–127; Dompeling Vasa. Supplementum (1992) 3434; WO9932495).

The ability of the compounds of the present invention, including but not limited to those specified in the examples, to treat eating disorders such as obesity may be demonstrated by (Spanswick, Nature, (1997) 390, 521-25; Freedman, The Neuroscientist (1996) 2, 145).

The ability of the compounds of the present invention, including but not limited to those specified in the examples, to treat alopecia may be demonstrated by (Lawson, Pharmacol. Ther., (1996) 70, 39–63; Gopalakrishnan, Drug Development Research, (1993) 28, 95–127).

The ability of the compounds of the present invention, including but not limited to those specified in the examples, to treat myocardial injury during ischemia and reperfusion may be demonstrated by (Garlid, Circ Res (1997) 81(6), 1072-82; Lawson, Pharmacol. Ther., (1996) 70, 39–63; Grover, J. Mol. Cell Cardiol. (2000) 32, 677).

The ability of the compounds of the present invention, including but not limited to those specified in the examples, to treat coronary artery disease may be demonstrated by (Lawson, Pharmacol. Ther., (1996) 70, 3963, Gopalakrishnan, Drug Development Research, (1993) 28, 95–127).

Aqueous liquid compositions of the present invention are particularly useful for the treatment and prevention of asthma, epilepsy, Raynaud's syndrome, male sexual dysfunction, female sexual dysfunction, migraine, pain, eating disorders, urinary incontinence, functional bowel disorders, neurodegeneration and stroke.

When used in the above or other treatments, a therapeutically effective amount of one of the compounds of the present invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.003 to about 25 mg/kg/day. For purposes of oral administration, more preferable doses can be in the range of from about 0.01 to about 5 mg/kg/day. If desired, the effective daily dose can be divided into multiple doses for purposes of administration; consequently, single dose compositions may contain such amounts or submultiples thereof to make up the daily dose.

We claim:

1. A compound having formula I:

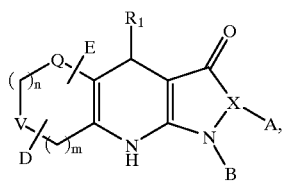

I or a pharmaceutically acceptable salt thereof wherein,
m is 1;
n is 1;
$R^1$ is selected from the group consisting of aryl and heterocycle;
Q is selected from the group consisting of C(O), S(O), and $S(O)_2$;
V is selected from the group consisting of $C(R)(R_3)$, O, S, and $NR_4$;
$R_2$ and $R_3$ are independently absent or selected from the group consisting of hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, —$NR_5R_6$, and ($NR_5R_6$)alkyl;
$R_4$ is selected from the group consisting of hydrogen, alkenyl, alkoxy, alkoxyalkoxy, alkoxyalkyl, alkyl, alkynyl, aryl, arylalkoxy, arylalkenyl, arylalkyl, cyano, cycloalkyl, cycloalkylalkyl, haloalkoxy, haloalkyl, heterocycle, heterocyclealkyl, hydroxy, hydroxyalkyl, —$NR_5R_6$, and ($NR_5R_6$)alkyl;

$R_5$ and $R_6$ are independently selected from the group consisting of hydrogen and lower alkyl;
X is selected from the group consisting of O and N;
A is absent or selected from the group consisting of hydrogen, alkenyl, alkoxy, alkoxyalkoxy, alkoxyalkyl, alkoxycarbonyl, alkyl, alkylcarbonyl, alkylsulfonyl, alkynyl, aryl, arylalkoxy, arylalkenyl, arylalkyl, cycloalkyl, cycloalkylalkyl, haloalkoxy, haloalkyl, halogen, heterocycle, heterocyclealkyl, hydroxy, hydroxyalkyl, —$NR_5R_6$, and ($NR_4R_6$)alkyl;
B is selected from the group consisting of hydrogen, alkenyl, alkoxy, alkoxyalkoxy, alkoxyalkyl, alkoxycarbonyl, alkyl, alkylcarbonyl, alkynyl, aryl, arylalkoxy, arylalkenyl, arylalkyl, cycloalkyl, cycloalkylalkyl, haloalkoxy, haloalkyl, haloalkylcarbonyl, halogen, heterocycle, heterocyclealkyl, hydroxy, hydroxyalkyl, —$NR_5R_6$, and ($NR_5R_6$)alkyl;
D and E are independently selected from the group consisting of hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, —$NR_5R_6$, and ($NR_5R_6$)alkyl.

2. A compound according to claim 1 of formula III:

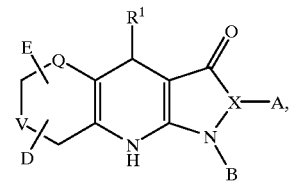

III or a pharmaceutically acceptable salt thereof.

3. A compound according to claim 2 wherein
Q is C(O); and
V is O.

4. A compound according to claim 2 wherein
X is N;
Q is C(O);
V is O;
A is selected from the group consisting of hydrogen, alkyl, alkylcarbonyl, alkoxycarbonyl, and aryl;
B is selected from the group consisting of hydrogen, alkyl, and heterocycle; and
D and E are hydrogen.

5. A compound according to claim 2 wherein
X is N;
Q is C(O);
V is O;
A is selected from the group consisting of hydrogen, alkyl, alkylcarbonyl, and alkoxycarbonyl;
B is alkyl; and
D and E are hydrogen.

6. A compound according to claim 5 selected from the group consisting of 4-(3-bromo-4-fluorophenyl)-1-methyl-1,2,4,9-tetrahydropyrano[3,4-b]pyrazolo[4,3-e]pyridine-3,5(6H,8H)-dione;

4-(3-bromo-4-fluorophenyl)-1-ethyl-1,2,4,9-tetrahydropyrano[3,4b]pyrazolo[4,3-e]pyridine-3,5(6H,8H)-dione;

4-(4-fluoro-3-iodophenyl)-1-methyl-1,2,4,9-tetrahydropyrano[3,4-b]pyrazolo[4,3-e]pyridine-3,5(6H,8H)-dione;

4-(3-iodo-4-methylphenyl)-1-methyl-1,2,4,9-tetrahydropyrano[3,4b]pyrazolo[4,3-e]pyridine-3,5(6H,8H)-dione;

4-(4-bromo-3-chlorophenyl)-1-methyl-1,2,4,9-tetrahydropyrano[3,4-b]pyrazolo[4,3-e]pyridine-3,5(6H,8H)-dione;

2-acetyl-4-(3-bromo-4-fluorophenyl)-1-methyl-1,2,4,9-tetrahydropyrano[3,4-b]pyrazolo[4,3-e]pyridine-3,5(6H,8H)-dione; and 4-(3-bromo-4-fluorophenyl)-1,2-dimethyl-1,2,4,9-tetrahydropyrano[3,4-b]pyrazolo[4,3-e]pyridine-3,5(6H,8H)-dione.

7. A compound according to claim 2 wherein

X is N;

Q is C(O);

V is O;

A is selected from the group consisting of hydrogen, alkyl, alkylcarbonyl, and alkoxycarbonyl;

B and D are alkyl; and

E is selected from the group consisting of hydrogen and alkyl.

8. A compound according to claim 7 selected from the group consisting of 4-(3-bromo-4-fluorophenyl)-1,6-dimethyl-1,2,4,9-tetrahydropyrano[3,4-b]pyrazolo[4,3-e]pyridine-3,5(6H,8H)-dione; and 4-(3-bromo-4-fluorophenyl)-1,6,6-trimethyl-1,2,4,9-tetrahydropyrano[3,4-b]pyrazolo[4,3-e]pyridine-3,5(6H,8H)-dione.

9. A compound according to claim 2 wherein

X is O;

Q is C(O);

V is O;

A is absent;

B is alkyl; and

D and E are hydrogen.

10. A compound according to claim 9 selected from the group consisting of 4-(3-bromo-4-fluorophenyl)-1-methyl-4,9-dihydro-1H-isoxazolo[3,4-b]pyrano[4,3-e]pyridine-3,5(6H,8H)-dione;

4-(3-bromo-4-methylphenyl)-1-methyl-4,9-dihydro-1H-isoxazolo[3,4-b]pyrano[4,3-e]pyridine-3,5(6H,8H)-dione;

4-(2,1,3-benzoxadiazol-5-yl)-1-methyl-4,9-dihydro-1H-isoxazolo[3,4-b]pyrano[4,3-e]pyridine-3,5(6H,8H)-dione;

4-[4-fluoro-3-(trifluoromethyl)phenyl]-1-methyl-4,9-dihydro-1H-isoxazolo[3,4-b]pyrano[4,3-e]pyridine-3,5(6H,8H)-dione;

4-(4-chloro-3-nitrophenyl)-1-methyl-4,9-dihydro-1H-isoxazolo[3,4-b]pyrano[4,3-e]pyridine-3,5(6H,8H)-dione;

3-(1-methyl-3,5-dioxo-3,4,5,6,8,9-hexahydro-1H-isoxazolo[3,4-b]pyrano[4,3 e]pyridin-4-yl)benzonitrile;

4-(4-fluoro-3-iodophenyl)-1-methyl-4,9-dihydro-1H-isoxazolo[3,4-b]pyrano[4,3-e]pyridine-3,5(6H,8H)-dione; and 1-methyl-4-(5-nitro-3-thienyl)-4,9-dihydro-1H-isoxazolo[3,4-b]pyrano[4,3-e]pyridine-3,5(6H,8H)-dione.

11. A pharmaceutical composition comprising a therapeutically effective amount of a compound of claim 1 in combination with a pharmaceutically acceptable carrier.

12. A method of treating a disorder selected from the group consisting of asthma, epilepsy, Raynaud's syndrome, itermittent claudication, migraine, pain, pollakiuria, bladder instability, nocturia, bladder hyperreflexia, enuresis, alopecia, ischemia, cardioprotection, eating disorders, neurodegeneration, functional bowel disorders, bladder overactivity, urinary incontinence, dysmenorrhea, bengign prostatic hyperplasia, premature labor, make erectile dysfunction, premature ejaculation and female sexual dysfunction in a host mammal in need of such treatment comprising administering to said host mammal a compound of formula (I) of claim 1 in an amount effective for opening the potassium channel.

13. The method of claim 12 wherein the disorder is bladder overactivity.

14. The method of claim 12 wherein the disorder is benign prostatic hyperplasia.

15. The method of claim 12 wherein the disorder is dysmenorrhea.

16. The method of claim 12 wherein the disorder is premature labor.

17. The method of claim 12 wherein the disorder is urinary incontinence.

18. The method of claim 12 wherein the disorder is selected from the group consisting of male erectile dysfunction and premature ejaculation.

19. The method of claim 12 wherein the disorder is female sexual dysfunction.

* * * * *

UNITED STATES PATENT AND TRADEMARK OFFICE
CERTIFICATE OF CORRECTION

PATENT NO.    : 6,538,004 B2
DATED         : March 25, 2003
INVENTOR(S)   : Irene Drizin et al.

It is certified that error appears in the above-identified patent and that said Letters Patent is hereby corrected as shown below:

Column 76,
Line 14, replace "(NR4R6)alkyl;" with -- (NR5R6)alkyl; --.

Column 77,
Lines 5 and 11, replace "[3,4b]pyrazolo" with -- [3,4-b]pyrazolo --.

Column 78,
Lines 22-23, replace "thereapeutically" with -- therapeutically --.
Line 27, replace "itermittent" with -- intermittent --.
Line 31, replace "bengign" with -- benign --.
Line 32, replace "make" with -- male --.

Signed and Sealed this

Second Day of September, 2003

JAMES E. ROGAN
*Director of the United States Patent and Trademark Office*